(12) United States Patent
Rohlff et al.

(10) Patent No.: US 8,540,998 B2
(45) Date of Patent: Sep. 24, 2013

(54) METHODS FOR TREATING CANCER USING EPHRIN TYPE-A RECEPTOR 10 ANTIBODIES CONJUGATED TO CYTOTOXIC AGENTS

(75) Inventors: Christian Rohlff, Abingdon (GB); Alasdair Stamps, Abingdon (GB)

(73) Assignee: Oxford Biotherapeutics Ltd., Abingdon Oxon (GB)

( * ) Notice: Subject to any disclaimer, the term of this patent is extended or adjusted under 35 U.S.C. 154(b) by 31 days.

(21) Appl. No.: 12/810,095

(22) PCT Filed: Dec. 24, 2008

(86) PCT No.: PCT/IB2008/003634
§ 371 (c)(1),
(2), (4) Date: Sep. 28, 2010

(87) PCT Pub. No.: WO2009/087462
PCT Pub. Date: Jul. 16, 2009

(65) Prior Publication Data
US 2011/0027173 A1    Feb. 3, 2011

Related U.S. Application Data

(60) Provisional application No. 61/008,775, filed on Dec. 24, 2007.

(51) Int. Cl.
*A61K 39/00*         (2006.01)

(52) U.S. Cl.
USPC .................................... 424/183.1; 424/178.1

(58) Field of Classification Search
None
See application file for complete search history.

(56) References Cited

U.S. PATENT DOCUMENTS

| 7,074,899 B2 | 7/2006 | Hock et al. |
| 2006/0121042 A1 | 6/2006 | Dall'Acqua et al. |

FOREIGN PATENT DOCUMENTS

| JP | 2003/052384 A | 2/2003 |
| WO | 01/74851 A | 10/2001 |
| WO | 02/08253 A | 1/2002 |
| WO | 2006/023403 A | 3/2006 |
| WO | WO 2007/030642 | 3/2007 |
| WO | WO 2008/066498 | 6/2008 |

OTHER PUBLICATIONS

Surawska H, et al. Cytokine & Growth Factor Reviews 15:419-433, 2004.*
Aasheim, H.C. et al., "Characterization of a Novel Eph Receptor Tyrosine Kinase, EphA10, Expressed in Testis," Biochimica Et Biophysica Acta, v. 1723, n. 1-3, p. 1-7, May 25, 2005.
Abraham, Shaji et al., "Expression of EphA2 and Ephrin A-1 in Carcinoma of the Urinary Bladder," Clinical Cancer Research: An Offical Journal of the Amer. Assoc. for Cancer Res. v. 12, n. 2, p. 353-360, Jan. 15, 2006.
Aparicio, Ana, et al., "Review of the Clinical Experience with 5-Azacytidine and 5-aza-2'- Deoxycytidine in Solid Tumors," Current Opinion in Invest. Drugs, v. 3, n. 4, p. 627-633, Apr. 1, 2002.
Fox, B.P. et al., "Invasivenss of Breast Carcinoma Cells and Transcript Profile: Eph Receptors and Ephrin Ligands as Milecular Markers of Potential Diagnostic and Prognostic Application," Biochemical and Biophysical Res. Commun., v. 318, n. 4. p. 882-892, Jun. 11, 2004.
Fox, B.P., et al., "Potential Clinical Relevance of Eph Receptors and Ephrin Ligands xpressed in Prostate Carcinoma Cell Lines," Biochemical and Biophysical Res. Commun., v. 342, n. 4, p. 1263-1272, Apr. 21, 2006.
Hatano, Manabu, et al., "Vaccination with EphA2-Derived T Cell-Epitopes Promotes Immunity aginst both EphA2-Expressing and EphA2-Negative Tumors," J. of Translational Med., v. 2, n. 1, p. 40, Nov. 24, 2004.
Kiewlich, David et al., "Anti-EphA2 Antibodies Decrease EphA2 Protein Levels in Murine CT26 Colorectal and Human MDA-231 Breast Tumors but do not Inhibit Tumor Growth," Neoplasia, v. 8, n. 1, p. 18-30, Jan. 2006.
Landen, C.N., et al., EphA2 as a Target for Ovarian Cancer Therapy, Expert Opinion on Therapeutic Targets, v. 9, n. 6, p. 1179-1187, Dec. 1, 2005.
Wu, Dan et al., "Prognostic Value of EphA2 and EphrinA-1 in Squamous Cell Cervical Carcinoma," Gynecologic Oncology, v. 94, n. 2, p. 312-319, Aug. 2004.
Winter J, et al., "Comparative 3'UTR analysis allows identification of regulatory clusters that drive Eph/ephrin expression in cancer cell lines.", PLoS One, 2008, e2780, vol. 3, No. 7.
Alonso-C LM, et al., "Expression profile of Eph receptors and ephrin ligands in healthy human B lymphocytes and chronic lymphocytic leukemia B-cells.", Leuk. Res., 2009, pp. 395-406, vol. 33, No. 3.
Lackmann M, et al., "Eph, a protein family coming of age: more confusion, insight, or complexity?", Sci. Signal., 2008, p. re2, vol. 1, issue 15.
Hafner C, et al., "Expression profile of Eph receptors and ephrin ligands in human skin and downregulation of EphA1 in nonmelanoma skin cancer.", Mod. Pathol., 2006, pp. 1369-1377, vol. 19, no. 10.
Boudeau J, et al., "Emerging roles of pseudokinases.", Trends Cell Biol., 2006, pp. 443-452, vol. 16, No. 9.
Katoh Y, et al., "Comparative integromics on Eph family.", Oncol. Rep., 2006, pp. 1391-1395, vol. 15, No. 5.
Surawska H, et al., "The role of ephrins and Eph receptors in cancer.", Cytokine Growth Factor Rev., 2004, pp. 419-433, vol. 15, No. 6.

(Continued)

*Primary Examiner* — Robert Landsman
(74) *Attorney, Agent, or Firm* — Morgan Lewis & Bockius LLP

(57) ABSTRACT

The present invention provides methods and compositions for treatment, screening, diagnosis and prognosis of bladder cancer, breast cancer, colorectal cancer, head and neck cancer, kidney cancer, lung cancer or pancreatic cancer, for monitoring the effectiveness of bladder cancer, breast cancer, colorectal cancer, head and neck cancer, kidney cancer, lung cancer or pancreatic cancer treatment, and for drug development based on Ephrin Type-A Receptor 10 Protein.

2 Claims, 6 Drawing Sheets

(56) References Cited

OTHER PUBLICATIONS

Miao H, et al., "Inhibition of integrin-mediated cell adhesion but not directional cell migration requires catalytic activity of EphB3 receptor tyrosine kinase. Role of Rho family small GTPases.", J. Biol. Chem., 2005, pp. 923-932, vol. 280, No. 2.

Murai KK, et al., "Eph Receptors, Ephrins, and Synaptic Function.", Neuroscientist, 2004, pp. 304-314, vol. 10, No. 4.

Manning G, et al., "The protein kinase complement of the human genome.", Science, 2002, pp. 1912-1934, vol. 298, No. 5600.

Gurniak CB, et al., "A new member of the Eph family of receptors that lacks protein tyrosine kinase activity.", Oncogene, 1996, pp. 777-786, vol. 13, No. 4.

Wolff AC, et al., "American Society of Clinical Oncology/College of American Pathologists guideline recommendations for human epidermal growth factor receptor 2 testing in breast cancer.", Arch. Pathol. Lab. Med., 2007, pp. 18-43, vol. 131, No. 1.

Oerntoft TF, et al., "Genome-wide study of gene copy numbers, transcripts, and protein levels in pairs of non invasive and invasive human transitional cell carcinomas.", Mol. Cell. Proteomics, 2002, pp. 37-45, vol. 1, No. 1.

\* cited by examiner

Figure 1

OGTA298 (SEQ ID Nos: 1-6)

Peptide Source: iTRAQ™ Colorectal cancer

<u>SEQ. ID. NO.: 1</u>

METCAGPHPLRLFLCRMQLCLALLLGPWRPGTAEEVILLDSKASQAELGWTALPSNGWEEISGVDEHDR
PIRTYQVCNVLEPNQDNWLQTGWISRGRGQRIFVELQFTLRDCSSIPGAAGTCKETFNVYYLETEADLG
RGRPRLGGSRPRKIDTIAADESFTQGDLGERKMKLNTEVREIGPLSRRGFHLAFQDVGACVALVSVRVY
YKQCRATVRGLATFPATAAESAFSTLVEVAGTCVAHSEGEPGSPPRMHCGADGEWLVPVGRCSCSAGFQ
ERGDFCEACPPGFYKVSPRRPLCSPCPEHSRALENASTFCVCQDSYARSPTDPPSASCTRPPSAPRDLQ
YSLSRSSPLVLRLRWLPPADSGGRSDVTYSLLCLRCGREGPAGACEPCGPRVAFLPRQAGLRERAATLLH
LRPGARYTVRVAALNGVSGPAAAAGTTYAQVTVSTGPGAPWEEGEIRRDRVEPQSVSLSWREPIPAGAP
GANDTEYEIRYYEKGQSEQAYSMVKTGAPTVTVTNLKPATRYVFQIRAASPGPSWEAQSFNPSIEVQTL
GEAASGSRDQSPAIVVTVVTISALLVLGSVMSVLAIWRRPCSYGKGGGDAHDEEELYFHFKVPTRRTFL
DPQSCGDLLQAVHLFAKELDAKSVTLERSLGGGRFGELCCGCLQLPGRQELLVAVHMLRDSASDSQRLG
FLAEALTLGQFDHSHIVRLEGVVTRGSTLMIVTEYMSHGALDGFLRRHEGQLVAGQLMGLLPGLASAMK
YLSEMGYVHRGLAARHVLVSSDLVCKISGFGRGPRDRSEAVYTTMSGRSPALWAAPETLQFGHFSSASD
VWSFGIIMWEVMAFGERPYWDMSGQDVIKAVEDGFRLPPPRNCPNLLHRLMLDCWQKDPGERPRFSQIH
SILSSKMVQDPEPPKCALTTCPRPPTPLADRAFSTFPSFGSVGAWLEALDLCRYKDSFAAAGYGSLEAVA
EMTAQDLVSLGISLAEHREALLSGISALQARVLQLQGQGVQV

Mass Match Peptides:
    FSQIHSILSKMVQDPEPPK [SEQ. ID. NO.:3]
    HEGQLVAGQLMGLLPGLASAMK [SEQ. ID. NO.:4]
    LEGVVTR [SEQ. ID. NO.:5]
    SPLVLR [SEQ. ID. NO.:6]

Tandem Peptides:
    FSQIHSILSKMVQDPEPPK [SEQ. ID. NO.:3]
    HEGQLVAGQLMGLLPGLASAMK [SEQ. ID. NO.:4]
    LEGVVTR [SEQ. ID. NO.:5]
    SPLVLR [SEQ. ID. NO.:6]

Peptide Source: iTRAQ™ Kidney cancer

<u>SEQ ID NO: 1</u>

METCAGPHPLRLFLCRMQLCLALLLGPWRPGTAEEVILLDSKASQAELGWTALPSNGWEEISGVDEHDR
PIRTYQVCNVLEPNQDNWLQTGWISRGRGQRIFVELQFTLRDCSSIPGAAGTCKETFNVYYLETEADLG
RGRPRLGGSRPRKIDTIAADESFTQGDLGERKMKLNTEVREIGPLSRRGFHLAFQDVGACVALVSVRVY
YKQCRATVRGLATFPATAAESAFSTLVEVAGTCVAHSEGEPGSPPRMHCGADGEWLVPVGRCSCSAGFQ
ERGDFCEACPPGFYKVSPRRPLCSPCPEHSRALENASTFCVCQDSYARSPTDPPSASCTRPPSAPRDLQ
YSLSRSPLVLRLRWLPPADSGGRSDVTYSLLCLRCGREGPAGACEPCGPRVAFLPRQAGLRERAATLLH
LRPGARYTVRVAALNGVSGPAAAAGTTYAQVTVSTGPGAPWEEGEIRRDRVEPQSVSLSWREPIPAGAP
GANDTEYEIRYYEKGQSEQAYSMVKTGAPTVTVTNLKPATRYVFQIRAASPGPSWEAQSFNPSIEVQTL
GEAASGSRDQSPAIVVTVVTISALLVLGSVMSVLAIWRRPCSYGKGGGDAHDEEELYFHFKVPTRRTFL
DPQSCGDLLQAVHLFAKELDAKSVTLERSLGGGRFGELCCGCLQLPGRQELLVAVHMLRDSASDSQRLG
FLAEALTLGQFDHSHIVRLEGVVTRGSTLMIVTEYMSHGALDGFLRRHEGQLVAGQLMGLLPGLASAMK
YLSEMGYVHRGLAARHVLVSSDLVCKISGFGRGPRDRSEAVYTTMSGRSPALWAAPETLQFGHFSSASD
VWSFGIIMWEVMAFGERPYWDMSGQDVIKAVEDGFRLPPPRNCPNLLHRLMLDCWQKDPGERPRFSQIH
SILSKMVQDPEPPKCALTTCPRPPTPLADRAFSTFPSFGSVGAWLEALDLCRYKDSPAAAGYGSLEAVA
EMTAQDLVSLGISLAEHREALLSGISALQARVLQLQGQGVQV

Mass Match Peptides:
    SPLVLR [SEQ. ID. NO.:6]

Tandem Peptides:
    SPLVLR [SEQ. ID. NO.:6]

Figure 1 (cont.)

SEQ ID Nos. 1-6 (cont.)

Peptide Source: iTRAQ™ Non-small cell lung cancer

SEQ ID NO: 1

METCAGPHPLRLFLCRMQLCLALLLGPWRPGTAEEVILLDSKASQAELGWTALPSNGWEEISGVDEHDR
PIRTYQVCNVLEPNQDNWLQTGWISRGRGQRIFVELQFTLRDCSSIPGAAGTCKETFNVYYLETEADLG
RGRPRLGGSRPRKIDTIAADESFTQGDLGERKMKLNTEVREIGPLSRRGFHLAFQDVGACVALVSVRVY
YKQCRATVRGLATFPATAAESAFSTLVEVAGTCVAHSEGEPGSPPRMHCGADGEWLVPVGRCSCSAGFQ
ERGDFCEACPPGFYKVSPRRPLCSPCPEHSRALENASTFCVCQDSYARSPTDPPSASCTRPPSAPRDLQ
YSLSRSPLVLRLRWLPPADSGGRSDVTYSLLCLRCGREGPAGACEPCGPRVAFLPRQAGLRERAATLLH
LRPGARYTVRVAALNGVSGPAAAAGTTYAQVTVSTGPGAPWEEGEIRRDRVEPQSVSLSWREPIPAGAP
GANDTEYEIRYYEKGQSEQAYSMVKTGAPTVTVTNLKPATRYVFQIRAASPGPSWEAQSFNPSIEVQTL
GEAASGSRDQSPAIVVTVVTISALLVLGSVMSVLAIWRRPCSYGKGGGDAHDEEELYFHFKVPTRRTFL
DPQSCGDLLQAVHLFAKELDAKSVTLERSLGGGRFGELCCGCLQLPGRQELLVAVHMLRDSASDSQRLG
FLAEALTLGQFDHSHIVRLEGVVTRGSTLMIVTEYMSHGALDGFLRRHEGQLVAGQLMGLLPGLASAMK
YLSEMGYVHRGLAARHVLVSSDLVCKISGFGRGPRDRSEAVYTTMSGRSPALWAAPETLQFGHFSSASD
VWSFGIIMWEVMAFGERPYWDMSGQDVIKAVEDGFRLPPPRNCPNLLHRLMLDCWQKDPGERPRFSQIH
SILSKMVQDPEPPKCALTTCPRPPTPLADRAFSTFPSFGSVGAWLEALDLCRYKDSPAAAGYGSLEAVA
EMTAQDLVSLGISLAEHREALLSGISALQARVLQLQGQGVQV

Mass Match Peptides:
    SPLVLR [SEQ. ID. NO.:6]

Tandem Peptides:
    SPLVLR [SEQ. ID. NO.:6]

Peptide Source: iTRAQ™ Small cell lung cancer

SEQ ID NO: 1

METCAGPHPLRLFLCRMQLCLALLLGPWRPGTAEEVILLDSKASQAELGWTALPSNGWEEISGVDEHDR
PIRTYQVCNVLEPNQDNWLQTGWISRGRGQRIFVELQFTLRDCSSIPGAAGTCKETFNVYYLETEADLG
RGRPRLGGSRPRKIDTIAADESFTQGDLGERKMKLNTEVREIGPLSRRGFHLAFQDVGACVALVSVRVY
YKQCRATVRGLATFPATAAESAFSTLVEVAGTCVAHSEGEPGSPPRMHCGADGEWLVPVGRCSCSAGFQ
ERGDFCEACPPGFYKVSPRRPLCSPCPEHSRALENASTFCVCQDSYARSPTDPPSASCTRPPSAPRDLQ
YSLSRSPLVLRLRWLPPADSGGRSDVTYSLLCLRCGREGPAGACEPCGPRVAFLPRQAGLRERAATLLH
LRPGARYTVRVAALNGVSGPAAAAGTTYAQVTVSTGPGAPWEEGEIRRDRVEPQSVSLSWREPIPAGAP
GANDTEYEIRYYEKGQSEQAYSMVKTGAPTVTVTNLKPATRYVFQIRAASPGPSWEAQSFNPSIEVQTL
GEAASGSRDQSPAIVVTVVTISALLVLGSVMSVLAIWRRPCSYGKGGGDAHDEEELYFHFKVPTRRTFL
DPQSCGDLLQAVHLFAKELDAKSVTLERSLGGGRFGELCCGCLQLPGRQELLVAVHMLRDSASDSQRLG
FLAEALTLGQFDHSHIVRLEGVVTRGSTLMIVTEYMSHGALDGFLRRHEGQLVAGQLMGLLPGLASAMK
YLSEMGYVHRGLAARHVLVSSDLVCKISGFGRGPRDRSEAVYTTMSGRSPALWAAPETLQFGHFSSASD
VWSFGIIMWEVMAFGERPYWDMSGQDVIKAVEDGFRLPPPRNCPNLLHRLMLDCWQKDPGERPRFSQIH
SILSKMVQDPEPPKCALTTCPRPPTPLADRAFSTFPSFGSVGAWLEALDLCRYKDSPAAAGYGSLEAVA
EMTAQDLVSLGISLAEHREALLSGISALQARVLQLQGQGVQV

Mass Match Peptides:
    EIGPLSR [SEQ. ID. NO.:2]

Tandem Peptides:
    EIGPLSR [SEQ. ID. NO.:2]

Figure 2 (SEQ ID No. 7)

```
   1 ggctctgggg nctggggggca ttgctcagcg gtgctaggct ggagcggctt gagccgccgc
  61 cggactgaca gctcggtctg cggaccatgg agacctgcgc cggtccacac ccgctgcgcc
 121 tcttcctctg ccggatgcag ctctgtctcg cgctgctttt gggaccctgg cggcctggga
 181 ccgccgagga agttatcctc ctggattcca aagcctccca ggccgagctg ggctggactg
 241 cactgccaag taatgggtgg gaggagatca gcggcgtgga tgaacacgac cgtcccatcc
 301 gcacgtacca agtgtgcaat gtgctggagc ccaaccagga caactggctg cagactgget
 361 ggataagccg tggccgcggg cagcgcatct tcgtggaact gcagttcaca ctccgtgact
 421 gcagcagcat ccctggcgcc gcgggtacct gcaaggagac cttcaacgtc tactacctgg
 481 aaactgaggc cgacctgggc agtgggcgtc ccgcctaggc ggcagccgg ccccgcaaaa
 541 tcgacacgat cgcggcggac gagagcttca cgcagggcga cctgggtgag cgcaagatga
 601 agctgaacac agaggtgcgc gagatcggac cgctcagccg gggggttttc cacctggcct
 661 ttcaggacgt gggcgcatgc gtggcgcttg tctcggtgcg cgtctactac aagcagtgcc
 721 gcgccaccgt gcgggggctg gccacgttcc cagccaccgc agccgagagc gccttctcca
 781 cactggtgga agtggccgga acgtgcgtgg cgcactagga agggagcct ggcagcccc
 841 cacgcatgca ctgcggcgcc gacggcgagt ggctggtgcc tgtgggccgc tgcagtgca
 901 gcgcgggatt ccaggagcgt ggtgacttct gcgaagcctg tcccccaggg ttttacaagg
 961 tgtcccgcg gcggcccatc tgctcaccgt gcccagagca cagccgggcc ctggaaaacg
1021 cctccacctt ctgcgtgtgc caggacagct atgccgctc acccaccgac ccgcccctgg
1081 cttcctgcac ccggccgcg tggcgccgc gggacctgca gtacagcctg agccgctcgc
1141 cgctggtgct gcgactgcgc tgctgccgc cggccgactc gggaggccgc tcggacgtca
1201 cctactcgct gctgtgcctg cgctgcggcc gcgagggccc ggcgggcgcc tgcagccgt
1261 gcgggccgcg cgtggccttc ctaccgcgcc aggcagggct gcgggagcga gccgccaccgc
1321 tgctgcacct gcgggcccggc gcgcgctaca ccgtgcgcgt ggccgcgctc aacggcgtct
1381 cgggccccgcg ccgccgcgcg ggaaccacct acgcaggt caccgtctcc acccggcccg
1441 gggcgccctg ggaggaggat gagatccgca ggaccgagt ggaacccccag agcgtgtccc
1501 tgtcgtggcg ggagcccatc cctgccggag ccctgggcc caatgacacg gagtacgaga
1561 tccgatacta cgagaagggt cagagtgagc agacttactc catggtgaag acaggggcgc
1621 ccacagtcac cgtcaccaac ctgaagccgg ctacccgcta cgtctttcag atccgggccg
1681 cttcccgggg gccatcctgg gaggcccaga gttttaaccc cagcattgaa gtacagaccc
```

Figure 2(cont.)

SEQ ID No. 7 (cont.)

```
    1741 tggggaggc tgcctcaggg tccagggacc agagcccgc cattgtcgtc
accgtagtga
    1801 ccatctggc cctcctcgtc ctgggctccg tgatgagtgt gctggccatt
tggaggaggc
    1861 cctgcagcta tggcaaagga ggaggggatg cccatgatga agaggagctg
tatttccact
    1921 tcaaagtccc aacacgtcgc acattcctgg accccagag ctgtggggac
ctgctgcagg
    1981 ctgtgcatct gttcgccaag gaactggatg cgaaaagcgt cacgctggag
aggagccttg
    2041 gaggagggcg gtttggggag ctgtgctgtg gctgcttgca gctccccggt
cgccaggagc
    2101 tgctcgtagc cgtgcatatg ctgagggaca gcgcctccga ctcacagagg
ctcggcttcc
    2161 tggccgaggc cctcacgctg ggccagtttg accatagcca catcgtgcgg
ctggagggcg
    2221 ttgttacccg aggaagcacc ttgatgattg tcaccgagta catgagccat
gggccctgg
    2281 acggcttcct caggcggcac gaggggcagc tggtggctgg gcaactgatg
gggttgctgc
    2341 ctgggctggc atcagccatg aagtatctgt cagagatggg ctacgttcac
cggggcctgg
    2401 cagctggcca tgtgctggtc agcagcgacc ttgtctgcaa gatctctggc
ttcgggcggg
    2461 gcccccggga ccgatcagag gctgtctaca ccactatgag tggccggagc
ccagcgctat
    2521 gggccgctcc cgagacactt cagtttggcc acttcagctc tgccagtgac
gtgtggagct
    2581 tcggcatcat catgtgggag gtgatggcct ttggggagcg gccttactgg
gacatgtctg
    2641 gccaagacgt gatcaaggct gtggaggatg gcttccggct gccacccccc
aggaactgtc
    2701 ctaaccttct gcaccgacta atgctcgact gctggcagaa ggacccaagt
gagcggccca
    2761 ggttctccca gatccacagc atcctgagca agatggtgca ggacccagag
cccccaagt
    2821 gtgccctgac tacctgtccc aggcctccca cccactagc ggaccgtgcc
ttctccacct
    2881 tcccctcctt tggctctgtg ggcgcgtggc tggaggccct ggacctgtgc
cgctacaagg
    2941 acagcttcgc ggctgctggc tatggagcc tggaggccgt ggccgagatg
actgcccagg
    3001 acctggtgag cctaggcatc tctttggctg aacatcgaga ggccctcctc
agcgggatca
    3061 gcgccctgca ggcacgagtg ctccagctgc agggccaggg ggtgcaggtg
tgagtggacc
    3121 ccattcttcc aaggcaggac tccggtgggg gtccagtccc ccagccctgc
ccaaggaccg
    3181 tggcaagctg cgctccagca gtgtgggagg gagcgctctc ttcctctgct
tgggcccaga
    3241 tctggtgggg ccacagcttc cccgttttca ctgcctgccc ctcccatttc
cacgagtctg
    3301 aacgccttgg ctaactcagt gcccctgaaa agaggttcaa atccctaggg
aggaccctg
    3361 agataacagc aggaggaaat tcggggtctc agagaaaagc tggggcaggg
atggaggga
    3421 agacagtggg ttgagattgc cctggctcat gccctactgc catttgtacc
cactggggc
```

Figure 2(cont.)

SEQ ID No. 7 (cont.)

```
3481 tgggcctac ccgtggggt gttcctttt cccacagac cattgaccag
tcagacagcg
3541 tgggtcctgg ggggtcttc ttctacctgg cagtgactgc agctgcctgg
tggctcaggc
3601 gtgggggct gggccagagg tgcatccacc tcagctcct gtgccttggc
aggggctgac
3661 tggacactgg ccaaggctca ggcaggcaaa gatggtgctg agctcagggg
ctgatacca
3721 agagccctag actcaggatc tggtttctgt gtcccctgc cttgggctga
cagttcaggg
3781 tgaggccaaa agtcctggcc aggccgggcc atgagaggcc ctggtgctcc
ctggggcccc
3841 atgaggccct cgtgtgcatt cctttatga acttagtggc caggacatct
gggaaaagca
3901 taaagggcca tgttatctcc ccagggaccc aagagctttt ctctccagcc
atggggaggg
3961 tgaagaggag actcagagat gggtcctctc tctcaaacag gctggtctaa
ccccagtgt
4021 acagatgggg gaaactgagg ccaagtgagg agtcaggagc agagctgagg
tcagaaccca
4081 atccaggggt aaggctggct ctggggagag agtccttggt cctgccctat
ggcaccacca
4141 cttccctgta cagcccttgg ggactctaga ggcgactccc ctccagccag
ctccgtgcct
4201 tgggcactac ccagccttcc atggagcccc tccctgctct gactttgaag
agccctggca
4261 gaagtggttg tgctgagccc accgtggagt tccttatcca caagggccc
cgggaatggt
4321 ggggcccagt atgccagagc tttcgtaggg tggcaggaag gcagctggat
ctcagcaggg
4381 ccacaggac tgagtttgtt taggccgccc gtgacacttg tctgctctgc
ttggctgtgt
4441 gttggtgggg tgggatgggg cgggaaagag gagacaagag gtaaagatga
aaaagacaca
4501 cagcctgccc ttggggggct cagactagac caggagaaga gctcaggtac
caagaagtaa
4561 ttccaggca ccatccacag tgcccagggc ccccaggag ccctctgggt
cagtgggtag
4621 gtgggctgga gggagata gccactctct taatgtgtga agttgagatg
taagttgaac
4681 agggccttgc aggtgggaaa gggaaggttc tttccttggg gtgggtggag
ttttcggcag
4741 gcaagatggc aggcctcgga caaaaggagt ccatgcagag aggctagcat
gagaaagagc
4801 ccagaggcgg gaaggtgcag tgcctctttg cagagcaccc agaggtgggg
gacagtgact
4861 cacagaggtg cctttggcct taccctgcca gcagcagctc cctgtctctt
ggaatctccc
4921 cccagccccc tgcctccctg tctctgagc acctgcccca gctcagtgac
tctgggggta
4981 ctgggagac caagatgttg ctaccacctt agtcagggtt gggggagccc
ccggccaggt
5041 gccctccagg atccgccttc cccacccctc ctgggaagcc tggaccagca
tccttcttg
5101 ggtggatgga gcctcgtcct catctccagc tacatcagtc attctctgca
gggcaaaatc
5161 tcctccccct accccagctg tttctgcaga agggcccctg gctgtgttgg
caggacttcg
```

Figure 2(cont.)

SEQ ID No. 7 (cont.)

```
    5221 gtgtccaggg tagatctccc ctccactgag gagtgaggtc ccagaatcct
gttgggtccc
    5281 aggcctcagc cctgcacaga tgtgatgtgg ggcgatggct ctctgggaac
cctctacaga
    5341 tctattttta tatggaactt gttcactgga cagaggtggc ctgcaagccc
ccattaccct
    5401 ggtctgagct caccctggga gggagggggc cagtcggagg gggttccttc
tggagatgtt
    5461 tttatatttc ttgggttctc tatgcaggat aataaaaact tgtctgtgat
aaaaaaaaaa
    5521 aaaaaa
```

METHODS FOR TREATING CANCER USING EPHRIN TYPE-A RECEPTOR 10 ANTIBODIES CONJUGATED TO CYTOTOXIC AGENTS

CROSS REFERENCES TO RELATED APPLICATIONS

This application is a United States National Stage Application filed under 35 U.S.C. §371 of PCT application Ser. No. PCT/IB2008/003634, filed Dec. 24, 2008, which claims the benefit and priority to U.S. Provisional Application Ser. No. 61/008,775, filed Dec. 24, 2007 under U.S.C. §119(e), all of which is incorporated by reference in their entirety herein.

INTRODUCTION

The present invention relates to the identification of membrane protein associated with bladder cancer, breast cancer, colorectal cancer, head and neck cancer, kidney cancer, lung cancer and pancreatic cancer which has utility as a marker for bladder cancer, breast cancer, colorectal cancer, head and neck cancer, kidney cancer, lung cancer and pancreatic cancer metastases and which also forms a biological target against which therapeutic antibodies (or other affinity reagents) or other pharmaceutical agents can be made, formulations/compositions comprising said protein/polypeptide, use of said protein/polypeptide or a composition comprising same in therapy, antibodies for use in therapy, compositions comprising a therapeutic antibody against a relevant polypeptide or a combination of antibodies and use of same in therapy. The invention also extends to use of the relevant protein, fragments thereof or antibodies directed against the same for diagnosis of one or more of bladder cancer, breast cancer, colorectal cancer, head and neck cancer, kidney cancer, lung cancer and pancreatic cancer and kits comprising said protein, fragments or antibodies and use of said kits in methods of diagnosis.

BACKGROUND OF THE INVENTION

Bladder Cancer

In the United States, bladder cancer is the fourth most common type of cancer in men and the ninth most common cancer in women. More than 51,000 men and 17,000 women are diagnosed with bladder cancer each year, with around 14,000 deaths in total. One reason for its higher incidence in men is that the androgen receptor, which is much more active in men than in women, plays a major part in the development of the cancer.

Incidence of bladder cancer increases with age. People over the age of 70 develop the disease 2 to 3 times more often than those aged 55-69 and 15 to 20 times more often than those aged 30-54. Bladder cancer is 2 to 3 times more common in men. Smoking is a major contributory factor, accounting for up to 65 percent of cases in men and 30 percent of cases in women in developed countries.

It has been estimated that approximately US$2 billion is spent in the United States on treating bladder cancer. The NCI's investment in bladder cancer research has increased from US$19.1 million in 2000 to an estimated US$34.8 million in 2005.

Bladder Cancer Diagnosis

Most patients when first diagnosed with bladder cancer have their cancer confined to the bladder (74%). In 19% of the cases, the cancer has spread to nearby tissues outside the bladder and in 3% it has spread to distant sites.

Bladder cancer can be diagnosed using cystoscopy, biopsy, urine cytology and imaging tests such as an intravenous pyelogram (IVP), computed tomography (CT) scan, magnetic resonance imaging (MRI) scan or ultrasound.

Bladder Cancer Staging

Bladder cancer is staged using the American Joint Committee on Cancer (AJCC) TNM system—stage I-IV.

Bladder Cancer Treatment

The main types of treatment for bladder cancer are surgery, radiation therapy, immunotherapy and chemotherapy. Surgery, alone or combined with other treatments, is used in more than 90% of cases. For early stage or superficial bladder cancer, a transurethral resection (TUR) is most common. About 70-80% of patients have superficial cancer when first diagnosed. When the bladder cancer is invasive, a cystectomy is sometimes necessary. An alternative approach for locally advanced bladder cancer can be a TUR along with radiation therapy and chemotherapy.

Bacillus Calmette-Guerin (BCG) can be used as immunotherapy for treating low-stage bladder cancer.

Neoadjuvant or adjuvant chemotherapy can be used in the treatment of bladder cancer. Mitomycin and thiotepa are the drugs most often used for intravesical chemotherapy. Systemic chemotherapy combinations used to treat bladder cancer include M-VAC (methotrexate, vinblastine, doxorubicin and cisplatin), MCV (methotrexate, cisplatin and vinblastine) and GemCIS (gemcitabine and cisplatin).

External beam radiation therapy or local or interstitial radiation therapy can be combined with chemotherapy after surgery.

Bladder Cancer Survival by Stage

| Stage | Relative 5-year Survival Rate |
|---|---|
| 0 | 95% |
| I | 85% |
| II | 55% |
| III | 38% |
| IV | 16% |

Breast Cancer

Globally, breast cancer is both the most common cancer (10% of all cancer cases) and the leading cause of cancer death (6% of cancer deaths) in women. Global incidence of breast cancer is over 1 million cases per year, with about 400,000 deaths. Women in North America have the highest rate of breast cancer in the world (over 200,000 new cases per year, with about 40,000 deaths). The chance of developing invasive breast cancer at some time in a woman's life is about 1 in 8. Breast cancer incidence increases with age, rising sharply after age 40. In the USA, about 77% of invasive breast cancers occur in women over age 50. It has been estimated that approximately US$8.1 billion is spent in the USA each year on treating breast cancer.

Breast Cancer Diagnosis

Early diagnosis improves the likelihood that treatment will be successful. Screening methods such as mammograms, clinical breast examinations and breast self-examinations are useful in detecting breast cancer. Current diagnostic methods include breast ultrasound, ductogram, full-field digital mammography (FFDM), scintimammography and MRI. A biopsy (fine needle aspiration biopsy, core biopsy or surgical biopsy) is then performed to confirm the presence of breast cancer. Imaging tests such as a chest x-ray, bone scan, CT, MRI and PET are used to detect if the breast cancer has spread.

Breast Cancer Staging

Breast cancer is staged using the American Joint Committee on Cancer (AJCC) TNM system—Stage 0-Stage IV. Ductal carcinoma in situ (DCIS), a non-invasive cancer which accounts for 20% of new breast cancer cases is Stage 0. Nearly all women diagnosed at this early stage of breast cancer can be cured. Infiltrating (invasive) ductal carcinoma (IDC), which accounts for 80% of invasive breast cancer and infiltrating (invasive) lobular carcinoma (ILC), which accounts for 5% of invasive breast cancers are more severe Stage I-IV cancers and can metastasize.

Breast Cancer Treatment

Breast-conserving surgery (lumpectomy) or mastectomy are the usual treatments for breast cancer. For stage I or II breast cancer, breast-conserving surgery is as effective as mastectomy. Patients can then undergo reconstructive surgery. Axillary lymph node sampling and removal or sentinel lymph node biopsy (SLNB) is performed to see if the cancer has spread to the lymph nodes.

Neoadjuvant chemotherapy can be given before surgery to shrink large cancers. Adjuvant chemotherapy after surgery reduces the risk of breast cancer recurrence. Chemotherapy can also be used as the main treatment for women whose cancer has spread outside the breast and underarm area. Chemotherapeutic agents used include anthracyclines (e.g. methotrexate, fluorouracil, doxorubicin, epirubicin), taxanes (e.g. paclitaxel, docetaxel, vinorelbine) and alkylating agents (e.g. cyclophosphamide).

Radiation therapy (usually external beam radiation but sometimes brachytherapy) is given once chemotherapy is complete.

Hormone therapy with selective oestrogen receptor modulators (e.g. tamoxifen) can be given to women with oestrogen receptor positive breast cancers. Taking tamoxifen after surgery for 5 years can reduce recurrence by about 50% in women with early breast cancer. Aromatase inhibitors such as exemestane, letrozole or anastrozole can also be used.

Women with HER2 positive cancers (about ⅓ of breast cancers) can be given biological response modifiers such as trastuzumab (Herceptin). Clinical trials have shown that adding trastuzumab to chemotherapy lowers the recurrence rate and death rate over chemotherapy alone after surgery in women with HER2 positive early breast cancers.

Breast Cancer Survival by Stage

Patients diagnosed with breast cancer between 1995 and 1998 had a 5 year relative survival rate of 100% for stage 0 and I, 92% for stage IIA, 81% for stage IIB, 67% for stage IIIA, 54% for stage IIIB and 20% for stage IV.

Colorectal Cancer

Colorectal cancer (CRC) is one of the leading causes of cancer-related morbidity and mortality, responsible for an estimated half a million deaths per year, mostly in Western, well developed countries. In these territories, CRC is the third most common malignancy (estimated number of new cases per annum in USA and EU is approximately 350,000 per year). Estimated healthcare costs related to treatment for colorectal cancer in the United States are more than $8 billion.

Colorectal Cancer Diagnosis

Today, the faecal occult blood test and colonoscopy, a highly invasive procedure, are the most frequently used screening and diagnostic methods for colorectal cancer. Other diagnostic tools include Flexible Sigmoidoscopy (allowing the observation of only about half of the colon) and Double Contrast Barium Enema (DCBE, to obtain X-ray images).

Colorectal Cancer Staging

CRC has four distinct stages: patients with stage I disease have a five-year survival rate of >90%, while those with metastatic stage IV disease have a <5% survival rate according to the US National Institutes of Health (NIH).

Colorectal Cancer Treatment

Once CRC has been diagnosed, the correct treatment needs to be selected. Surgery is usually the main treatment for rectal cancer, although radiation and chemotherapy will often be given before surgery. Possible side effects of surgery include bleeding from the surgery, deep vein thrombosis and damage to nearby organs during the operation.

Currently, 60 percent of colorectal cancer patients receive chemotherapy to treat their disease; however, this form of treatment only benefits a few percent of the population, while carrying with it high risks of toxicity, thus demonstrating a need to better define the patient selection criteria.

Colorectal cancer has a 30 to 40 percent recurrence rate within an average of 18 months after primary diagnosis. As with all cancers, the earlier it is detected the more likely it can be cured, especially as pathologists have recognised that the majority of CRC tumours develop in a series of well-defined stages from benign adenomas.

Colon Cancer Survival by Stage

| Stage | Survival Rate |
| --- | --- |
| I | 93% |
| IIA | 85% |
| IIB | 72% |
| IIIA | 83% |
| IIIB | 64% |
| IIIC | 44% |
| IV | 8% |

Head and Neck Cancer

The term head and neck cancer refers to a group of biologically similar cancers originating from the upper aerodigestive tract, including the lip, oral cavity (mouth), nasal cavity, paranasal sinuses, pharynx, and larynx. Most head and neck cancers are squamous cell carcinomas, originating from the mucosal lining (epithelium) of these regions. Head and neck cancers often spread to the lymph nodes of the neck, and this is often the first manifestation of the disease at the time of diagnosis.

The number of new cases of head and neck cancers in the United States was 40,490 in 2006, accounting for about 3% of adult malignancies. 11,170 patients died of their disease in 2006. The worldwide incidence exceeds half a million cases annually. 85% of head and neck cancers are linked to tobacco use. In North America and Europe, the tumours usually arise from the oral cavity, oropharynx, or larynx, whereas nasopharyngeal cancer is more common in the Mediterranean countries and in the Far East. In Southeast China and Taiwan, head and neck cancer, specifically nasopharyngeal cancer is the most common cause of death in young men. African Americans are disproportionately affected by head and neck cancer, with younger ages of incidence, increased mortality, and more advanced disease at presentation.

Head and Neck Cancer Diagnosis

Head and neck cancer is diagnosed using a combination of tests which can include a physical examination, endoscopy, X-ray, computed tomography (CT) scan, magnetic resonance imaging (MRI) scan, PET scan and a biopsy. Early signs of head and neck cancer are often not detected and the majority of head and neck cancer patients present with advanced disease and often have secondary tumours.

Head and Neck Cancer Staging

Head and neck cancer is staged using the American Joint Committee on Cancer (AJCC) TNM system—stage I-IV. The 5-year survival for all stages of head and neck cancer is 35-50%, due, in part, to late presentation. Stage I and II survival rates range from 40-95% and stage III and IV survival rates range from 0-50%. It is predicted that at least one third of patients with head and neck cancer will ultimately die as a result of their disease. The 5-year mortality rate has not altered significantly in the last few decades, despite advances in treatment modalities.

Head and Neck Cancer Treatment

Surgery and radiation therapy are the primary modalities of therapy, often in combination. Chemotherapy can be used as an induction therapy or as an adjuvant to radiation therapy, with or without surgery.

Kidney Cancer

Kidney cancer accounts for about 1.9% of cancer cases globally and 1.5% of deaths. Global incidence of kidney cancer is around 208,000 cases, with over 100,000 deaths. The incidence of kidney cancer is much higher in developed countries, being the sixth most common form of cancer in Western Europe. Around 38,900 new cases of kidney cancer are diagnosed in the USA each year, with around 12,800 deaths. It is very uncommon under age 45, and its incidence is highest between the ages of 55 and 84. The rate of people developing kidney cancer has been increasing at about 1.5% per year but the death rate has not been increasing. Renal cell carcinoma accounts for more than 90% of malignant kidney tumours. It has been estimated that approximately US$1.9 billion is spent in the USA each year on treating kidney cancer.

Kidney Cancer Diagnosis

Many renal cell cancers are found at a late stage; they can become quite large without causing any pain or discomfort and there are no simple tests that can detect renal cell cancer early. About 25% of patients with renal cell carcinoma will already have metastatic spread of their cancer when they are diagnosed.

Renal cell cancer can often be diagnosed without the need for a biopsy using a CT scan, MRI, ultrasound, positron emission tomography (PET) scan, intravenous pyelogram (IVP) and/or angiography. Fine needle aspiration biopsy may however be valuable when imaging results are not conclusive enough to warrant removing a kidney.

Kidney Cancer Staging

Renal cell cancers are usually graded on a scale of 1-4. Renal cell cancer is also staged using the American Joint Committee on Cancer (AJCC) TNM system—stage I-IV. The University of California Los Angeles Integrated Staging System can also be used, which divides patients without any tumour spread into three groups—low risk, intermediate risk and high risk. The 5-year cancer-specific survival for the low-risk group is 91%, for the intermediate-risk group is 80%, and for the high-risk group is 55%. Patients with tumour spread are also divided into three groups—low, intermediate and high risk. The 5-year cancer-specific survival for the low-risk group is 32%, for the intermediate-risk group 20% and for the high-risk group 0%.

Kidney Cancer Treatment

Surgery by radical nephrectomy (and sometimes regional lymphadenectomy), partial nephrectomy or laparoscopic nephrectomy is the main treatment for renal cell carcinoma. Renal cell carcinomas are not very sensitive to radiation so using radiation therapy before or after removing the cancer is not routinely recommended because studies have shown no improvement in survival rates.

Renal cell cancers are very resistant to present forms of chemotherapy. Some drugs, such as vinblastine, floxuridine, and 5-fluorouracil (5-FU) are mildly effective. A combination of 5-FU and gemcitabine has benefited some patients. A 5-FU-like drug, capecitabine, may also have some benefit.

Cytokines (interleukin-2 (IL-2) and interferon-alpha) have become one of the standard treatments for metastatic renal cell carcinoma. These cause the cancers to shrink to less than half their original size in about 10% to 20% of patients. Patients who respond to IL-2 tend to have lasting responses. Recent research with a combination of IL-2, interferon, and chemotherapy (using 5-fluorouracil) is also promising and may offer a better chance of partial or complete remission. Cytokine therapy does have severe side affects however.

Sorafenib (Nexavar), Sunitinib (Sutent) and Bevacizumab (Avastin) are other drugs which may also be effective against renal cell cancer.

Kidney Cancer Survival by Stage

| T stage cancer | 5/10-year cancer-specific survival |
|---|---|
| T1 | 95%/91% |
| T2 | 80%/70% |
| T3a | 66%/53% |
| T3b | 52%/43% |
| T3c | 43%/42% |

Lung Cancer

Lung cancer is the most common form of cancer worldwide (accounting for about 12% of cancer cases) and the main cause of death from cancer (accounting for about 18% of deaths).

Global incidence of lung cancer is over 1,300,000 per year, with the number of deaths over 1,100,000. In the USA, there are about 170,000 new cases per year (about 13% of all cancers), with about 160,000 deaths (about 28% of cancer deaths). Lung cancer is much more prevalent among men than women. Nearly 70% of people diagnosed with lung cancer are older than 65; fewer than 3% of all cases are found in people under the age of 45. Around 15% of all lung cancers are small cell type (SCLC), which tend to spread widely through the body, while the remaining 85% are non-small cell (NSCLC). It has been estimated that approximately US$9.6 billion is spent in the USA each year on treating lung cancer.

Lung Cancer Diagnosis

Lung cancer is a life-threatening disease because it often metastasises even before it can be detected on a chest x-ray. Usually symptoms of lung cancer do not appear until the disease is in an advanced stage. So far, there is no screening test that has been shown to improve a person's chance for a cure. Imaging tests such as a chest x-ray, CT scan, MRI scan or PET scan may be used to detect lung cancer. Tests to confirm the diagnosis are then performed and include sputum cytology, needle biopsy, bronchoscopy, endobronchial ultrasound and complete blood count (CBC).

Lung Cancer Staging

Nearly 60% of people diagnosed with lung cancer die within one year of diagnosis; 75% die within 2 years. The 5-year survival rate for people diagnosed with NSCLC is about 15%; for SCLC the 5-year survival rate is about 6%. NSCLC is staged using the American Joint Committee on Cancer (AJCC) TNM system—Stage 0-Stage IV. The 5-year survival rates by stage are as follows: stage I: 47%; stage II; 26%; stage III: 8% and stage IV: 2%. SCLC has a 2-stage system—limited stage and extensive stage. About two thirds of SCLC patients have extensive disease at diagnosis. If SCLC is found very early and is localised to the lung alone, the 5-year survival rate is around 21%, but only 6% of patients fall into this category. Where the cancer has spread, the 5-year survival is around 11%. For patients with extensive disease, the 5-year survival is just 2%.

Lung Cancer Treatment

Surgery is the only reliable method to cure NSCLC. Types of surgery include lobectomy, pneumonectomy, segmentectomy and video-assisted thoracic surgery (for small tumours).

External beam radiation therapy is sometimes used as the primary treatment, especially if the patient's health is too poor to undergo surgery. Radiation therapy can also be used after surgery. Chemotherapy may be given as the primary treatment or as an adjuvant to surgery. Targeted therapy using epidermal growth factor receptor (EGFR) antagonists such as gefitinib or erlotinib can also be given after other treatments have failed. Antiangiogenic drugs, such as bevacizumab, have been found to prolong survival of patients with advanced lung cancer. Photodynamic therapy is also being researched as a treatment for lung cancer.

The main treatment for SCLC is chemotherapy, either alone or in combination with external beam radiation therapy and very rarely, surgery.

Chemotherapeutic agents used for NSCLC and SCLC include cisplatin, carboplatin, mitomycin C, ifosfamide, vinblastine, gemcitabine, etoposide, vinorelbine, paclitaxel, docetaxel and irinotecan.

Pancreatic Cancer

Pancreatic cancer is a very difficult cancer to detect and the prognosis for patients is usually very poor. The number of new cases and deaths per year is almost equal. Global incidence of pancreatic cancer is approximately 230,000 cases (about 2% of all cancer cases), with about 225,000 deaths (3.4% of cancer deaths) per year. It is much more prevalent in the developed world. In the USA, there are about 34,000 new cases per year, with about 32,000 deaths. It has been estimated that approximately US$1.5 billion is spent in the USA each year on treating pancreatic cancer.

Pancreatic Cancer Diagnosis

Pancreatic cancer is very difficult to detect and very few pancreatic cancers are found early. Patients usually have no symptoms until the cancer has spread to other organs. There are currently no blood tests or easily available screening tests that can accurately detect early cancers of the pancreas. An endoscopic ultrasound followed by a biopsy is the best way to diagnose pancreatic cancer. Other detection methods include CT, CT-guided needle biopsy, PET, ultrasonography and MRI. Blood levels of CA 19-9 and carcinoembryonic antigen (CEA) may be elevated but by the time blood levels are high enough to be detected, the cancer is no longer in its early stages.

Pancreatic Cancer Staging

Pancreatic cancer has four stages, stage I to stage IV according to the American Joint Committee on Cancer (AJCC) TNM system. Pancreatic cancer is also divided into resectable, locally advanced (unresectable) and metastatic cancer. For patients with advanced cancers, the overall survival rate is <1% at 5 years with most patients dying within 1 year.

Pancreatic Cancer Treatment

Surgery is the only method of curing pancreatic cancer. About 10% of pancreatic cancers are contained entirely within the pancreas at the time of diagnosis and attempts to remove the entire cancer by surgery may be successful in some of these patients. The 5-year survival for those undergoing surgery with the intent of completely removing the cancer is about 20%. Potentially curative surgery, usually by pancreaticoduodenectomy (Whipple procedure), is used when it may be possible to remove all of the cancer. Palliative surgery may be performed if the tumour is too widespread to be completely removed. Removing only part of the cancer does not allow patients to live longer. Pancreatic cancer surgery is difficult to perform with a high likelihood of complications.

External beam radiation therapy combined with chemotherapy can be given before or after surgery and can also be given to patients whose tumours are too widespread to be removed by surgery. The main chemotherapeutic agents which are used are gemcitabine and 5-fluorouracil. Targeted therapy using drugs such as erlotinib and cetuximab may be of benefit to patients with advanced pancreatic cancer.

Therapeutic Challenges

The major challenges in treatment of the above mentioned cancers are to improve early detection rates, to find new non-invasive markers that can be used to follow disease progression and identify relapse, and to find improved and less toxic therapies, especially for more advanced disease where 5 year survival is still poor. There is a great need to identify targets which are more specific to the cancer cells, e.g. ones which are expressed on the surface of the tumour cells so that they can be attacked by promising new approaches like immunotherapeutics and targeted toxins.

SUMMARY OF THE INVENTION

The present invention provides methods and compositions for screening, diagnosis, prognosis and therapy of bladder cancer, breast cancer, colorectal cancer, head and neck cancer, kidney cancer, lung cancer or pancreatic cancer, for bladder cancer, breast cancer, colorectal cancer, head and neck cancer, kidney cancer, lung cancer or pancreatic cancer patients' stratification, for monitoring the effectiveness of bladder cancer, breast cancer, colorectal cancer, head and neck cancer, kidney cancer, lung cancer or pancreatic cancer treatment, and for drug development for treatment of bladder cancer, breast cancer, colorectal cancer, head and neck cancer, kidney cancer, lung cancer or pancreatic cancer.

We have used mass spectrometry to identify peptides generated by tagging with iTRAQ reagents and tryptic digest of membrane proteins extracted from colorectal cancer, kidney cancer or lung cancer tissue samples. Peptide sequences were compared to existing protein and cDNA databases and the corresponding gene sequences identified. Immunohistochemistry experiments were conducted and strong staining was observed in bladder cancer, breast cancer, colorectal cancer, head and neck cancer, kidney cancer, lung cancer and pancreatic cancer samples. The protein of the invention has not been previously reported to originate from or be found in bladder cancer, breast cancer, colorectal cancer, head and neck cancer, kidney cancer, lung cancer or pancreatic cancer cell membranes and represents a protein of new diagnostic and therapeutic value.

A first aspect of the invention is an agent capable of specific binding to Ephrin type-A receptor 10, or a fragment thereof, or a hybridising agent capable of hybridizing to nucleic acid encoding Ephrin type-A receptor 10, or fragment thereof, or an agent capable of detecting the activity of Ephrin type-A receptor 10 for use in treating, screening for, detecting and/or diagnosing disease, such as cancer, and especially bladder cancer, breast cancer, colorectal cancer, head and neck cancer, kidney cancer, lung cancer or pancreatic cancer.

Another aspect of the invention is Ephrin type-A receptor 10, or a fragment thereof for use in treating, screening for, detecting and/or diagnosing disease such as cancer, and especially bladder cancer, breast cancer, colorectal cancer, head and neck cancer, kidney cancer, lung cancer or pancreatic cancer.

Another aspect of the invention is an affinity reagent capable of specific binding to Ephrin type-A receptor 10 or a fragment thereof, for example an affinity reagent which contains or is conjugated to a detectable label or contains or is conjugated to a therapeutic moiety such as a cytotoxic moiety. The affinity reagent may, for example, be an antibody.

In some embodiments, the antibody of the present invention is selected from the group consisting of: a whole antibody, an antibody fragment, a humanized antibody, a single chain antibody, an immunoconjugate, a defucosylated antibody, and a bispecific antibody. The antibody fragment may be selected from the group consisting of: a UniBody, a domain antibody, and a Nanobody. In some embodiments, the immunoconjugates of the invention comprise a therapeutic agent. In another aspect of the invention, the therapeutic agent is a cytotoxin or a radioactive isotope.

In some embodiments, the antibody of the present invention is selected from the group consisting of: an Affibody, a DARPin, an Anticalin, an Avimer, a Versabody, and a Duocalin.

Another aspect of the invention is a hybridizing agent capable of hybridizing to nucleic acid encoding Ephrin type-A receptor 10, or fragment thereof, for example, a hybridizing agent which contains or is conjugated to a detectable label. One example of a hybridizing agent is an inhibitory RNA (RNAi). Other examples include anti-sense oligonucleotides and ribozymes.

The invention also provides a kit containing Ephrin type-A receptor 10 and/or one or more fragments thereof or containing one or more aforementioned affinity reagents and/or hybridizing agents or containing one or more agents capable of detecting the activity of Ephrin type-A receptor 10 together with instructions for their use in an aforementioned method. The kit may further contain reagents capable of detecting and reporting the binding of said affinity reagents and/or hybridizing agents to their binding partners.

Another aspect of the invention is a pharmaceutical composition comprising a therapeutically effective amount of an affinity reagent capable of specific binding to Ephrin type-A receptor 10 or a fragment thereof.

Another aspect of the invention is a pharmaceutically acceptable diluent or carrier and a pharmaceutical composition comprising one or more affinity reagents or hybridizing reagents as aforesaid and a pharmaceutically acceptable diluent or carrier.

In some embodiments, the present invention is a method for preparing an anti-Ephrin type-A receptor 10 antibody, said method comprising the steps of: obtaining a host cell that contains one or more nucleic acid molecules encoding the antibody of the invention; growing the host cell in a host cell culture; providing host cell culture conditions wherein the one or more nucleic acid molecules are expressed; and recovering the antibody from the host cell or from the host cell culture.

Other aspects of the invention are directed to methods of making the antibodies of the invention, comprising the steps of: immunizing a transgenic animal comprising human immunoglobulin genes with an Ephrin type-A receptor 10 peptide; recovering B-cells from said transgenic animal; making hybridomas from said B-cells; selecting hybridomas that express antibodies that bind Ephrin type-A receptor 10; and recovering said antibodies that bind Ephrin type-A receptor 10 from said selected hybridomas.

In other embodiments, the method of making anti-Ephrin type-A receptor 10 antibodies, comprises the steps of:

immunizing a transgenic animal comprising human immunoglobulin genes with an Ephrin type-A receptor 10 peptide;

recovering mRNA from the B cells of said transgenic animal;

converting said mRNA to cDNA;

expressing said cDNA in phages such that anti-Ephrin type-A receptor 10 antibodies encoded by said cDNA are presented on the surface of said phages;

selecting phages that present anti-Ephrin type-A receptor 10 antibodies;

recovering nucleic acid molecules from said selected phages that encode said anti-Ephrin type-A receptor 10 immunoglobulins;

expressing said recovered nucleic acid molecules in a host cell; and recovering antibodies from said host cell that bind Ephrin type-A receptor 10.

Another aspect of the invention provides use of an Ephrin type-A receptor 10 polypeptide, one or more immunogenic fragments or derivatives thereof for the treatment or prophylaxis of bladder cancer, breast cancer, colorectal cancer, head and neck cancer, kidney cancer, lung cancer or pancreatic cancer.

In another aspect the invention provides methods of treating bladder cancer, breast cancer, colorectal cancer, head and neck cancer, kidney cancer, lung cancer or pancreatic cancer, comprising administering to a patient a therapeutically effective amount of a compound that modulates (e.g. upregulates or downregulates) or complements the expression or the biological activity (or both) of the protein of the invention in patients having bladder cancer, breast cancer, colorectal cancer, head and neck cancer, kidney cancer, lung cancer or pancreatic cancer, in order to (a) prevent the onset or development of bladder cancer, breast cancer, colorectal cancer, head and neck cancer, kidney cancer, lung cancer or pancreatic cancer; (b) prevent the progression of bladder cancer, breast cancer, colorectal cancer, head and neck cancer, kidney cancer, lung cancer or pancreatic cancer; or (c) ameliorate the symptoms of bladder cancer, breast cancer, colorectal cancer, head and neck cancer, kidney cancer, lung cancer or pancreatic cancer.

According to another aspect of the invention we provide a method of detecting, diagnosing and/or screening for or monitoring the progression of bladder cancer, breast cancer, colorectal cancer, head and neck cancer, kidney cancer, lung cancer or pancreatic cancer or of monitoring the effect of an anti-bladder cancer, anti-breast cancer, anti-colorectal cancer, anti-head and neck cancer, anti-kidney cancer, anti-lung cancer or anti-pancreatic cancer drug or therapy in a subject which comprises detecting the presence or level of Ephrin type-A receptor 10, or one or more fragments thereof, or the presence or level of nucleic acid encoding Ephrin type-A receptor 10 or the presence or level of the activity of Ephrin type-A receptor 10 or which comprises detecting a change in the level thereof in said subject.

According to another aspect of the invention we provide a method of detecting, diagnosing and/or screening for bladder cancer, breast cancer, colorectal cancer, head and neck cancer, kidney cancer, lung cancer or pancreatic cancer in a candidate subject which comprises detecting the presence of Ephrin type-A receptor 10, or one or more fragments thereof, or the presence of nucleic acid encoding Ephrin type-A receptor 10 or the presence of the activity of Ephrin type-A receptor 10 in said candidate subject, in which either (a) the presence of an elevated level of Ephrin type-A receptor 10 or said one or more fragments thereof or an elevated level of nucleic acid, or complement thereof, encoding Ephrin type-A receptor 10 or the presence of an elevated level of Ephrin type-A receptor 10 activity in the candidate subject as compared with the level in a healthy subject or (b) the presence of a detectable level of Ephrin type-A receptor 10 or said one or more fragments thereof or a detectable level of nucleic acid encoding Ephrin type-A receptor 10 or the presence of a detectable level of Ephrin type-A receptor 10 activity in the candidate subject as compared with a corresponding undetectable level in a healthy subject indicates the presence of bladder cancer, breast cancer, colorectal cancer, head and neck cancer, kidney cancer, lung cancer or pancreatic cancer in said subject.

According to another aspect of the invention we provide a method of monitoring the progression of bladder cancer, breast cancer, colorectal cancer, head and neck cancer, kidney cancer, lung cancer or pancreatic cancer in a subject or of monitoring the effect of an anti-bladder cancer, anti-breast cancer, anti-colorectal cancer, anti-head and neck cancer, anti-kidney cancer, anti-lung cancer or anti-pancreatic cancer drug or therapy which comprises detecting the presence of Ephrin type-A receptor 10, or one or more fragments thereof, or the presence of nucleic acid encoding Ephrin type-A receptor 10 or the presence of the activity of Ephrin type-A receptor 10 in said candidate subject at a first time point and at a later time point, the presence of an elevated or lowered level of Ephrin type-A receptor 10 or said one or more fragments thereof or an elevated or lowered level of nucleic acid encoding Ephrin type-A receptor 10 or the presence of an elevated or lowered level of Ephrin type-A receptor 10 activity in the subject at the later time point as compared with the level in the subject at said first time point, indicating the progression or regression of bladder cancer, breast cancer, colorectal cancer, head and neck cancer, kidney cancer, lung cancer or pancreatic cancer or indicating the effect or non-effect of an anti-bladder cancer, anti-breast cancer, anti-colorectal cancer, anti-head and neck cancer, anti-kidney cancer, anti-lung cancer or anti-pancreatic cancer drug or therapy in said subject.

The presence of Ephrin type-A receptor 10, or one or more fragments thereof, or the presence of nucleic acid encoding Ephrin type-A receptor 10 or the presence of the activity of Ephrin type-A receptor 10 may, for example, be detected by analysis of a biological sample obtained from said subject.

The method of invention may typically include the step of obtaining a biological sample for analysis from said subject.

The biological sample used can be from any source such as a serum sample or a tissue sample e.g. bladder, breast, colorectal, head and neck, kidney, lung or pancreatic tissue. For instance, when looking for evidence of metastatic bladder cancer, breast cancer, colorectal cancer, head and neck cancer, kidney cancer, lung cancer or pancreatic cancer, one would look at major sites of bladder cancer, breast cancer, colorectal cancer, head and neck cancer, kidney cancer, lung cancer or pancreatic cancer metastasis, e.g. the prostate, the uterus, the vagina, the bones, the liver or the lungs for bladder cancer; the liver, the lungs and bones for breast cancer; the liver, the peritoneal cavity, the pelvis, the retroperitoneum and the lungs for colorectal cancer; the lungs, the bones and the liver for head and neck cancer; the bones, the lungs and the liver for kidney cancer; the brain, the liver, the bones and adrenal glands for lung cancer; and the liver for pancreatic cancer.

Alternatively the presence of Ephrin type-A receptor 10, or one or more fragments thereof, or the presence of nucleic acid encoding Ephrin type-A receptor 10 or the presence of the activity of Ephrin type-A receptor 10 may be detected by analysis in situ.

In certain embodiments, methods of diagnosis described herein may be at least partly, or wholly, performed in vitro.

Suitably the presence of Ephrin type-A receptor 10, or one or more fragments thereof, or the presence of nucleic acid encoding Ephrin type-A receptor 10 or the presence of the activity of Ephrin type-A receptor 10 is detected quantitatively.

For example, quantitatively detecting may comprise:
(a) contacting a biological sample with an affinity reagent that is specific for Ephrin type-A receptor 10, said affinity reagent optionally being conjugated to a detectable label; and
(b) detecting whether binding has occurred between the affinity reagent and at least one species in the sample, said detection being performed either directly or indirectly.

Alternatively the presence of Ephrin type-A receptor 10, or one or more fragments thereof, or the presence of nucleic acid encoding Ephrin type-A receptor 10 or the presence of the activity of Ephrin type-A receptor 10 may be detected quantitatively by means involving use of an imaging technology.

In another embodiment, the method of the invention involves use of immunohistochemistry on tissue sections in order to determine the presence of Ephrin type-A receptor 10, or one or more fragments thereof, or the presence of nucleic acid encoding Ephrin type-A receptor 10 or the presence of the activity of Ephrin type-A receptor 10, and thereby to localise bladder cancer, breast cancer, colorectal cancer, head and neck cancer, kidney cancer, lung cancer or pancreatic cancer cells.

In one embodiment the presence of Ephrin type-A receptor 10 or one or more epitope-containing fragments thereof is detected, for example using an affinity reagent capable of specific binding to Ephrin type-A receptor 10 or one or more fragments thereof, such as an antibody.

In another embodiment the activity of Ephrin type-A receptor 10 is detected. Ephrin type-A receptor 10 is a receptor protein tyrosine kinase. The activity of Ephrin type-A receptor 10 is detected by measuring the phosphorylation of tyrosine, serine or threonine residues, preferably tyrosine, in response to the binding of a specific ligand. Preferably, the activity of Ephrin type-A receptor 10 is detected by measuring the phosphorylation of Ephrin type-A receptor 10 amino acid sequences in response to the binding of a specific ligand. Alternatively, one might measure the specific phosphorylation of an Ephrin type-A receptor 10-binding protein, preferably another member of the Eph family of receptor protein tyrosine kinases, in response to binding of a specific ligand to Ephrin type-A receptor 10. A description of the activities of the Eph family of receptor protein tyrosine kinases, and their respective naturally binding ligands, is contained in H. Surawska et al., *Cytokine & Growth Factor Reviews* 15:419-433, 2004.

According to another aspect of the invention there is provided a method of detecting, diagnosing and/or screening for or monitoring the progression of bladder cancer, breast cancer, colorectal cancer, head and neck cancer, kidney cancer, lung cancer or pancreatic cancer or of monitoring the effect of an anti-bladder cancer, anti-breast cancer, anti-colorectal cancer, anti-head and neck cancer, anti-kidney cancer, anti-lung cancer or anti-pancreatic cancer drug or therapy in a subject which comprises detecting the presence or level of antibodies capable of immunospecific binding to Ephrin type-A receptor 10, or one or more epitope-containing fragments thereof or which comprises detecting a change in the level thereof in said subject.

According to another aspect of the invention there is also provided a method of detecting, diagnosing and/or screening for bladder cancer, breast cancer, colorectal cancer, head and neck cancer, kidney cancer, lung cancer or pancreatic cancer in a subject which comprises detecting the presence of antibodies capable of immunospecific binding to Ephrin type-A receptor 10, or one or more epitope-containing fragments thereof in said subject, in which (a) the presence of an elevated level of antibodies capable of immunospecific binding to Ephrin type-A receptor 10 or said one or more epitope-containing fragments thereof in said subject as compared with the level in a healthy subject or (b) the presence of a detectable level of antibodies capable of immunospecific binding to Ephrin type-A receptor 10 or said one or more epitope-containing fragments thereof in said subject as compared with a corresponding undetectable level in a healthy subject indicates the presence of bladder cancer, breast cancer, colorectal cancer, head and neck cancer, kidney cancer, lung cancer or pancreatic cancer in said subject.

One particular method of detecting, diagnosing and/or screening for bladder cancer, breast cancer, colorectal cancer, head and neck cancer, kidney cancer, lung cancer or pancreatic cancer comprises:
(a) bringing into contact with a biological sample to be tested Ephrin type-A receptor 10, or one or more epitope-containing fragments thereof; and
(b) detecting the presence of antibodies in the subject capable of immunospecific binding to Ephrin type-A receptor 10, or one or more epitope-containing fragments thereof.

According to another aspect of the invention there is provided a method of monitoring the progression of bladder cancer, breast cancer, colorectal cancer, head and neck cancer, kidney cancer, lung cancer or pancreatic cancer or of monitoring the effect of an anti-bladder cancer, anti-breast cancer, anti-colorectal cancer, anti-head and neck cancer, anti-kidney cancer, anti-lung cancer or anti-pancreatic cancer drug or therapy in a subject which comprises detecting the presence of antibodies capable of immunospecific binding to Ephrin type-A receptor 10, or one or more epitope-containing fragments thereof in said subject at a first time point and at a later time point, the presence of an elevated or lowered level of antibodies capable of immunospecific binding to Ephrin type-A receptor 10, or one or more epitope-containing fragments thereof in said subject at the later time point as compared with the level in said subject at said first time point, indicating the progression or regression of bladder cancer, breast cancer, colorectal cancer, head and neck cancer, kidney cancer, lung cancer or pancreatic cancer or the effect or non-effect of an anti-bladder cancer, anti-breast cancer, anti-colorectal cancer, anti-head and neck cancer, anti-kidney cancer, anti-lung cancer or anti-pancreatic cancer drug or therapy in said subject.

The presence of antibodies capable of immunospecific binding to Ephrin type-A receptor 10, or one or more epitope-containing fragments thereof is typically detected by analysis of a biological sample obtained from said subject (exemplary biological samples are mentioned above, e.g. the sample is a sample of bladder, breast, colorectal, head and neck, kidney, lung or pancreatic tissue, or else a sample of blood or saliva).

The method typically includes the step of obtaining said biological sample for analysis from said subject.

The antibodies that may be detected include IgA, IgM and IgG antibodies.

In any of the above methods, the level that may be detected in the candidate subject who has bladder cancer, breast cancer, colorectal cancer, head and neck cancer, kidney cancer, lung cancer or pancreatic cancer is 2 or more fold higher than the level in the healthy subject.

In one embodiment the cancer to be detected, prevented or treated is bladder cancer.

In another embodiment the cancer to be detected, prevented or treated is breast cancer.

In another embodiment the cancer to be detected, prevented or treated is colorectal cancer.

In another embodiment the cancer to be detected, prevented or treated is head and neck cancer.

In another embodiment the cancer to be detected, prevented or treated is kidney cancer.

In another embodiment the cancer to be detected, prevented or treated is lung cancer.

In another embodiment the cancer to be detected, prevented or treated is pancreatic cancer.

Other aspects of the present invention are set out below and in the claims herein.

BRIEF DESCRIPTION OF THE FIGURES

FIG. 1 shows the amino acid sequence of the protein of the invention [SEQ ID Nos. 1-6]. The tryptic peptides detected experimentally by mass spectrometry are highlighted—mass match peptides are shown in bold, tandem peptides are underlined.

FIG. 2 shows the nucleic acid sequence [SEQ ID No. 7].

DETAILED DESCRIPTION OF THE INVENTION

The invention described in detail below encompasses the administration of therapeutic compositions to a mammalian subject to treat or prevent bladder cancer, breast cancer, colorectal cancer, head and neck cancer, kidney cancer, lung cancer or pancreatic cancer. The invention also provides methods and compositions for clinical screening, diagnosis and prognosis of bladder cancer, breast cancer, colorectal cancer, head and neck cancer, kidney cancer, lung cancer or pancreatic cancer in a mammalian subject for identifying patients most likely to respond to a particular therapeutic treatment, for monitoring the results of bladder cancer, breast cancer, colorectal cancer, head and neck cancer, kidney cancer, lung cancer or pancreatic cancer therapy, for drug screening and drug development.

In one aspect the invention provides an agent capable of specific binding to Ephrin type-A receptor 10, or a fragment thereof, or a hybridising agent capable of hybridizing to nucleic acid encoding Ephrin type-A receptor 10 or an agent capable of detecting the activity of Ephrin type-A receptor 10 for use in treating, screening for, detecting and/or diagnosing disease, such as cancer, and especially bladder cancer, breast cancer, colorectal cancer, head and neck cancer, kidney cancer, lung cancer or pancreatic cancer.

Another aspect of the invention is an affinity reagent capable of specific binding to Ephrin type-A receptor 10 or a fragment thereof, for example an affinity reagent which contains or is conjugated to a detectable label or contains or is conjugated to a therapeutic moiety such as a cytotoxic moiety. The affinity reagent may, for example, be an antibody.

Another aspect of the invention is a pharmaceutical composition comprising a therapeutically effective amount of an affinity reagent capable of specific binding to Ephrin type-A receptor 10 or a fragment thereof.

In another aspect the invention provides use of an Ephrin type-A receptor 10 polypeptide, or one or more fragments or derivatives thereof, for the treatment or prophylaxis of bladder cancer, breast cancer, colorectal cancer, head and neck cancer, kidney cancer, lung cancer or pancreatic cancer.

The invention also provides use of an Ephrin type-A receptor 10 polypeptide, one or more fragments or derivatives thereof in the manufacture of a medicament for the treatment or prophylaxis of bladder cancer, breast cancer, colorectal cancer, head and neck cancer, kidney cancer, lung cancer or pancreatic cancer.

In one aspect there is provided a method of treatment comprising administering a therapeutically effective amount of an Ephrin type-A receptor 10 polypeptide, one or more fragments or derivatives thereof, or one or more fragments or derivatives thereof, for the treatment or prophylaxis of bladder cancer, breast cancer, colorectal cancer, head and neck cancer, kidney cancer, lung cancer or pancreatic cancer.

The invention further provides a method for the treatment or prophylaxis of bladder cancer, breast cancer, colorectal cancer, head and neck cancer, kidney cancer, lung cancer or pancreatic cancer in a subject, or of vaccinating a subject against bladder cancer, breast cancer, colorectal cancer, head and neck cancer, kidney cancer, lung cancer or pancreatic cancer, which comprises the step of administering to the subject an effective amount of an Ephrin type-A receptor 10 polypeptide and/or one or more antigenic or immunogenic fragments thereof, for example as a vaccine.

The mammalian subject may be a non-human mammal, but is preferably human, more preferably a human adult, i.e. a human subject at least 21 (more preferably at least 35, at least 50, at least 60, at least 70, or at least 80) years old.

In one aspect there is provided a composition capable of eliciting an immune response in a subject, which composition comprises an Ephrin type-A receptor 10 polypeptide and/or one or more antigenic or immunogenic fragments thereof, and one or more suitable adjuvants (suitable adjuvants are discussed below).

The composition capable of eliciting an immune response may for example be provided as a vaccine comprising an Ephrin type-A receptor 10 polypeptide or derivatives thereof, and/or one or more antigenic or immunogenic fragments thereof.

For clarity of disclosure, and not by way of limitation, the invention will be described with respect to the analysis of bladder, breast, colorectal, head and neck, kidney, lung or pancreatic tissue. However, as one skilled in the art will appreciate, the assays and techniques described below can be applied to other types of patient samples, including body fluids (e.g. blood, urine or saliva), a tissue sample from a patient at risk of having bladder cancer, breast cancer, colorectal cancer, head and neck cancer, kidney cancer, lung cancer or pancreatic cancer (e.g. a biopsy such as a bladder, breast, colorectal, head and neck, kidney, lung or pancreatic biopsy) or homogenate thereof. The methods and compositions of the present invention are specially suited for screening, diagnosis and prognosis of a living subject, but may also be used for postmortem diagnosis in a subject, for example, to identify family members at risk of developing the same disease.

Ephrin Type-A Receptor 10

In one aspect of the invention, isobaric tags for relative and absolute quantification (iTRAQ) or other appropriate methods are used to analyze bladder cancer, breast cancer, colorectal cancer, head and neck cancer, kidney cancer, lung cancer or pancreatic cancer tissue samples from a subject, preferably a living subject, in order to measure the expression of the protein of the invention for screening or diagnosis of bladder cancer, breast cancer, colorectal cancer, head and neck cancer, kidney cancer, lung cancer or pancreatic cancer, to determine the prognosis of a bladder cancer, breast cancer, colorectal cancer, head and neck cancer, kidney cancer, lung cancer or pancreatic cancer patient, to monitor the effectiveness of bladder cancer, breast cancer, colorectal cancer, head and neck cancer, kidney cancer, lung cancer or pancreatic cancer therapy, or for drug development.

As used herein, the term "Protein of the invention", or "Ephrin type-A receptor 10", refers to the protein illustrated in FIG. 1, or fragments thereof. The protein can be detected by a variety of methods as described herein, including, experimentally by iTRAQ analysis of colorectal cancer, kidney cancer and lung cancer tissue samples. Protein derivatives of these sequences may also be useful for the same purposes as described herein.

This protein has been identified in membrane protein extracts of colorectal cancer, kidney cancer and lung cancer tissue samples from colorectal cancer, kidney cancer and lung cancer patients, through the methods and apparatus of the Preferred Technology (iTRAQ™ and tryptic digest of membrane protein extracts). Peptide sequences were compared to the SWISS-PROT and trEMBL databases (held by the Swiss Institute of Bioinformatics (SIB) and the European Bioinformatics Institute (EBI) which are available at world wide web.expasy.com), and the following entry: Q5JZY3, Ephrin type-A receptor 10 was identified. The nucleotide sequence encoding this protein is found at accession number NM_001099439, which is expressly incorporated herein by reference. The nucleotide sequence is found in FIG. 2.

According to SWISS-PROT, Ephrin type-A receptor 10 is mainly expressed in testis. It is a receptor for members of the ephrin-A family and binds to EFNA3, EFNA4 and EFNA5. Ephrin type-A receptor 10 is a member of the Eph receptor protein tyrosine kinase family. Its kinase domain most closely resembles Ephrin type-A which has no intrinsic kinase activity, but combines dimerically with another, kinase-active Eph receptor protein tyrosine kinase protein to form an active complex.

Ephrin type-A receptor 10 is also indicated to be expressed in bladder cancer, breast cancer, head and neck cancer and pancreatic cancer. Immunohistochemistry experiments (see Example 2) showed strong staining in bladder cancer, breast cancer, colorectal cancer, head and neck cancer, kidney cancer, lung cancer and pancreatic cancer. Accordingly, detection of Ephrin type-A receptor 10 serves as a diagnostic marker for bladder cancer, breast cancer, colorectal cancer, head and neck cancer, kidney cancer, lung cancer or pancreatic cancer. In some embodiments detection of Ephrin type-A receptor 10 serves as a diagnostic marker for bladder cancer, breast cancer, head and neck cancer, and pancreatic cancer.

The protein of the invention is useful as are fragments particularly epitope containing fragments e.g. antigenic or immunogenic fragments thereof and derivatives thereof. Epitope containing fragments including antigenic or immunogenic fragments will typically be of length 12 amino acids or more e.g. 20 amino acids or more e.g. 50 or 100 amino acids or more. Fragments may be 95% or more of the length of the full protein e.g. 90% or more e.g. 75% or 50% or 25% or 10% or more of the length of the full protein.

Alternatively, the protein/polypeptide employed or referred to herein may be limited to those specifically recited/described in the present specification or a moiety 80, 85, 90, 91, 92, 93, 94, 95, 96, 97, 98 or 99% identical or similar thereto.

Epitope containing fragments including antigenic or immunogenic fragments will be capable of eliciting a relevant immune response in a patient. DNA encoding the protein of the invention is also useful as are fragments thereof e.g. DNA encoding fragments of the protein of the invention such as immunogenic fragments thereof. Fragments of nucleic acid (e.g. DNA) encoding the protein of the invention may be 95% or more of the length of the full coding region e.g. 90% or more e.g. 75% or 50% or 25% or 10% or more of the length of the full coding region. Fragments of nucleic acid (e.g. DNA) may be 36 nucleotides or more e.g. 60 nucleotides or more e.g. 150 or 300 nucleotides or more in length.

Derivatives of the protein of the invention include variants on the sequence in which one or more (e.g. 1-20 such as 15 amino acids, or up to 20% such as up to 10% or 5% or 1% by number of amino acids based on the total length of the protein) deletions, insertions or substitutions have been made. Substitutions may typically be conservative substitutions. Derivatives will typically have essentially the same biological function as the protein from which they are derived. Derivatives will typically be comparably antigenic or immunogenic to the protein from which they are derived. Derivatives will typically have either the ligand-binding activity, or the active receptor-complex forming ability, or preferably both, of the protein from which they are derived.

Derivatives of proteins also include chemically treated protein such as carboxymethylated, carboxyamidated, acetylated proteins, for example treated during purification.

Tables 1a-1d below illustrates the different occurrences of Ephrin type-A receptor 10 as detected by mass spectrometry of membrane protein extracts of colorectal, kidney and lung tissue samples from colorectal cancer, kidney cancer, non-small cell lung cancer and small cell lung cancer patients respectively. The first column provides the sample number, the second column gives the iTRAQ experiment number for that sample and the last column provides a list of the sequences observed by mass spectrometry and the corresponding SEQ ID Nos.

TABLE 1a

Colorectal cancer

| Sample no. | Experiment no. | Tryptics identified [SEQ ID No] |
|---|---|---|
| Sample 1 | Experiment 1 | FSQIHSILSKMVQDPEPPK [3], HEGQLVAGQLMGLLPGLASAMK [4], SPLVLR [6] |
| Sample 2 | Experiment 1 | LEGVVTR [5] |

TABLE 1b

Kidney cancer

| Sample no. | Experiment no. | Tryptics identified [SEQ ID No] |
|---|---|---|
| Sample 1 | Experiment 1 | SPLVLR [6] |

TABLE 1c

Non-small cell lung cancer

| Sample no. | Experiment no. | Tryptics identified [SEQ ID No] |
|---|---|---|
| Sample 1 | Experiment 1 | SPLVLR [6] |

TABLE 1d

Small cell lung cancer

| Sample no. | Experiment no. | Tryptics identified [SEQ ID No] |
|---|---|---|
| Sample 1 | Experiment 1 | EIGPLSR [2] |

For Ephrin type-A receptor 10, the detected level obtained upon analyzing tissue from subjects having bladder cancer, breast cancer, colorectal cancer, head and neck cancer, kidney cancer, lung cancer or pancreatic cancer relative to the detected level obtained upon analyzing tissue from subjects free from bladder cancer, breast cancer, colorectal cancer, head and neck cancer, kidney cancer, lung cancer and pancreatic cancer will depend upon the particular analytical protocol and detection technique that is used. Accordingly, the present invention contemplates that each laboratory will establish a reference range in subjects free from bladder cancer, breast cancer, colorectal cancer, head and neck cancer, kidney cancer, lung cancer and pancreatic cancer according to the analytical protocol and detection technique in use, as is conventional in the diagnostic art. Preferably, at least one control positive tissue sample from a subject known to have bladder cancer, breast cancer, colorectal cancer, head and neck cancer, kidney cancer, lung cancer or pancreatic cancer or at least one control negative tissue sample from a subject known to be free from bladder cancer, breast cancer, colorectal cancer, head and neck cancer, kidney cancer, lung cancer and pancreatic cancer (and more preferably both positive and negative control samples) are included in each batch of test samples analysed.

Ephrin type-A receptor 10 can be used for detection, prognosis, diagnosis, or monitoring of bladder cancer, breast cancer, colorectal cancer, head and neck cancer, kidney cancer, lung cancer or pancreatic cancer or for drug development. In one embodiment of the invention, tissue from a subject (e.g. a subject suspected of having bladder cancer, breast cancer, colorectal cancer, head and neck cancer, kidney cancer, lung cancer or pancreatic cancer) is analysed by iTRAQ for detection of Ephrin type-A receptor 10. An increased abundance of Ephrin type-A receptor 10 in the tissue from the subject relative to tissue from a subject or subjects free from bladder cancer, breast cancer, colorectal cancer, head and neck cancer, kidney cancer, lung cancer and pancreatic cancer (e.g. a control sample) or a previously determined reference range indicates the presence of bladder cancer, breast cancer, colorectal cancer, head and neck cancer, kidney cancer, lung cancer or pancreatic cancer.

The sequences shown in Table 1 may be employed in any relevant aspect of the invention.

In relation to variants, fragments, epitope containing fragments, immunogenic fragments or antigenic fragments of Ephrin type-A receptor 10:

for colorectal cancer applications, in one aspect of the invention these comprise the sequences identified as tryptic sequences in the 3$^{rd}$ column of Table 1a;

for kidney cancer applications, in one aspect of the invention these comprise the sequences identified as tryptic sequences in the 3$^{rd}$ column of Table 1b;

for non-small cell lung cancer applications, in one aspect of the invention these comprise the sequences identified as tryptic sequences in the 3$^{rd}$ column of Table 1c;

for small cell lung cancer applications, in one aspect of the invention these comprise the sequences identified as tryptic sequences in the 3$^{rd}$ column of Table 1d.

As used herein, Ephrin type-A receptor 10 is "isolated" when it is present in a preparation that is substantially free of contaminating proteins, i.e. a preparation in which less than 10% (preferably less than 5%, more preferably less than 1%) of the total protein present is contaminating protein(s). A contaminating protein is a protein having a significantly different amino acid sequence from that of isolated Ephrin type-A receptor 10, as determined by mass spectral analysis. As used herein, a "significantly different" sequence is one that permits the contaminating protein to be resolved from Ephrin type-A receptor 10 by mass spectral analysis, performed according to the Reference Protocol described herein in Example 1.

Thus in one aspect the invention provides a pharmaceutical composition for the treatment of bladder cancer, breast cancer, colorectal cancer, head and neck cancer, kidney cancer, lung cancer or pancreatic cancer comprising a therapeutically effective amount of an Ephrin type-A receptor 10 polypeptide (particularly those defined above) or an immunogenic fragment thereof and an adjuvant.

Ephrin type-A receptor 10 can be assayed by any method known to those skilled in the art, including but not limited to, the Preferred Technologies described herein, kinase assays, enzyme assays, binding assays and other functional assays, immunoassays, and western blotting. In one embodiment, Ephrin type-A receptor 10 is analysed using isobaric tags for relative and absolute quantification (iTRAQ).

Alternatively, Ephrin type-A receptor 10 can be detected in an immunoassay. In one embodiment, an immunoassay is performed by contacting a sample from a subject to be tested with an anti-Ephrin type-A receptor 10 antibody (or other affinity reagent) under conditions such that binding (e.g. immunospecific binding) can occur if Ephrin type-A receptor 10 is present, and detecting or measuring the amount of any binding (e.g. immunospecific binding) by the agent. Ephrin type-A receptor 10 binding agents can be produced by the methods and techniques taught herein.

Ephrin type-A receptor 10 may be detected by virtue of the detection of a fragment thereof e.g. an epitope containing (e.g. an immunogenic or antigenic) fragment thereof. Fragments may have a length of at least 10, more typically at least 20 amino acids e.g. at least 50 or 100 amino acids e.g. at least 200 or 500 amino acids e.g. at least 800 or 1000 amino acids.

In one embodiment, binding of an affinity reagent (e.g. an antibody) in tissue sections can be used to detect aberrant Ephrin type-A receptor 10 localization or an aberrant level of Ephrin type-A receptor 10. In a specific embodiment, an antibody (or other affinity reagent) to Ephrin type-A receptor 10 can be used to assay a patient tissue (e.g. a bladder, breast, colorectal, head and neck, kidney, lung or pancreatic tissue) for the level of Ephrin type-A receptor 10 where an aberrant level of Ephrin type-A receptor 10 is indicative of bladder cancer, breast cancer, colorectal cancer, head and neck cancer, kidney cancer, lung cancer or pancreatic cancer. As used herein, an "aberrant level" means a level that is increased compared with the level in a subject free from bladder cancer, breast cancer, colorectal cancer, head and neck cancer, kidney cancer, lung cancer and pancreatic cancer or a reference level.

Any suitable immunoassay can be used, including, without limitation, competitive and non-competitive assay systems using techniques such as western blots, radioimmunoassays, ELISA (enzyme linked immunosorbent assay), "sandwich" immunoassays, immunoprecipitation assays, precipitin reactions, gel diffusion precipitin reactions, immunodiffusion assays, agglutination assays, complement-fixation assays, immunoradiometric assays, fluorescent immunoassays and protein A immunoassays.

For example, Ephrin type-A receptor 10 can be detected in a fluid sample (e.g. blood, urine, or saliva) by means of a two-step sandwich assay. In the first step, a capture reagent (e.g. an anti-Ephrin type-A receptor 10 antibody or other affinity reagent) is used to capture Ephrin type-A receptor 10. The capture reagent can optionally be immobilized on a solid phase. In the second step, a directly or indirectly labelled detection reagent is used to detect the captured Ephrin type-A receptor 10. In one embodiment, the detection reagent is a lectin. Any lectin can be used for this purpose that preferentially binds to Ephrin type-A receptor 10 rather than to other isoforms that have the same core protein as Ephrin type-A receptor 10 or to other proteins that share the antigenic determinant recognized by the antibody. In a preferred embodiment, the chosen lectin binds Ephrin type-A receptor 10 with at least 2-fold greater affinity, more preferably at least 5-fold greater affinity, still more preferably at least 10-fold greater affinity, than to said other isoforms that have the same core protein as Ephrin type-A receptor 10 or to said other proteins that share the antigenic determinant recognized by the affinity reagent. Based on the present description, a lectin that is suitable for detecting Ephrin type-A receptor 10 can readily be identified by methods well known in the art, for instance upon testing one or more lectins enumerated in Table I on pages 158-159 of Sumar et al., Lectins as Indicators of Disease-Associated Glycoforms, In: Gabius H-J & Gabius S (eds.), 1993, Lectins and Glycobiology, at pp. 158-174 (which is incorporated herein by reference in its entirety). In an alternative embodiment, the detection reagent is an antibody (or other affinity reagent), e.g. an antibody that specifically (e.g. immunospecifically) detects other post-translational modifications, such as an antibody that immunospecifically binds to phosphorylated amino acids. Examples of such antibodies include those that bind to phosphotyrosine (BD Transduction Laboratories, catalog nos.: P11230-050/P11230-150; P11120; P38820; P39020), those that bind to phosphoserine (Zymed Laboratories Inc., South San Francisco, Calif., catalog no. 61-8100) and those that bind to phosphothreonine (Zymed Laboratories Inc., South San Francisco, Calif., catalogue nos. 71-8200, 13-9200).

If desired, a gene encoding Ephrin type-A receptor 10, a related gene, or related nucleic acid sequences or subsequences, including complementary sequences, can also be used in hybridization assays. A nucleotide encoding Ephrin type-A receptor 10, or subsequences thereof comprising at least 8 nucleotides, preferably at least 12 nucleotides, and most preferably at least 15 nucleotides can be used as a hybridization probe. Hybridization assays can be used for detection, prognosis, diagnosis, or monitoring of conditions, disorders, or disease states, associated with aberrant expression of the gene encoding Ephrin type-A receptor 10, or for differential diagnosis of subjects with signs or symptoms suggestive of bladder cancer, breast cancer, colorectal cancer, head and neck cancer, kidney cancer, lung cancer or pancreatic cancer. In particular, such a hybridization assay can be carried out by a method comprising contacting a subject's sample containing nucleic acid with a nucleic acid probe capable of hybridizing to a DNA or RNA that encodes Ephrin type-A receptor 10, under conditions such that hybridization can occur, and detecting or measuring any resulting hybridization.

Hence nucleic acid encoding Ephrin type-A receptor 10 (e.g. DNA or more suitably RNA) may be detected, for example, using a hybridizing agent capable of hybridizing to nucleic acid encoding Ephrin type-A receptor 10.

One such exemplary method comprises:
(a) contacting one or more oligonucleotide probes comprising 10 or more consecutive nucleotides complementary to a nucleotide sequence encoding Ephrin type-A receptor 10, with an RNA obtained from a biological sample from the subject or with cDNA copied from the RNA, wherein said contacting occurs under conditions that permit hybridization of the probe to the nucleotide sequence if present;
(b) detecting hybridization, if any, between the probe and the nucleotide sequence; and
(c) comparing the hybridization, if any, detected in step (b) with the hybridization detected in a control sample, or with a previously determined reference range.

The invention also provides diagnostic kits, comprising an anti-Ephrin type-A receptor 10 antibody (or other affinity reagent). In addition, such a kit may optionally comprise one or more of the following: (1) instructions for using the anti-Ephrin type-A receptor 10 affinity reagent for diagnosis, prognosis, therapeutic monitoring or any combination of these applications; (2) a labelled binding partner to the affinity reagent; (3) a solid phase (such as a reagent strip) upon which the anti-Ephrin type-A receptor 10 affinity reagent is immobilized; and (4) a label or insert indicating regulatory approval for diagnostic, prognostic or therapeutic use or any combination thereof. If no labelled binding partner to the affinity reagent is provided, the anti-Ephrin type-A receptor 10 affinity reagent itself can be labelled with a detectable marker, e.g. a chemiluminescent, enzymatic, fluorescent, or radioactive moiety.

The invention also provides a kit comprising a nucleic acid probe capable of hybridizing to nucleic acid, suitably RNA, encoding Ephrin type-A receptor 10. In a specific embodiment, a kit comprises in one or more containers a pair of primers (e.g. each in the size range of 6-30 nucleotides, more preferably 10-30 nucleotides and still more preferably 10-20 nucleotides) that under appropriate reaction conditions can prime amplification of at least a portion of a nucleic acid encoding Ephrin type-A receptor 10, such as by polymerase chain reaction (see, e.g. Innis et al., 1990, PCR Protocols, Academic Press, Inc., San Diego, Calif.), ligase chain reaction (see EP 320,308) use of Qβ replicase, cyclic probe reaction, or other methods known in the art.

A kit can optionally further comprise a predetermined amount of Ephrin type-A receptor 10 or a nucleic acid encoding Ephrin type-A receptor 10, e.g. for use as a standard or control.

Use in Clinical Studies

The diagnostic methods and compositions of the present invention can assist in monitoring a clinical study, e.g. to evaluate drugs for therapy of bladder cancer, breast cancer, colorectal cancer, head and neck cancer, kidney cancer, lung cancer or pancreatic cancer. In one embodiment, candidate molecules are tested for their ability to restore Ephrin type-A receptor 10 levels in a subject having bladder cancer, breast cancer, colorectal cancer, head and neck cancer, kidney cancer, lung cancer or pancreatic cancer to levels found in subjects free from bladder cancer, breast cancer, colorectal cancer, head and neck cancer, kidney cancer, lung cancer and pancreatic cancer or, in a treated subject, to preserve Ephrin type-A receptor 10 levels at or near non-bladder cancer, non-breast cancer, non-colorectal cancer, non-head and neck cancer, non-kidney cancer, non-lung cancer or non-pancreatic cancer values.

In another embodiment, the methods and compositions of the present invention are used to screen candidates for a clinical study to identify individuals having bladder cancer, breast cancer, colorectal cancer, head and neck cancer, kidney cancer, lung cancer or pancreatic cancer; such individuals can then be excluded from the study or can be placed in a separate cohort for treatment or analysis.

Production of Protein of the Invention and Corresponding Nucleic Acid

In one aspect the invention provides a method of treating or preventing bladder cancer, breast cancer, colorectal cancer, head and neck cancer, kidney cancer, lung cancer or pancreatic cancer, comprising administering to a subject in need of such treatment or prevention a therapeutically effective amount of nucleic acid encoding Ephrin type-A receptor 10 or one or more fragments or derivatives thereof, for example in the form of a vaccine.

In another aspect there is provided a method of treating or preventing bladder cancer, breast cancer, colorectal cancer, head and neck cancer, kidney cancer, lung cancer or pancreatic cancer comprising administering to a subject in need of such treatment or prevention a therapeutically effective amount of nucleic acid that inhibits the function or expression of Ephrin type-A receptor 10.

The methods (and/or other DNA aspects disclosed herein) of the invention may, for example include wherein the nucleic acid is an Ephrin type-A receptor 10 anti-sense nucleic acid or ribozyme.

Thus the invention includes the use of nucleic acid encoding Ephrin type-A receptor 10 or one or more fragments or derivatives thereof, in the manufacture of a medicament for treating or preventing bladder cancer, breast cancer, colorectal cancer, head and neck cancer, kidney cancer, lung cancer or pancreatic cancer.

There is also provided the use of nucleic acid that inhibits the function or expression of Ephrin type-A receptor 10 in the manufacture of a medicament for treating or preventing bladder cancer, breast cancer, colorectal cancer, head and neck cancer, kidney cancer, lung cancer or pancreatic cancer.

A DNA employed in the present invention can be obtained by isolation as a cDNA fragment from cDNA libraries using as starter materials commercial mRNAs and determining and identifying the nucleotide sequences thereof. That is, specifically, clones are randomly isolated from cDNA libraries, which are prepared according to Ohara et al's method (DNA Research Vol. 4, 53-59 (1997)). Next, through hybridization, duplicated clones (which appear repeatedly) are removed and then in vitro transcription and translation are carried out. Nucleotide sequences of both termini of clones, for which products of 50 kDa or more are confirmed, are determined.

Furthermore, databases of known genes are searched for homology using the thus obtained terminal nucleotide sequences as queries.

In addition to the above screening method, the 5' and 3' terminal sequences of cDNA are related to a human genome sequence. Then an unknown long-chain gene is confirmed in a region between the sequences, and the full-length of the cDNA is analyzed. In this way, an unknown gene that is unable to be obtained by a conventional cloning method that depends on known genes can be systematically cloned.

Moreover, all of the regions of a human-derived gene containing a DNA of the present invention can also be prepared using a PCR method such as RACE while paying sufficient attention to prevent artificial errors from taking place in short fragments or obtained sequences. As described above, clones having DNA of the present invention can be obtained.

In another means for cloning DNA of the present invention, a synthetic DNA primer having an appropriate nucleotide sequence of a portion of a polypeptide of the present invention is produced, followed by amplification by the PCR method using an appropriate library. Alternatively, selection can be carried out by hybridization of the DNA of the present invention with a DNA that has been incorporated into an appropriate vector and labelled with a DNA fragment or a synthetic DNA encoding some or all of the regions of the polypeptide of the present invention. Hybridization can be carried out by, for example, the method described in Current Protocols in Molecular Biology (edited by Frederick M. Ausubel et al., 1987). DNA of the present invention may be any DNA, as long as they contain nucleotide sequences encoding the polypeptides of the present invention as described above. Such a DNA may be a cDNA identified and isolated from cDNA libraries or the like that are derived from bladder, breast, colorectal, head and neck, kidney, lung or pancreatic tissue. Such a DNA may also be a synthetic DNA or the like. Vectors for use in library construction may be any of bacteriophages, plasmids, cosmids, phargemids, or the like. Furthermore, by the use of a total RNA fraction or a mRNA fraction prepared from the above cells and/or tissues, amplification can be carried out by a direct reverse transcription coupled polymerase chain reaction (hereinafter abbreviated as "RT-PCR method").

DNA encoding the above polypeptide consisting of an amino acid sequence that is substantially identical to the amino acid sequence of Ephrin type-A receptor 10 or DNA encoding the above polypeptide consisting of an amino acid sequence derived from the amino acid sequence of Ephrin type-A receptor 10 by deletion, substitution, or addition of one or more amino acids composing a portion of the amino acid sequence can be easily produced by an appropriate combination of, for example, a site-directed mutagenesis method, a gene homologous recombination method, a primer elongation method, and the PCR method known by persons skilled in the art. In addition, at this time, a possible method for causing a polypeptide to have substantially equivalent biological activity is substitution of homologous amino acids (e.g. polar and nonpolar amino acids, hydrophobic and hydrophilic amino acids, positively-charged and negatively charged amino acids, and aromatic amino acids) among amino acids composing the polypeptide. Furthermore, to maintain substantially equivalent biological activity, amino acids within functional domains contained in the polypeptide of the present invention are preferably conserved.

Furthermore, examples of DNA of the present invention include DNA comprising a nucleotide sequence that encodes the amino acid sequence of Ephrin type-A receptor 10 and DNA hybridizing under stringent conditions to the DNA and encoding a polypeptide (protein) having biological activity (function) equivalent to the function of the polypeptide consisting of the amino acid sequence of Ephrin type-A receptor 10. Under such conditions, an example of such DNA capable of hybridizing to DNA comprising the nucleotide sequence that encodes the amino acid sequence of Ephrin type-A receptor 10 is DNA comprising a nucleotide sequence that has a degree of overall mean homology with the entire nucleotide sequence of the DNA, such as approximately 80% or more, preferably approximately 90% or more, and more preferably approximately 95% or more. Hybridization can be carried out according to a method known in the art such as a method described in Current Protocols in Molecular Biology (edited by Frederick M. Ausubel et al., 1987) or a method according thereto. Here, "stringent conditions" are, for example, conditions of approximately "1*SSC, 0.1% SDS, and 37° C., more stringent conditions of approximately "0.5*SSC, 0.1% SDS, and 42° C., or even more stringent conditions of approximately "0.2*SSC, 0.1% SDS, and 65° C. With more stringent hybridization conditions, the isolation of a DNA having high homology with a probe sequence can be expected. The above combinations of SSC, SDS, and temperature conditions are given for illustrative purposes. Stringency similar to the above can be achieved by persons skilled in the art using an appropriate combination of the above factors or other factors (for example, probe concentration, probe length, and reaction time for hybridization) for determination of hybridization stringency.

A cloned DNA of the present invention can be directly used or used, if desired, after digestion with a restriction enzyme or addition of a linker, depending on purposes. The DNA may have ATG as a translation initiation codon at the 5' terminal side and have TAA, TGA, or TAG as a translation termination codon at the 3' terminal side. These translation initiation and translation termination codons can also be added using an appropriate synthetic DNA adapter.

In the methods/uses of the invention Ephrin type-A receptor 10 may, for example, be provided in isolated form, such as where the Ephrin type-A receptor 10 polypeptide has been purified to at least to some extent. Ephrin type-A receptor 10 polypeptide may be provided in substantially pure form, that is to say free, to a substantial extent, from other proteins. Ephrin type-A receptor 10 polypeptide can also be produced using recombinant methods, synthetically produced or produced by a combination of these methods. Ephrin type-A receptor 10 can be easily prepared by any method known by persons skilled in the art, which involves producing an expression vector containing a DNA of the present invention or a gene containing a DNA of the present invention, culturing a transformant transformed using the expression vector, generating and accumulating a polypeptide of the present invention or a recombinant protein containing the polypeptide, and then collecting the resultant.

Recombinant Ephrin type-A receptor 10 polypeptide may be prepared by processes well known in the art from genetically engineered host cells comprising expression systems. Accordingly, the present invention also relates to expression systems which comprise an Ephrin type-A receptor 10 polypeptide or nucleic acid, to host cells which are genetically engineered with such expression systems and to the production of Ephrin type-A receptor 10 polypeptide by recombinant techniques. For recombinant Ephrin type-A receptor 10 polypeptide production, host cells can be genetically engineered to incorporate expression systems or portions thereof for nucleic acids. Such incorporation can be performed using methods well known in the art, such as, calcium phosphate transfection, DEAD-dextran mediated transfection, transvection, microinjection, cationic lipid-mediated transfection, electroporation, transduction, scrape loading, ballistic introduction or infection (see e.g. Davis et al., Basic Methods in Molecular Biology, 1986 and Sambrook et al., Molecular Cloning: A Laboratory Manual, 2nd Ed., Cold Spring Harbour laboratory Press, Cold Spring Harbour, N.Y., 1989).

As host cells, for example, bacteria of the genus *Escherichia, Streptococci, Staphylococci, Streptomyces*, bacteria of the genus *Bacillus*, yeast, *Aspergillus* cells, insect cells, insects, and animal cells are used. Specific examples of bacteria of the genus *Escherichia*, which are used herein, include *Escherichia coli* K12 and DH1 (Proc. Natl. Acad. Sci. U.S.A., Vol. 60, 160 (1968)), JM103 (Nucleic Acids Research, Vol. 9, 309 (1981)), JA221 (Journal of Molecular Biology, Vol. 120, 517 (1978)), and HB101 (Journal of Molecular Biology, Vol. 41, 459 (1969)). As bacteria of the genus *Bacillus*, for example, *Bacillus subtilis* MI114 (Gene, Vol. 24, 255 (1983)) and 207-21 (Journal of Biochemistry, Vol. 95, 87 (1984)) are used. As yeast, for example, *Saccaromyces* cerevisiae AH22, AH22R-, NA87-11A, DKD-5D, and 20B-12, *Schizosaccaromyces pombe* NCYC1913 and NCYC2036, and *Pichia pastoris* are used. As insect cells, for example, *Drosophila* S2 and *Spodoptera* Sf9 cells are used. As animal cells, for example, COS-7 and Vero monkey cells, CHO Chinese hamster cells (hereinafter abbreviated as CHO cells), dhfr-gene-deficient CHO cells, mouse L cells, mouse AtT-20 cells, mouse myeloma cells, rat GH3 cells, human FL cells, COS, HeLa, C127, 3T3, HEK 293, BHK and Bowes melanoma cells are used.

Cell-free translation systems can also be employed to produce recombinant polypeptides (e.g. rabbit reticulocyte lysate, wheat germ lysate, SP6/T7 in vitro T&T and RTS 100 *E. Coli* HY transcription and translation kits from Roche Diagnostics Ltd., Lewes, UK and the TNT Quick coupled Transcription/Translation System from Promega UK, Southampton, UK).

The expression vector can be produced according to a method known in the art. For example, the vector can be produced by (1) excising a DNA fragment containing a DNA of the present invention or a gene containing a DNA of the present invention and (2) ligating the DNA fragment downstream of the promoter in an appropriate expression vector. A wide variety of expression systems can be used, such as and without limitation, chromosomal, episomal and virus-derived systems, e.g. plasmids derived from *Escherichia coli* (e.g. pBR322, pBR325, pUC18, and pUC118), plasmids derived from *Bacillus subtilis* (e.g. pUB110, pTP5, and pC194), from bacteriophage, from transposons, from yeast episomes (e.g. pSH19 and pSH15), from insertion elements, from yeast chromosomal elements, from viruses such as baculoviruses, papova viruses such as SV40, vaccinia viruses, adenoviruses, fowl pox viruses, pseudorabies viruses and retroviruses, and vectors derived from combinations thereof, such as those derived from plasmid and bacteriophage (such as [lambda] phage) genetic elements, such as cosmids and phagemids. The expression systems may contain control regions that regulate as well as engender expression. Promoters to be used in the present invention may be any promoters as long as they are appropriate for hosts to be used for gene expression. For example, when a host is *Escherichia coli*, a trp promoter, a lac promoter, a recA promoter, a pL promoter, an 1 pp promoter, and the like are preferred. When a host is *Bacillus subtilis*, an SPO1 promoter, an SPO2 promoter, a penP promoter, and the like are preferred. When a host is yeast, a PHO5 promoter, a PGK promoter, a GAP promoter, an ADH promoter, and the like are preferred. When an animal cell is used as a host, examples of promoters for use in this case include an SRa promoter, an SV40 promoter, an LTR promoter, a CMV promoter, and an HSV-TK promoter. Generally, any system or vector that is able to maintain, propagate or express a nucleic acid to produce a polypeptide in a host may be used.

The appropriate nucleic acid sequence may be inserted into an expression system by any variety of well known and routine techniques, such as those set forth in Sambrook et al., supra. Appropriate secretion signals may be incorporated into the Ephrin type-A receptor 10 polypeptide to allow secretion of the translated protein into the lumen of the endoplasmic reticulum, the periplasmic space or the extracellular environment. These signals may be endogenous to the Ephrin type-A receptor 10 polypeptide or they may be heterologous signals. Transformation of the host cells can be carried out according to methods known in the art. For example, the following documents can be referred to: Proc. Natl. Acad. Sci. U.S.A., Vol. 69, 2110 (1972); Gene, Vol. 17, 107 (1982); Molecular & General Genetics, Vol. 168, 111 (1979); Methods in Enzymology, Vol. 194, 182-187 (1991); Proc. Natl. Acad. Sci. U.S.A.), Vol. 75, 1929 (1978); Cell Technology, separate volume 8, New Cell Technology, Experimental Protocol. 263-267 (1995) (issued by Shujunsha); and Virology, Vol. 52, 456 (1973). The thus obtained transformant transformed with an expression vector containing a DNA of the present invention or a gene containing a DNA of the present invention can be cultured according to a method known in the art. For example, when hosts are bacteria of the genus *Escherichia*, the bacteria are generally cultured at approximately 15° C. to 43° C. for approximately 3 to 24 hours. If necessary, aeration or agitation can also be added. When hosts are bacteria of the genus *Bacillus*, the bacteria are generally cultured at approximately 30° C. to 40° C. for approximately 6 to 24 hours. If necessary, aeration or agitation can also be added. When transformants whose hosts are yeast are cultured, culture is generally carried out at approximately 20° C. to 35° C. for approximately 24 to 72 hours using media with pH adjusted to be approximately 5 to 8. If necessary, aeration or agitation can also be added. When transformants whose hosts are animal cells are cultured, the cells are generally cultured at approximately 30° C. to 40° C. for approximately 15 to 60 hours using media with the pH adjusted to be approximately 6 to 8. If necessary, aeration or agitation can also be added.

If an Ephrin type-A receptor 10 polypeptide is to be expressed for use in cell-based screening assays, it is preferred that the polypeptide be produced at the cell surface. In this event, the cells may be harvested prior to use in the screening assay. If the Ephrin type-A receptor 10 polypeptide is secreted into the medium, the medium can be recovered in order to isolate said polypeptide. If produced intracellularly, the cells must first be lysed before the Ephrin type-A receptor 10 polypeptide is recovered.

Ephrin type-A receptor 10 polypeptide can be recovered and purified from recombinant cell cultures or from other biological sources by well known methods including, ammonium sulphate or ethanol precipitation, acid extraction, anion or cation exchange chromatography, phosphocellulose chromatography, affinity chromatography, hydrophobic interaction chromatography, hydroxylapatite chromatography, molecular sieving chromatography, centrifugation methods, electrophoresis methods and lectin chromatography. In one embodiment, a combination of these methods is used. In another embodiment, high performance liquid chromatography is used. In a further embodiment, an antibody which specifically binds to an Ephrin type-A receptor 10 polypeptide can be used to deplete a sample comprising an Ephrin type-A receptor 10 polypeptide of said polypeptide or to purify said polypeptide.

To separate and purify a polypeptide or a protein of the present invention from the culture products, for example, after culture, microbial bodies or cells are collected by a known method, they are suspended in an appropriate buffer, the microbial bodies or the cells are disrupted by, for example, ultrasonic waves, lysozymes, and/or freeze-thawing, the resultant is then subjected to centrifugation or filtration, and then a crude extract of the protein can be obtained. The buffer may also contain a protein denaturation agent such as urea or guanidine hydrochloride or a surfactant such as Triton X-100™. When the protein is secreted in a culture solution, microbial bodies or cells and a supernatant are separated by a known method after the completion of culture and then the supernatant is collected. The protein contained in the thus obtained culture supernatant or the extract can be purified by an appropriate combination of known separation and purification methods. The thus obtained polypeptide (protein) of the present invention can be converted into a salt by a known method or a method according thereto. Conversely, when the polypeptide (protein) of the present invention is obtained in the form of a salt, it can be converted into a free protein or peptide or another salt by a known method or a method according thereto. Moreover, an appropriate protein modification enzyme such as trypsin or chymotrypsin is caused to act on a protein produced by a recombinant before or after purification, so that modification can be arbitrarily added or a polypeptide can be partially removed. The presence of a polypeptide (protein) of the present invention or a salt thereof can be measured by various binding assays, enzyme immunoassays using specific antibodies, and the like.

Techniques well known in the art may be used for refolding to regenerate native or active conformations of the Ephrin type-A receptor 10 polypeptide when the polypeptide has been denatured during isolation and or purification. In the context of the present invention, Ephrin type-A receptor 10 polypeptide can be obtained from a biological sample from any source, such as and without limitation, a blood sample or tissue sample, e.g. a bladder, breast, colorectal, head and neck, kidney, lung or pancreatic tissue sample.

Ephrin type-A receptor 10 polypeptide may be in the form of a "mature protein" or may be part of a larger protein such as a fusion protein. It is often advantageous to include an additional amino acid sequence which contains secretory or leader sequences, a pre-, pro- or prepro-protein sequence, or a sequence which aids in purification such as an affinity tag, for example, but without limitation, multiple histidine residues, a FLAG tag, HA tag or myc tag.

Ephrin type-A receptor 10 may, for example, be fused with a heterologous fusion partner such as the surface protein, known as protein D from *Haemophilus Influenza* B, a nonstructural protein from influenzae virus such as NS1, the S antigen from Hepatitis B or a protein known as LYTA such as the C terminal thereof.

An additional sequence that may provide stability during recombinant production may also be used. Such sequences may be optionally removed as required by incorporating a cleavable sequence as an additional sequence or part thereof. Thus, an Ephrin type-A receptor 10 polypeptide may be fused to other moieties including other polypeptides or proteins (for example, glutathione S-transferase and protein A). Such a fusion protein can be cleaved using an appropriate protease, and then separated into each protein. Such additional sequences and affinity tags are well known in the art. In addition to the above, features known in the art, such as an enhancer, a splicing signal, a polyA addition signal, a selection marker, and an SV40 replication origin can be added to an expression vector, if desired.

Production of Affinity Reagents to Ephrin Type-A Receptor 10

According to those in the art, there are three main types of immunoaffinity reagent—monoclonal antibodies, phage display antibodies and smaller antibody-derived molecules such as Affibodies, Domain Antibodies (dAbs), Nanobodies, UniBodies, DARPins, Anticalins, Duocalins, Avimers or Versabodies. In general in applications according to the present invention where the use of antibodies is stated, other affinity reagents (e.g. Affibodies, Domain Antibodies, Nanobodies, UniBodies, DARPins, Anticalins, Duocalins, Avimers or Versabodies) may be employed. Such substances may be said to be capable of immunospecific binding to Ephrin type-A receptor 10. Where appropriate the term "affinity agent" shall be construed to embrace immunoaffinity reagents and other substances capable of specific binding to Ephrin type-A receptor 10 including but not limited to ligands, lectins, streptavidins, antibody mimetics and synthetic binding agents.

Production of Antibodies to Ephrin Type-A Receptor 10

According to the invention Ephrin type-A receptor 10, an Ephrin type-A receptor 10 analogue, an Ephrin type-A receptor 10-related protein or a fragment or derivative of any of the foregoing may be used as an immunogen to generate antibodies which immunospecifically bind such an immunogen. Such immunogens can be isolated by any convenient means, including the methods described above. The term "antibody" as used herein refers to a peptide or polypeptide derived from, modelled after or substantially encoded by an immunoglobulin gene or immunoglobulin genes, or fragments thereof, capable of specifically binding an antigen or epitope. See, e.g. *Fundamental Immunology*, 3$^{rd}$ Edition, W. E. Paul, ed., Raven Press, N.Y. (1993); Wilson (1994) *J. Immunol. Methods* 175: 267-273; Yarmush (1992) *J. Biochem. Biophys. Methods* 25:85-97. The term antibody includes antigen-binding portions, i.e., "antigen binding sites" (e.g. fragments, subsequences, complementarity determining regions (CDRs)) that retain capacity to bind antigen, including (i) a Fab fragment, a monovalent fragment consisting of the VL, VH, CL and CH1 domains; (ii) a F(ab')$_2$ fragment, a bivalent fragment comprising two Fab fragments linked by a disulfide bridge at the hinge region; (iii) a Fd fragment consisting of the VH and CH1 domains; (iv) a Fv fragment consisting of the VL and VH domains of a single arm of an antibody, (v) a dAb fragment (Ward et al., (1989) *Nature* 341:544-546), which consists of a VH domain; and (vi) an isolated complementarity determining region (CDR). Single chain antibodies are also included by reference in the term "antibody." Antibodies of the invention include, but are not limited to polyclonal, monoclonal, bispecific, humanized or chimeric antibodies, single chain antibodies, Fab fragments and F(ab')$_2$ fragments, fragments produced by a Fab expression library, anti-idiotypic (anti-Id) antibodies, and epitope-binding fragments of any of the above. The immunoglobulin molecules of the invention can be of any class (e.g. IgG, IgE, IgM, IgD and IgA) or subclass of immunoglobulin molecule.

The term "specifically binds" (or "immunospecifically binds") is not intended to indicate that an antibody binds exclusively to its intended target. Rather, an antibody "specifically binds" if its affinity for its intended target is typically about 5-fold greater when compared to its affinity for a non-target molecule. Suitably there is no significant cross-reaction or cross-binding with undesired substances, especially naturally occurring proteins or tissues of a healthy person or animal. The affinity of the antibody will, for example, be at least about 5 fold, such as 10 fold, such as 25-fold, especially 50-fold, and particularly 100-fold or more, greater for a target molecule than its affinity for a non-target molecule. In some embodiments, specific binding between an antibody or other binding agent and an antigen means a binding affinity of at least $10^6$ M$^{-1}$. Antibodies may, for example, bind with affinities of at least about $10^7$ M$^{-1}$, such as between about $10^8$ M$^{-1}$ to about $10^9$ M$^{-1}$, about $10^9$ M$^{-1}$ to about $10^{10}$ M$^{-1}$, or about $10^{10}$ M$^{-1}$ to about $10^{11}$ M$^{-1}$.

Affinity is calculated as $K_d = k_{off}/k_{on}$ ($k_{off}$ is the dissociation rate constant, $k_{on}$ is the association rate constant and $K_d$ is the equilibrium constant. Affinity can be determined at equilibrium by measuring the fraction bound (r) of labelled ligand at various concentrations (c). The data are graphed using the Scatchard equation: r/c=K(n−r):

where r=moles of bound ligand/mole of receptor at equilibrium;
c=free ligand concentration at equilibrium;
K=equilibrium association constant; and
n=number of ligand binding sites per receptor molecule By graphical analysis, r/c is plotted on the Y-axis versus r on the X-axis thus producing a Scatchard plot. The affinity is the negative slope of the line. $k_{off}$ can be determined by competing bound labelled ligand with unlabelled excess ligand (see, e.g. U.S. Pat. No. 6,316,409). The affinity of a targeting agent for its target molecule is, for example, at least about $1 \times 10^{-6}$ moles/litre, such as at least about $1 \times 10^{-7}$ moles/litre, such as at least about $1 \times 10^{-8}$ moles/litre, especially at least about $1 \times 10^{-9}$ moles/litre, and particularly at least about $1 \times 10^{-10}$ moles/litre. Antibody affinity measurement by Scatchard analysis is well known in the art. See, e.g. van Erp et al., *J. Immunoassay* 12: 425-43, 1991; Nelson and Griswold, *Comput. Methods Programs Biomed.* 27: 65-8, 1988.

In one embodiment, antibodies that recognize gene products of genes encoding Ephrin type-A receptor 10 are publicly available. In another embodiment, methods known to those skilled in the art are used to produce antibodies that recognize Ephrin type-A receptor 10, an Ephrin type-A receptor 10 analogue, an Ephrin type-A receptor 10-related polypeptide, or a fragment or derivative of any of the foregoing. One skilled in the art will recognize that many procedures are available for the production of antibodies, for example, as described in Antibodies, A Laboratory Manual, Ed Harlow and David Lane, Cold Spring Harbor Laboratory (1988), Cold Spring Harbor, N.Y. One skilled in the art will also appreciate that binding fragments or Fab fragments which mimic antibodies can also be prepared from genetic information by various procedures (Antibody Engineering: A Practical Approach (Borrebaeck, C., ed.), 1995, Oxford University Press, Oxford; J. Immunol. 149, 3914-3920 (1992)).

In one embodiment of the invention, antibodies to a specific domain of Ephrin type-A receptor 10 are produced. In a specific embodiment, hydrophilic fragments of Ephrin type-A receptor 10 are used as immunogens for antibody production.

In the production of antibodies, screening for the desired antibody can be accomplished by techniques known in the art, e.g. ELISA (enzyme-linked immunosorbent assay). For example, to select antibodies which recognize a specific domain of Ephrin type-A receptor 10, one may assay generated hybridomas for a product which binds to an Ephrin type-A receptor 10 fragment containing such domain. For selection of an antibody that specifically binds a first Ephrin type-A receptor 10 homologue but which does not specifically bind to (or binds less avidly to) a second Ephrin type-A receptor 10 homologue, one can select on the basis of positive binding to the first Ephrin type-A receptor 10 homologue and a lack of binding to (or reduced binding to) the second Ephrin type-A receptor 10 homologue. Similarly, for selection of an antibody that specifically binds Ephrin type-A receptor 10 but which does not specifically bind to (or binds less avidly to) a different isoform of the same protein (such as a different glycoform having the same core peptide as Ephrin type-A receptor 10), one can select on the basis of positive binding to Ephrin type-A receptor 10 and a lack of binding to (or reduced binding to) the different isoform (e.g. a different glycoform). Thus, the present invention provides an antibody (such as a monoclonal antibody) that binds with greater affinity (for example at least 2-fold, such as at least 5-fold, particularly at least 10-fold greater affinity) to Ephrin type-A receptor 10 than to a different isoform or isoforms (e.g. glycoforms) of Ephrin type-A receptor 10.

Polyclonal antibodies which may be used in the methods of the invention are heterogeneous populations of antibody molecules derived from the sera of immunized animals. Unfractionated immune serum can also be used. Various procedures known in the art may be used for the production of polyclonal antibodies to Ephrin type-A receptor 10, a fragment of Ephrin type-A receptor 10, an Ephrin type-A receptor 10-related polypeptide, or a fragment of an Ephrin type-A receptor 10-related polypeptide. For example, one way is to purify polypeptides of interest or to synthesize the polypeptides of interest using, e.g. solid phase peptide synthesis methods well known in the art. See, e.g. *Guide to Protein Purification*, Murray P. Deutcher, ed., *Meth. Enzymol.* Vol 182 (1990); Solid Phase Peptide Synthesis, Greg B. Fields ed., *Meth. Enzymol.* Vol 289 (1997); Kiso et al., *Chem. Pharm. Bull.* (Tokyo) 38: 1192-99, 1990; Mostafavi et al., *Biomed. Pept. Proteins Nucleic Acids* 1: 255-60, 1995; Fujiwara et al., *Chem. Pharm. Bull.* (Tokyo) 44: 1326-31, 1996. The selected polypeptides may then be used to immunize by injection various host animals, including but not limited to rabbits, mice, rats, etc., to generate polyclonal or monoclonal antibodies. If Ephrin type-A receptor 10 is purified by gel electrophoresis, Ephrin type-A receptor 10 can be used for immunization with or without prior extraction from the polyacrylamide gel. Various adjuvants (i.e. immunostimulants) may be used to enhance the immunological response, depending on the host species, including, but not limited to, complete or incomplete Freund's adjuvant, a mineral gel such as aluminium hydroxide, surface active substance such as lysolecithin, pluronic polyol, a polyanion, a peptide, an oil emulsion, keyhole limpet hemocyanin, dinitrophenol, and an adjuvant such as BCG (bacille Calmette-Guerin) or *corynebacterium parvum*. Additional adjuvants are also well known in the art.

For preparation of monoclonal antibodies (mAbs) directed toward Ephrin type-A receptor 10, a fragment of Ephrin type-A receptor 10, an Ephrin type-A receptor 10-related polypeptide, or a fragment of an Ephrin type-A receptor 10-related polypeptide, any technique which provides for the production of antibody molecules by continuous cell lines in culture may be used. For example, the hybridoma technique originally developed by Kohler and Milstein (1975, Nature 256:495-497), as well as the trioma technique, the human B-cell hybridoma technique (Kozbor et al., 1983, Immunology Today 4:72), and the EBV-hybridoma technique to produce human monoclonal antibodies (Cole et al., 1985, in Monoclonal Antibodies and Cancer Therapy, Alan R. Liss, Inc., pp. 77-96). Such antibodies may be of any immunoglobulin class including IgG, IgM, IgE, IgA, IgD and any subclass thereof. The hybridoma producing the mAbs of the invention may be cultivated in vitro or in vivo. In an additional embodiment of the invention, monoclonal antibodies can be produced in germ-free animals utilizing known technology (PCT/US90/02545, incorporated herein by reference).

The monoclonal antibodies include but are not limited to human monoclonal antibodies and chimeric monoclonal antibodies (e.g. human-mouse chimeras). A chimeric antibody is a molecule in which different portions are derived from different animal species, such as those having a human immunoglobulin constant region and a variable region derived from a murine mAb. (See, e.g. Cabilly et al., U.S. Pat. No. 4,816, 567; and Boss et al., U.S. Pat. No. 4,816,397, which are incorporated herein by reference in their entirety.) Humanized antibodies are antibody molecules from non-human species having one or more complementarity determining regions (CDRs) from the non-human species and a framework region from a human immunoglobulin molecule. (See, e.g. Queen, U.S. Pat. No. 5,585,089, which is incorporated herein by reference in its entirety.)

Chimeric and humanized monoclonal antibodies can be produced by recombinant DNA techniques known in the art, for example using methods described in PCT Publication No. WO 87/02671; European Patent Application 184,187; European Patent Application 171,496; European Patent Application 173,494; PCT Publication No. WO 86/01533; U.S. Pat. No. 4,816,567; European Patent Application 125,023; Better et al., 1988, Science 240:1041-1043; Liu et al., 1987, Proc. Natl. Acad. Sci. USA 84:3439-3443; Liu et al., 1987, J. Immunol. 139:3521-3526; Sun et al., 1987, Proc. Natl. Acad. Sci. USA 84:214-218; Nishimura et al., 1987, Canc. Res. 47:999-1005; Wood et al., 1985, Nature 314:446-449; and Shaw et al., 1988, J. Natl. Cancer Inst. 80:1553-1559; Morrison, 1985, Science 229:1202-1207; Oi et al., 1986, Bio/Techniques 4:214; U.S. Pat. No. 5,225,539; Jones et al., 1986, Nature 321:552-525; Verhoeyan et al. (1988) Science 239:1534; and Beidler et al., 1988, J. Immunol. 141: 4053-4060.

Completely human antibodies are particularly desirable for therapeutic treatment of human subjects. Such antibodies can be produced using transgenic mice which are incapable of expressing endogenous immunoglobulin heavy and light chain genes, but which can express human heavy and light chain genes. The transgenic mice are immunized in the normal fashion with a selected antigen, e.g. all or a portion of Ephrin type-A receptor 10. Monoclonal antibodies directed against the antigen can be obtained using conventional hybridoma technology. The human immunoglobulin transgenes harboured by the transgenic mice rearrange during B cell differentiation, and subsequently undergo class switching and somatic mutation. Thus, using such a technique, it is possible to produce therapeutically useful IgG, IgA, IgM and IgE antibodies. For an overview of this technology for producing human antibodies, see Lonberg and Huszar (1995, Int. Rev. Immunol. 13:65-93). For a detailed discussion of this technology for producing human antibodies and human monoclonal antibodies and protocols for producing such antibodies, see, e.g. U.S. Pat. Nos. 5,625,126; 5,633,425; 5,569, 825; 5,661,016; and 5,545,806. In addition, companies such as Abgenix, Inc. (Freemont, Calif.) and Genpharm (San Jose, Calif.) can be engaged to provide human antibodies directed against a selected antigen using technology similar to that described above.

Completely human antibodies which recognize a selected epitope can be generated using a technique referred to as "guided selection". In this approach a selected non-human monoclonal antibody, e.g. a mouse antibody, is used to guide the selection of a completely human antibody recognizing the same epitope. (Jespers et al. (1994) Bio/technology 12:899-903).

The antibodies of the present invention can also be generated by the use of phage display technology to produce and screen libraries of polypeptides for binding to a selected target. See, e.g. Cwirla et al., *Proc. Natl. Acad. Sci. USA* 87, 6378-82, 1990; Devlin et al., *Science* 249, 404-6, 1990; Scott and Smith, *Science* 249, 386-88, 1990; and Ladner et al., U.S. Pat. No. 5,571,698. A basic concept of phage display methods is the establishment of a physical association between DNA encoding a polypeptide to be screened and the polypeptide. This physical association is provided by the phage particle, which displays a polypeptide as part of a capsid enclosing the phage genome which encodes the polypeptide. The establishment of a physical association between polypeptides and their genetic material allows simultaneous mass screening of very large numbers of phage bearing different polypeptides. Phage displaying a polypeptide with affinity to a target bind to the target and these phage are enriched by affinity screening to the target. The identity of polypeptides displayed from these phage can be determined from their respective genomes. Using these methods a polypeptide identified as having a binding affinity for a desired target can then be synthesized in bulk by conventional means. See, e.g. U.S. Pat. No. 6,057, 098, which is hereby incorporated in its entirety, including all tables, figures, and claims. In particular, such phage can be utilized to display antigen binding domains expressed from a repertoire or combinatorial antibody library (e.g. human or murine). Phage expressing an antigen binding domain that binds the antigen of interest can be selected or identified with antigen, e.g. using labelled antigen or antigen bound or captured to a solid surface or bead. Phage used in these methods are typically filamentous phage including fd and M13 binding domains expressed from phage with Fab, Fv or disulfide stabilized Fv antibody domains recombinantly fused to either the phage gene III or gene VIII protein. Phage display methods that can be used to make the antibodies of the present invention include those disclosed in Brinkman et al., J. Immunol. Methods 182:41-50 (1995); Ames et al., J. Immunol. Methods 184:177-186 (1995); Kettleborough et al., Eur. J. Immunol. 24:952-958 (1994); Persic et al., Gene 187 9-18 (1997); Burton et al., Advances in Immunology 57:191-280 (1994); PCT Application No. PCT/GB91/01134; PCT Publications WO 90/02809; WO 91/10737; WO 92/01047; WO 92/18619; WO 93/11236; WO 95/15982; WO 95/20401; and U.S. Pat. Nos. 5,698,426; 5,223,409; 5,403,484; 5,580,717; 5,427,908; 5,750,753; 5,821,047; 5,571,698; 5,427,908; 5,516,637; 5,780,225; 5,658,727; 5,733,743 and 5,969,108; each of which is incorporated herein by reference in its entirety.

As described in the above references, after phage selection, the antibody coding regions from the phage can be isolated and used to generate whole antibodies, including human antibodies, or any other desired antigen binding fragment, and expressed in any desired host, including mammalian cells, insect cells, plant cells, yeast, and bacteria, e.g. as described in detail below. For example, techniques to recombinantly produce Fab, Fab' and F(ab')$_2$ fragments can also be employed using methods known in the art such as those disclosed in PCT publication WO 92/22324; Mullinax et al., BioTechniques 12(6):864-869 (1992); and Sawai et al., AJRI 34:26-34 (1995); and Better et al., Science 240:1041-1043 (1988) (said references incorporated by reference in their entireties).

Examples of techniques which can be used to produce single-chain Fvs and antibodies include those described in U.S. Pat. Nos. 4,946,778 and 5,258,498; Huston et al., *Methods in Enzymology* 203:46-88 (1991); Shu et al., *PNAS* 90:7995-7999 (1993); and Skerra et al., *Science* 240:1038-1040 (1988).

The invention further provides for the use of bispecific antibodies, which can be made by methods known in the art. Traditional production of full length bispecific antibodies is based on the coexpression of two immunoglobulin heavy chain-light chain pairs, where the two chains have different specificities (Milstein et al., 1983, Nature 305:537-539). Because of the random assortment of immunoglobulin heavy and light chains, these hybridomas (quadromas) produce a potential mixture of 10 different antibody molecules, of which only one has the correct bispecific structure. Purification of the correct molecule, which is usually done by affinity chromatography steps, is rather cumbersome, and the product yields are low. Similar procedures are disclosed in WO 93/08829, published 13 May 1993, and in Traunecker et al., 1991, EMBO J. 10:3655-3659.

According to a different and more preferred approach, antibody variable domains with the desired binding specificities (antibody-antigen combining sites) are fused to immunoglobulin constant domain sequences. The fusion preferably is with an immunoglobulin heavy chain constant domain, comprising at least part of the hinge, CH2, and CH3 regions. It is preferred to have the first heavy-chain constant region (CH1) containing the site necessary for light chain binding, present in at least one of the fusions. DNAs encoding the immunoglobulin heavy chain fusions and, if desired, the immunoglobulin light chain, are inserted into separate expression vectors, and are co-transfected into a suitable host organism. This provides for great flexibility in adjusting the mutual proportions of the three polypeptide fragments in embodiments when unequal ratios of the three polypeptide chains used in the construction provide the optimum yields. It is, however, possible to insert the coding sequences for two or all three polypeptide chains in one expression vector when the expression of at least two polypeptide chains in equal ratios results in high yields or when the ratios are of no particular significance.

In a particular embodiment of this approach, the bispecific antibodies are composed of a hybrid immunoglobulin heavy chain with a first binding specificity in one arm, and a hybrid immunoglobulin heavy chain-light chain pair (providing a second binding specificity) in the other arm. It was found that this asymmetric structure facilitates the separation of the desired bispecific compound from unwanted immunoglobulin chain combinations, as the presence of an immunoglobulin light chain in only one half of the bispecific molecule provides for a facile way of separation. This approach is disclosed in WO 94/04690 published Mar. 3, 1994. For further details for generating bispecific antibodies see, for example, Suresh et al., Methods in Enzymology, 1986, 121: 210.

The invention provides functionally active fragments, derivatives or analogues of the anti-Ephrin type-A receptor 10 immunoglobulin molecules. Functionally active means that the fragment, derivative or analogue is able to elicit anti-anti-idiotype antibodies (i.e., tertiary antibodies) that recognize the same antigen that is recognized by the antibody from which the fragment, derivative or analogue is derived. Specifically, in a particular embodiment the antigenicity of the idiotype of the immunoglobulin molecule may be enhanced by deletion of framework and CDR sequences that are C-terminal to the CDR sequence that specifically recognizes the antigen. To determine which CDR sequences bind the antigen, synthetic peptides containing the CDR sequences can be used in binding assays with the antigen by any binding assay method known in the art.

The present invention provides antibody fragments such as, but not limited to, F(ab')$_2$ fragments and Fab fragments. Antibody fragments which recognize specific epitopes may be generated by known techniques. F(ab')$_2$ fragments consist of the variable region, the light chain constant region and the CH1 domain of the heavy chain and are generated by pepsin digestion of the antibody molecule. Fab fragments are generated by reducing the disulfide bridges of the F(ab')$_2$ fragments. The invention also provides heavy chain and light chain dimers of the antibodies of the invention, or any minimal fragment thereof such as Fvs or single chain antibodies (SCAs) (e.g. as described in U.S. Pat. No. 4,946,778; Bird, 1988, Science 242:423-42; Huston et al., 1988, Proc. Natl. Acad. Sci. USA 85:5879-5883; and Ward et al., 1989, Nature 334:544-54), or any other molecule with the same specificity as the antibody of the invention. Single chain antibodies are formed by linking the heavy and light chain fragments of the Fv region via an amino acid bridge, resulting in a single chain polypeptide. Techniques for the assembly of functional Fv fragments in *E. coli* may be used (Skerra et al., 1988, Science 242:1038-1041).

In other embodiments, the invention provides fusion proteins of the immunoglobulins of the invention (or functionally active fragments thereof), for example in which the immunoglobulin is fused via a covalent bond (e.g. a peptide bond), at either the N-terminus or the C-terminus to an amino acid sequence of another protein (or portion thereof, preferably at least 10, 20 or 50 amino acid portion of the protein) that is not the immunoglobulin. Preferably the immunoglobulin, or fragment thereof, is covalently linked to the other protein at the N-terminus of the constant domain. As stated above, such fusion proteins may facilitate purification, increase half-life in vivo, and enhance the delivery of an antigen across an epithelial barrier to the immune system.

The immunoglobulins of the invention include analogues and derivatives that are modified, i.e., by the covalent attachment of any type of molecule as long as such covalent attachment does not impair immunospecific binding. For example, but not by way of limitation, the derivatives and analogues of the immunoglobulins include those that have been further modified, e.g. by glycosylation, acetylation, pegylation, phosphylation, amidation, derivatization by known protecting/blocking groups, proteolytic cleavage, linkage to a cellular ligand or other protein, etc. Any of numerous chemical modifications may be carried out by known techniques, including, but not limited to specific chemical cleavage, acetylation, formylation, etc. Additionally, the analogue or derivative may contain one or more non-classical amino acids.

The foregoing antibodies can be used in methods known in the art relating to the localization and activity of Ephrin type-A receptor 10, e.g. for imaging this protein, measuring levels thereof in appropriate physiological samples, in diagnostic methods, etc.

Production of Affibodies to Ephrin Type-A Receptor 10

Affibody molecules represent a new class of affinity proteins based on a 58-amino acid residue protein domain, derived from one of the IgG-binding domains of staphylococcal protein A. This three helix bundle domain has been used as a scaffold for the construction of combinatorial phagemid libraries, from which Affibody variants that target the desired molecules can be selected using phage display technology (Nord K, Gunneriusson E, Ringdahl J, Stahl S, Uhlen M, Nygren P A, Binding proteins selected from combinatorial libraries of an α-helical bacterial receptor domain, Nat Biotechnol 1997; 15:772-7. Ronmark J, Gronlund H, Uhlen M, Nygren P A, Human immunoglobulin A (IgA)-specific ligands from combinatorial engineering of protein A, Eur J Biochem 2002; 269:2647-55.). The simple, robust structure of Affibody molecules in combination with their low molecular weight (6 kDa), make them suitable for a wide variety of applications, for instance, as detection reagents (Ronmark J, Hansson M, Nguyen T, et al, Construction and characterization of Affibody-Fc chimeras produced in *Escherichia coli*, J Immunol Methods 2002; 261:199-211) and to inhibit receptor interactions (Sandstorm K, Xu Z, Forsberg G, Nygren P A, Inhibition of the CD28-CD80 co-stimulation signal by a CD28-binding Affibody ligand developed by combinatorial protein engineering, Protein Eng 2003; 16:691-7). Further details of Affibodies and methods of production thereof may be obtained by reference to U.S. Pat. No. 5,831,012 which is herein incorporated by reference in its entirety.

Labelled Affibodies may also be useful in imaging applications for determining abundance of Isoforms.

Production of Domain Antibodies to Ephrin Type-A Receptor 10

References to antibodies herein embrace references to Domain Antibodies. Domain Antibodies (dAbs) are the smallest functional binding units of antibodies, corresponding to the variable regions of either the heavy ($V_H$) or light ($V_L$) chains of human antibodies. Domain Antibodies have a molecular weight of approximately 13 kDa. Domantis has developed a series of large and highly functional libraries of fully human $V_H$ and $V_L$ dAbs (more than ten billion different sequences in each library), and uses these libraries to select dAbs that are specific to therapeutic targets. In contrast to many conventional antibodies, Domain Antibodies are well expressed in bacterial, yeast, and mammalian cell systems. Further details of domain antibodies and methods of production thereof may be obtained by reference to U.S. Pat. Nos. 6,291,158; 6,582,915; 6,593,081; 6,172,197; 6,696,245; US Serial No. 2004/0110941; European patent application No. 1433846 and European Patents 0368684 & 0616640; WO05/035572, WO04/101790, WO04/081026, WO04/058821, WO04/003019 and WO03/002609, each of which is herein incorporated by reference in its entirety.

Production of Nanobodies to Ephrin Type-A Receptor 10

Nanobodies are antibody-derived therapeutic proteins that contain the unique structural and functional properties of naturally-occurring heavy-chain antibodies. These heavy-chain antibodies contain a single variable domain (VHH) and two constant domains ($C_H2$ and $C_H3$). Importantly, the cloned and isolated VHH domain is a perfectly stable polypeptide harbouring the full antigen-binding capacity of the original heavy-chain antibody. Nanobodies have a high homology with the VH domains of human antibodies and can be further humanised without any loss of activity. Importantly, Nanobodies have a low immunogenic potential, which has been confirmed in primate studies with Nanobody lead compounds.

Nanobodies combine the advantages of conventional antibodies with important features of small molecule drugs. Like conventional antibodies, Nanobodies show high target specificity, high affinity for their target and low inherent toxicity. However, like small molecule drugs they can inhibit enzymes and readily access receptor clefts. Furthermore, Nanobodies are extremely stable, can be administered by means other than injection (see e.g. WO 04/041867, which is herein incorporated by reference in its entirety) and are easy to manufacture. Other advantages of Nanobodies include recognising uncommon or hidden epitopes as a result of their small size, binding into cavities or active sites of protein targets with high affinity and selectivity due to their unique 3-dimensional, drug format flexibility, tailoring of half-life and ease and speed of drug discovery.

Nanobodies are encoded by single genes and are efficiently produced in almost all prokaryotic and eukaryotic hosts e.g. *E. coli* (see e.g. U.S. Pat. No. 6,765,087, which is herein incorporated by reference in its entirety), moulds (for example *Aspergillus* or *Trichoderma*) and yeast (for example *Saccharomyces, Kluyveromyces, Hansenula* or *Pichia*) (see e.g. U.S. Pat. No. 6,838,254, which is herein incorporated by reference in its entirety). The production process is scalable and multi-kilogram quantities of Nanobodies have been produced. Because Nanobodies exhibit a superior stability compared with conventional antibodies, they can be formulated as a long shelf-life, ready-to-use solution.

The Nanoclone method (see e.g. WO 06/079372, which is herein incorporated by reference in its entirety) is a proprietary method for generating Nanobodies against a desired target, based on automated high-throughput selection of B-cells.

Production of UniBodies to Ephrin Type-A Receptor 10

UniBodies are another antibody fragment technology; however this one is based upon the removal of the hinge region of IgG4 antibodies. The deletion of the hinge region results in a molecule that is essentially half the size of traditional IgG4 antibodies and has a univalent binding region rather than the bivalent binding region of IgG4 antibodies. It is also well known that IgG4 antibodies are inert and thus do not interact with the immune system, which may be advantageous for the treatment of diseases where an immune response is not desired, and this advantage is passed onto UniBodies. For example, UniBodies may function to inhibit or silence, but not kill, the cells to which they are bound. Additionally, UniBody binding to cancer cells do not stimulate them to proliferate. Furthermore, because UniBodies are about half the size of traditional IgG4 antibodies, they may show better distribution over larger solid tumours with potentially advantageous efficacy. UniBodies are cleared from the body at a similar rate to whole IgG4 antibodies and are able to bind with a similar affinity for their antigens as whole antibodies. Further details of UniBodies may be obtained by reference to patent WO2007/059782, which is herein incorporated by reference in its entirety.

Production of DARPins to Ephrin Type-A Receptor 10

DARPins (Designed Ankyrin Repeat Proteins) are one example of an antibody mimetic DRP (Designed Repeat Protein) technology that has been developed to exploit the binding abilities of non-antibody polypeptides. Repeat proteins such as ankyrin or leucine-rich repeat proteins, are ubiquitous binding molecules, which occur, unlike antibodies, intra- and extracellularly. Their unique modular architecture features repeating structural units (repeats), which stack together to form elongated repeat domains displaying variable and modular target-binding surfaces. Based on this modularity, combinatorial libraries of polypeptides with highly diversified binding specificities can be generated. This strategy includes the consensus design of self-compatible repeats displaying variable surface residues and their random assembly into repeat domains.

DARPins can be produced in bacterial expression systems at very high yields and they belong to the most stable proteins known. Highly specific, high-affinity DARPins to a broad range of target proteins, including human receptors, cytokines, kinases, human proteases, viruses and membrane proteins, have been selected. DARPins having affinities in the single-digit nanomolar to picomolar range can be obtained. DARPins have been used in a wide range of applications, including ELISA, sandwich ELISA, flow cytometric analysis (FACS), immunohistochemistry (IHC), chip applications, affinity purification or Western blotting. DARPins also proved to be highly active in the intracellular compartment for example as intracellular marker proteins fused to green fluorescent protein (GFP). DARPins were further used to inhibit viral entry with IC50 in the pM range. DARPins are not only ideal to block protein-protein interactions, but also to inhibit enzymes. Proteases, kinases and transporters have been successfully inhibited, most often an allosteric inhibition mode. Very fast and specific enrichments on the tumour and very favourable tumour to blood ratios make DARPins well suited for in vivo diagnostics or therapeutic approaches.

Additional information regarding DARPins and other DRP technologies can be found in US Patent Application Publication No. 2004/0132028, and International Patent Application Publication No. WO 02/20565, both of which are hereby incorporated by reference in their entirety.

Production of Anticalins to Ephrin Type-A Receptor 10

Anticalins are an additional antibody mimetic technology, however in this case the binding specificity is derived from lipocalins, a family of low molecular weight proteins that are naturally and abundantly expressed in human tissues and body fluids. Lipocalins have evolved to perform a range of functions in vivo associated with the physiological transport and storage of chemically sensitive or insoluble compounds. Lipocalins have a robust intrinsic structure comprising a highly conserved β-barrel which supports four loops at one terminus of the protein. These loops form the entrance to a binding pocket and conformational differences in this part of the molecule account for the variation in binding specificity between individual lipocalins.

While the overall structure of hypervariable loops supported by a conserved β-sheet framework is reminiscent of immunoglobulins, lipocalins differ considerably from antibodies in terms of size, being composed of a single polypeptide chain of 160-180 amino acids which is marginally larger than a single immunoglobulin domain.

Lipocalins are cloned and their loops are subjected to engineering in order to create Anticalins. Libraries of structurally diverse Anticalins have been generated and Anticalin display allows the selection and screening of binding function, followed by the expression and production of soluble protein for further analysis in prokaryotic or eukaryotic systems. Studies have successfully demonstrated that Anticalins can be developed that are specific for virtually any human target protein; they can be isolated and binding affinities in the nanomolar or higher range can be obtained.

Anticalins can also be formatted as dual targeting proteins, so-called Duocalins. A Duocalin binds two separate therapeutic targets in one easily produced monomeric protein using standard manufacturing processes while retaining target specificity and affinity regardless of the structural orientation of its two binding domains.

Modulation of multiple targets through a single molecule is particularly advantageous in diseases known to involve more than a single causative factor. Moreover, bi- or multivalent binding formats such as Duocalins have significant potential in targeting cell surface molecules in disease, mediating agonistic effects on signal transduction pathways or inducing enhanced internalization effects via binding and clustering of cell surface receptors. Furthermore, the high intrinsic stability of Duocalins is comparable to monomeric Anticalins, offering flexible formulation and delivery potential for Duocalins.

Additional information regarding Anticalins can be found in U.S. Pat. No. 7,250,297 and International Patent Application Publication No. WO 99/16873, both of which are hereby incorporated by reference in their entirety.

Production of Avimers to Ephrin Type-A Receptor 10

Avimers are evolved from a large family of human extracellular receptor domains by in vitro exon shuffling and phage display, generating multidomain proteins with binding and inhibitory properties Linking multiple independent binding domains has been shown to create avidity and results in improved affinity and specificity compared with conventional single-epitope binding proteins. Other potential advantages include simple and efficient production of multitarget-specific molecules in *Escherichia coli*, improved thermostability and resistance to proteases. Avimers with sub-nanomolar affinities have been obtained against a variety of targets.

Additional information regarding Avimers can be found in US Patent Application Publication Nos. 2006/0286603, 2006/0234299, 2006/0223114, 2006/0177831, 2006/0008844, 2005/0221384, 2005/0164301, 2005/0089932, 2005/0053973, 2005/0048512, 2004/0175756, all of which are hereby incorporated by reference in their entirety.

Production of Versabodies to Ephrin Type-A Receptor 10

Versabodies are small proteins of 3-5 kDa with >15% cysteines, which form a high disulfide density scaffold, replacing the hydrophobic core that typical proteins have. The replacement of a large number of hydrophobic amino acids, comprising the hydrophobic core, with a small number of disulfides results in a protein that is smaller, more hydrophilic (less aggregation and non-specific binding), more resistant to proteases and heat, and has a lower density of T-cell epitopes, because the residues that contribute most to MHC presentation are hydrophobic. All four of these properties are well-known to affect immunogenicity, and together they are expected to cause a large decrease in immunogenicity.

The inspiration for Versabodies comes from the natural injectable biopharmaceuticals produced by leeches, snakes, spiders, scorpions, snails, and anemones, which are known to exhibit unexpectedly low immunogenicity. Starting with selected natural protein families, by design and by screening the size, hydrophobicity, proteolytic antigen processing, and epitope density are minimized to levels far below the average for natural injectable proteins.

Given the structure of Versabodies, these antibody mimetics offer a versatile format that includes multi-valency, multi-specificity, a diversity of half-life mechanisms, tissue targeting modules and the absence of the antibody Fc region. Furthermore, Versabodies are manufactured in *E. coli* at high yields, and because of their hydrophilicity and small size, Versabodies are highly soluble and can be formulated to high concentrations. Versabodies are exceptionally heat stable (they can be boiled) and offer extended shelf-life.

Additional information regarding Versabodies can be found in US Patent Application Publication No. 2007/0191272 which is hereby incorporated by reference in its entirety.

Expression of Affinity Reagents

Expression of Antibodies

The antibodies of the invention can be produced by any method known in the art for the synthesis of antibodies, in particular, by chemical synthesis or by recombinant expression, and are preferably produced by recombinant expression techniques.

Recombinant expression of antibodies, or fragments, derivatives or analogues thereof, requires construction of a nucleic acid that encodes the antibody. If the nucleotide sequence of the antibody is known, a nucleic acid encoding the antibody may be assembled from chemically synthesized oligonucleotides (e.g. as described in Kutmeier et al., 1994, BioTechniques 17:242), which, briefly, involves the synthesis of overlapping oligonucleotides containing portions of the sequence encoding antibody, annealing and ligation of those oligonucleotides, and then amplification of the ligated oligonucleotides by PCR.

Alternatively, the nucleic acid encoding the antibody may be obtained by cloning the antibody. If a clone containing the nucleic acid encoding the particular antibody is not available, but the sequence of the antibody molecule is known, a nucleic acid encoding the antibody may be obtained from a suitable source (e.g. an antibody cDNA library, or cDNA library generated from any tissue or cells expressing the antibody) by PCR amplification using synthetic primers hybridisable to the 3' and 5' ends of the sequence or by cloning using an oligonucleotide probe specific for the particular gene sequence.

If an antibody molecule that specifically recognizes a particular antigen is not available (or a source for a cDNA library for cloning a nucleic acid encoding such an antibody), antibodies specific for a particular antigen may be generated by any method known in the art, for example, by immunizing an animal, such as a rabbit, to generate polyclonal antibodies or, more preferably, by generating monoclonal antibodies. Alternatively, a clone encoding at least the Fab portion of the antibody may be obtained by screening Fab expression libraries (e.g. as described in Huse et al., 1989, *Science* 246:1275-1281) for clones of Fab fragments that bind the specific antigen or by screening antibody libraries (See, e.g. Clackson et al., 1991, Nature 352:624; Hane et al., 1997 Proc. Natl. Acad. Sci. USA 94:4937).

Once a nucleic acid encoding at least the variable domain of the antibody molecule is obtained, it may be introduced into a vector containing the nucleotide sequence encoding the constant region of the antibody molecule (see, e.g. PCT Publication WO 86/05807; PCT Publication WO 89/01036; and U.S. Pat. No. 5,122,464). Vectors containing the complete light or heavy chain for co-expression with the nucleic acid to allow the expression of a complete antibody molecule are also available. Then, the nucleic acid encoding the antibody can be used to introduce the nucleotide substitution(s) or deletion(s) necessary to substitute (or delete) the one or more variable region cysteine residues participating in an intrachain disulfide bond with an amino acid residue that does not contain a sulfhydyl group. Such modifications can be carried out by any method known in the art for the introduction of specific mutations or deletions in a nucleotide sequence, for example, but not limited to, chemical mutagenesis, in vitro site directed mutagenesis (Hutchinson et al., 1978, J. Biol. Chem. 253: 6551), PCT based methods, etc.

In addition, techniques developed for the production of "chimeric antibodies" (Morrison et al., 1984, Proc. Natl. Acad. Sci. 81:851-855; Neuberger et al., 1984, Nature 312: 604-608; Takeda et al., 1985, Nature 314:452-454) by splicing genes from a mouse antibody molecule of appropriate antigen specificity together with genes from a human antibody molecule of appropriate biological activity can be used. As described supra, a chimeric antibody is a molecule in which different portions are derived from different animal species, such as those having a variable region derived from a murine mAb and a human antibody constant region, e.g. humanized antibodies.

Once a nucleic acid encoding an antibody molecule of the invention has been obtained, the vector for the production of the antibody molecule may be produced by recombinant DNA technology using techniques well known in the art. Thus, methods for preparing the protein of the invention by expressing nucleic acid containing the antibody molecule sequences are described herein. Methods which are well known to those skilled in the art can be used to construct expression vectors containing an antibody molecule coding sequences and appropriate transcriptional and translational control signals. These methods include, for example, in vitro recombinant DNA techniques, synthetic techniques, and in vivo genetic recombination. See, for example, the techniques described in Sambrook et al. (1990, Molecular Cloning, A Laboratory Manual, 2$^{nd}$ Ed., Cold Spring Harbor Laboratory, Cold Spring Harbor, N.Y.) and Ausubel et al. (eds., 1998, Current Protocols in Molecular Biology, John Wiley & Sons, NY).

The expression vector is transferred to a host cell by conventional techniques and the transfected cells are then cultured by conventional techniques to produce an antibody of the invention.

The host cells used to express a recombinant antibody of the invention may be either bacterial cells such as *Escherichia coli*, or, preferably, eukaryotic cells, especially for the expression of whole recombinant antibody molecule. In particular, mammalian cells such as Chinese hamster ovary cells (CHO), in conjunction with a vector such as the major intermediate early gene promoter element from human cytomegalovirus are an effective expression system for antibodies (Foecking et al., 1986, Gene 45:101; Cockett et al., 1990, Bio/Technology 8:2).

A variety of host-expression vector systems may be utilized to express an antibody molecule of the invention. Such host-expression systems represent vehicles by which the coding sequences of interest may be produced and subsequently purified, but also represent cells which may, when transformed or transfected with the appropriate nucleotide coding sequences, express the antibody molecule of the invention in situ. These include but are not limited to microorganisms such as bacteria (e.g. *E. coli, B. subtilis*) transformed with recombinant bacteriophage DNA, plasmid DNA or cosmid DNA expression vectors containing antibody coding sequences; yeast (e.g. *Saccharomyces, Pichia*) transformed with recombinant yeast expression vectors containing antibody coding sequences; insect cell systems infected with recombinant virus expression vectors (e.g. baculovirus) containing the antibody coding sequences; plant cell systems infected with recombinant virus expression vectors (e.g. cauliflower mosaic virus, CaMV; tobacco mosaic virus, TMV) or transformed with recombinant plasmid expression vectors (e.g. Ti plasmid) containing antibody coding sequences; or mammalian cell systems (e.g. COS, CHO, BHK, 293, 3T3 cells) harbouring recombinant expression constructs containing promoters derived from the genome of mammalian cells (e.g. metallothionein promoter) or from mammalian viruses (e.g. the adenovirus late promoter; the vaccinia virus 7.5K promoter).

In bacterial systems, a number of expression vectors may be advantageously selected depending upon the use intended for the antibody molecule being expressed. For example, when a large quantity of such a protein is to be produced, for the generation of pharmaceutical compositions comprising an antibody molecule, vectors which direct the expression of high levels of fusion protein products that are readily purified may be desirable. Such vectors include, but are not limited to, the *E. coli* expression vector pUR278 (Ruther et al., 1983, EMBO J. 2:1791), in which the antibody coding sequence may be ligated individually into the vector in frame with the lac Z coding region so that a fusion protein is produced; pIN vectors (Inouye & Inouye, 1985, *Nucleic Acids Res.* 13:3101-3109; Van Heeke & Schuster, 1989, J. Biol. Chem. 24:5503-5509); and the like. pGEX vectors may also be used to express foreign polypeptides as fusion proteins with glutathione S-transferase (GST). In general, such fusion proteins are soluble and can easily be purified from lysed cells by adsorption and binding to a matrix glutathione-agarose beads followed by elution in the presence of free glutathione. The pGEX vectors are designed to include thrombin or factor Xa protease cleavage sites so that the cloned target gene product can be released from the GST moiety.

In an insect system, *Autographa californica* nuclear polyhedrosis virus (AcNPV) is used as a vector to express foreign genes. The virus grows in *Spodoptera frugiperda* cells. The antibody coding sequence may be cloned individually into non-essential regions (for example the polyhedrin gene) of the virus and placed under control of an AcNPV promoter (for example the polyhedrin promoter). In mammalian host cells, a number of viral-based expression systems (e.g. an adenovirus expression system) may be utilized.

As discussed above, a host cell strain may be chosen which modulates the expression of the inserted sequences, or modifies and processes the gene product in the specific fashion desired. Such modifications (e.g. glycosylation) and processing (e.g. cleavage) of protein products may be important for the function of the protein.

For long-term, high-yield production of recombinant antibodies, stable expression is preferred. For example, cell lines that stably express an antibody of interest can be produced by transfecting the cells with an expression vector comprising the nucleotide sequence of the antibody and the nucleotide sequence of a selectable (e.g. neomycin or hygromycin), and selecting for expression of the selectable marker. Such engineered cell lines may be particularly useful in screening and evaluation of compounds that interact directly or indirectly with the antibody molecule.

The expression levels of the antibody molecule can be increased by vector amplification (for a review, see Bebbington and Hentschel, The use of vectors based on gene amplification for the expression of cloned genes in mammalian cells in DNA cloning, Vol. 3. (Academic Press, New York, 1987)). When a marker in the vector system expressing antibody is amplifiable, increase in the level of inhibitor present in culture of host cell will increase the number of copies of the marker gene. Since the amplified region is associated with the antibody gene, production of the antibody will also increase (Crouse et al., 1983, Mol. Cell. Biol. 3:257).

The host cell may be co-transfected with two expression vectors of the invention, the first vector encoding a heavy chain derived polypeptide and the second vector encoding a light chain derived polypeptide. The two vectors may contain identical selectable markers which enable equal expression of heavy and light chain polypeptides. Alternatively, a single vector may be used which encodes both heavy and light chain polypeptides. In such situations, the light chain should be placed before the heavy chain to avoid an excess of toxic free heavy chain (Proudfoot, 1986, Nature 322:52; Kohler, 1980, Proc. Natl. Acad. Sci. USA 77:2197). The coding sequences for the heavy and light chains may comprise cDNA or genomic DNA.

Once the antibody molecule of the invention has been recombinantly expressed, it may be purified by any method known in the art for purification of an antibody molecule, for example, by chromatography (e.g. ion exchange chromatography, affinity chromatography such as with protein A or specific antigen, and sizing column chromatography), centrifugation, differential solubility, or by any other standard technique for the purification of proteins.

Alternatively, any fusion protein may be readily purified by utilizing an antibody specific for the fusion protein being expressed. For example, a system described by Janknecht et al. allows for the ready purification of non-denatured fusion proteins expressed in human cell lines (Janknecht et al., 1991, Proc. Natl. Acad. Sci. USA 88:8972-897). In this system, the gene of interest is subcloned into a vaccinia recombination plasmid such that the open reading frame of the gene is translationally fused to an amino-terminal tag consisting of six histidine residues. The tag serves as a matrix binding domain for the fusion protein. Extracts from cells infected with recombinant vaccinia virus are loaded onto $Ni^{2+}$ nitrilo-acetic acid-agarose columns and histidine-tagged proteins are selectively eluted with imidazole-containing buffers.

The antibodies that are generated by these methods may then be selected by first screening for affinity and specificity with the purified polypeptide of interest and, if required, comparing the results to the affinity and specificity of the antibodies with polypeptides that are desired to be excluded from binding. The screening procedure can involve immobilization of the purified polypeptides in separate wells of microtiter plates. The solution containing a potential antibody or groups of antibodies is then placed into the respective microtiter wells and incubated for about 30 min to 2 h. The microtiter wells are then washed and a labelled secondary antibody (for example, an anti-mouse antibody conjugated to alkaline phosphatase if the raised antibodies are mouse antibodies) is added to the wells and incubated for about 30 min and then washed. Substrate is added to the wells and a colour reaction will appear where antibody to the immobilized polypeptide(s) is present.

The antibodies so identified may then be further analyzed for affinity and specificity in the assay design selected. In the development of immunoassays for a target protein, the purified target protein acts as a standard with which to judge the sensitivity and specificity of the immunoassay using the antibodies that have been selected. Because the binding affinity of various antibodies may differ; certain antibody pairs (e.g. in sandwich assays) may interfere with one another sterically, etc., assay performance of an antibody may be a more important measure than absolute affinity and specificity of an antibody.

Those skilled in the art will recognize that many approaches can be taken in producing antibodies or binding fragments and screening and selecting for affinity and specificity for the various polypeptides, but these approaches do not change the scope of the invention.

For therapeutic applications, antibodies (particularly monoclonal antibodies) may suitably be human or humanized animal (e.g. mouse) antibodies. Animal antibodies may be raised in animals using the human protein (e.g. Ephrin type-A receptor 10) as immunogen. Humanisation typically involves grafting CDRs identified thereby into human framework regions. Normally some subsequent retromutation to optimize the conformation of chains is required. Such processes are known to persons skilled in the art.

Expression of Affibodies

The construction of Affibodies has been described elsewhere (Ronnmark J, Gronlund H, Uhlen, M., Nygren P. A, Human immunoglobulin A (IgA)-specific ligands from combinatorial engineering of protein A, 2002, Eur. J. Biochem. 269, 2647-2655.), including the construction of Affibody phage display libraries (Nord, K., Nilsson, J., Nilsson, B., Uhlen, M. & Nygren, P. A, A combinatorial library of an a-helical bacterial receptor domain, 1995, Protein Eng. 8, 601-608. Nord, K., Gunneriusson, E., Ringdahl, J., Stahl, S., Uhlen, M. & Nygren, P. A, Binding proteins selected from combinatorial libraries of an a-helical bacterial receptor domain, 1997, Nat. Biotechnol. 15, 772-777.)

The biosensor analyses to investigate the optimal Affibody variants using biosensor binding studies has also been described elsewhere (Ronnmark J, Gronlund H, Uhlen, M., Nygren P. A, Human immunoglobulin A (IgA)-specific ligands from combinatorial engineering of protein A, 2002, Eur. J. Biochem. 269, 2647-2655.).

Affinity Reagent Modifications

In a particular embodiment, anti-Ephrin type-A receptor 10 affinity reagents such as antibodies or fragments thereof are conjugated to a diagnostic moiety (such as a detectable label) or a therapeutic moiety. The antibodies can be used for diagnosis or to determine the efficacy of a given treatment regimen. Detection can be facilitated by coupling the antibody to a detectable substance (label). Examples of detectable substances include various enzymes, prosthetic groups, fluorescent materials, luminescent materials, bioluminescent materials, radioactive nuclides, positron emitting metals (for use in positron emission tomography), and nonradioactive paramagnetic metal ions. See generally U.S. Pat. No. 4,741, 900 for metal ions which can be conjugated to antibodies for use as diagnostics according to the present invention. Suitable enzymes include horseradish peroxidase, alkaline phosphatase, beta-galactosidase, or acetylcholinesterase; suitable prosthetic groups include streptavidin, avidin and biotin; suitable fluorescent materials include umbelliferone, fluorescein, fluorescein isothiocyanate, rhodamine, dichlorotriazinylamine fluorescein, dansyl chloride and phycoerythrin; suitable luminescent materials include luminol; suitable bioluminescent materials include luciferase, luciferin, and aequorin; and suitable radioactive nuclides include $^{125}$I, $^{131}$, $^{111}$In and $^{99}$Tc. $^{68}$Ga may also be employed.

Anti-Ephrin type-A receptor 10 antibodies or fragments thereof as well as other affinity reagents can be conjugated to a therapeutic agent or drug moiety to modify a given biological response. An exemplary therapeutic agent to which the affinity reagent may be conjugated is a cytotoxic moiety. The therapeutic agent or drug moiety is not to be construed as limited to classical chemical therapeutic agents. For example, the drug moiety may be a protein or polypeptide possessing a desired biological activity. Such proteins may include, for example, a toxin such as abrin, ricin A, pseudomonas exotoxin, or diphtheria toxin; a protein such as tumour necrosis factor, α-interferon, β-interferon, nerve growth factor, platelet derived growth factor, tissue plasminogen activator, a thrombotic agent or an anti-angiogenic agent, e.g. angiostatin or endostatin; or, a biological response modifier such as a lymphokine, interleukin-1 (IL-1), interleukin-2 (IL-2), interleukin-6 (IL-6), granulocyte macrophage colony stimulating factor (GM-CSF), granulocyte colony stimulating factor (G-CSF), nerve growth factor (NGF) or other growth factor.

Techniques for conjugating such therapeutic moiety to antibodies are well known, see, e.g. Arnon et al., "Monoclonal Antibodies For Immunotargeting Of Drugs In Cancer Therapy", in Monoclonal Antibodies And Cancer Therapy, Reisfeld et al. (eds.), pp. 243-56 (Alan R. Liss, Inc. 1985); Hellstrom et al., "Antibodies For Drug Delivery", in Controlled Drug Delivery (2$^{nd}$ Ed.), Robinson et al. (eds.), pp. 623-53 (Marcel Dekker, Inc. 1987); Thorpe, "Antibody Carriers Of Cytotoxic Agents In Cancer Therapy: A Review", in Monoclonal Antibodies '84: Biological And Clinical Applications, Pinchera et al. (eds.), pp. 475-506 (1985); "Analysis, Results, And Future Prospective Of The Therapeutic Use Of Radiolabeled Antibody In Cancer Therapy", in Monoclonal Antibodies For Cancer Detection And Therapy, Baldwin et al. (eds.), pp. 303-16 (Academic Press 1985), and Thorpe et al., "The Preparation And Cytotoxic Properties Of Antibody-Toxin Conjugates", Immunol. Rev., 62:119-58 (1982).

Alternatively, an antibody can be conjugated to a second antibody to form an antibody heteroconjugate as described by Segal in U.S. Pat. No. 4,676,980.

An antibody with or without a therapeutic moiety conjugated to it can be used as a therapeutic that is administered alone or in combination with cytotoxic factor(s) and/or cytokine(s).

The invention also provides for fully human, or humanised antibodies that induce antibody-directed cell-mediated cytotoxicity (ADCC). A fully human antibody is one in which the protein sequences are encoded by naturally occurring human immunoglobulin sequences, either from isolated antibody-producing human B-lymphocytes, or from transgenic murine B-lymphocytes of mice in which the murine immunoglobulin coding chromosomal regions have been replaced by orthologous human sequences. Transgenic antibodies of the latter type include, but are not restricted to, HuMab (Medarex, Inc, CA) and Xenomouse (Abgenix Inc., CA). A humanised antibody is one in which the constant region of a non-human antibody molecule of appropriate antigen specificity, is replaced by the constant region of a human antibody, preferably of the IgG subtype, with appropriate effector functions (Morrison et al., 1984, Proc. Natl. Acad. Sci. 81:851-855; Neuberger et al., 1984, Nature 312:604-608; Takeda et al., 1985, Nature 314:452-454). Appropriate effector functions include ADCC, which is a natural process by which fully-human antibodies or humanized antibodies, when bound to targets on the surface of cancer cells, switch on the cell killing properties of lymphocytes that are part of the normal immune system. These active lymphocytes, called Natural Killer (NK) cells, use a cytotoxic process to destroy living cells to which the antibodies are bound. ADCC activity may be detected and quantified by measuring release of Europium (Eu3+) from Eu3+ labelled, living cells in the presence of an antigen-specific antibody and peripheral blood mononuclear cells extracted from an immunocompetent, living human subject. The ADCC process is described in detail in Janeway Jr. C. A. et al., Immunobiology, 5th ed., 2001, Garland Publishing, ISBN 0-8153-3642-X; Pier G. B. et al., Immunology, Infection, and Immunity, 2004, p 246-5; Albanell J. et al., Advances in Experimental Medicine and Biology, 2003, 532: p 2153-68 and Weng, W.-K. et al., Journal of Clinical Oncology, 2003, 21: p 3940-3947. Suitable methods for the detection and quantification of ADCC can be found in Blomberg et al., Journal of Immunological Methods. 1986, 86: p 225-9; Blomberg et al., Journal of Immunological Methods. 1986, 21; 92: p 117-23 and Patel & Boyd, Journal of Immunological Methods. 1995, 184: p 29-38.

ADCC typically involves activation of NK cells and is dependent on the recognition of antibody-coated cells by Fc receptors on the surface of the NK cell. The Fc receptors recognize the Fc (crystalline) portion of antibodies such as IgG, bound specifically to the surface of a target cell. The Fc receptor that triggers activation of the NK cell is called CD16 or FcγRIIIa. Once the FcγRIIIa receptor is bound to the IgG Fc, the NK cell releases cytokines such as IFN-γ, and cytotoxic granules containing perforin and granzymes that enter the target cell and promote cell death by triggering apoptosis.

The induction of antibody-dependent cellular cytotoxicity (ADCC) by an antibody can be enhanced by modifications that alter interactions between the antibody constant region (Fc) and various receptors that are present on the surface of cells of the immune system. Such modifications include the reduction or absence of alpha1,6-linked fucose moieties in the complex oligosaccharide chains that are normally added to the Fc of antibodies during natural or recombinant synthesis in mammalian cells. In a preferred embodiment, non-fucosylated anti-Ephrin type-A receptor 10 affinity reagents such as antibodies or fragments thereof are produced for the purpose of enhancing their ability to induce the ADCC response.

Techniques for reducing or ablating alpha1,6-linked fucose moieties in the oligosaccharide chains of the Fc are well established. In one example, the recombinant antibody is synthesized in a cell line that is impaired in its ability to add fucose in an alpha 1,6 linkage to the innermost N-acetylglucosamine of the N-linked biantennary complex-type Fc oligosaccharides. Such cell lines include, but are not limited to, the rat hybridoma YB2/0, which expresses a reduced level of the alpha 1,6-fucosyltransferase gene, FUT8. Preferably, the antibody is synthesized in a cell line that is incapable of adding alpha 1,6-linked fucosyl moieties to complex oligosaccharide chains, due to the deletion of both copies of the FUT8 gene. Such cell lines include, but are not limited to, FUT8−/− CHO/DG44 cell lines. Techniques for synthesizing partially fucosylated, or non-fucosylated antibodies and affinity reagents are described in Shinkawa et al., J. Biol. Chem. 278:3466-34735 (2003); Yamane-Ohnuki et al., Biotechnology and Bioengineering 87: 614-22 (2004) and in WO00/61739 A1, WO02/31140 A1 and WO03/085107 A1. In a second example, the fucosylation of a recombinant antibody is reduced or abolished by synthesis in a cell line that has been genetically engineered to overexpress a glycoprotein-modifying glycosyl transferase at a level that maximizes the production of complex N-linked oligosaccharides carrying bisecting N-acetylglucosamine. For example, the antibody is synthesized in a Chinese Hamster Ovary cell line expressing the enzyme N-acetyl glucosamine transferase III (GnT III). Cell lines stably transfected with suitable glycoprotein-modifying glycosyl transferases, and methods of synthesizing antibodies using these cells are described in WO9954342.

A non-fucosylated antibody or affinity reagent can be used as a therapeutic that is administered alone or in combination with cytotoxic factor(s) and/or cytokine(s).

In a further modification, the amino acid sequences of the antibody Fc are altered in a way that enhances ADCC activation, without affecting ligand affinity. Examples of such modifications are described in Lazar et al., Proceedings of the National Academy of Sciences 2006, 103: p 4005-4010; WO03074679 and WO2007039818. In these examples, substitution of amino acids in the antibody Fc, such as aspartate for serine at position 239, and isoleucine for glutamate at position 332, altered the binding affinity of an antibody for Fc receptors, leading to an increase in ADCC activation.

An antibody reagent with enhanced ADCC activation due to amino acid substitutions can be used as a therapeutic that is administered alone or in combination with cytotoxic factor(s) and/or cytokine(s).

Diagnosis of Bladder Cancer, Breast Cancer, Colorectal Cancer, Head and Neck Cancer, Kidney Cancer, Lung Cancer or Pancreatic Cancer In accordance with the present invention, test samples of bladder, breast, colorectal, head and neck, kidney, lung or pancreatic tissue, serum, plasma or urine obtained from a subject suspected of having or known to have bladder cancer, breast cancer, colorectal cancer, head and neck cancer, kidney cancer, lung cancer or pancreatic cancer can be used for diagnosis or monitoring. In one embodiment, a change in the abundance of Ephrin type-A receptor 10 in a test sample relative to a control sample (from a subject or subjects free from bladder cancer, breast cancer, colorectal cancer, head and neck cancer, kidney cancer, lung cancer and pancreatic cancer) or a previously determined reference range indicates the presence of bladder cancer, breast cancer, colorectal cancer, head and neck cancer, kidney cancer, lung cancer or pancreatic cancer. In another embodiment, the relative abundance of Ephrin type-A receptor 10 in a test sample compared to a control sample or a previously determined reference range indicates a subtype of bladder cancer, breast cancer, colorectal cancer, head and neck cancer, kidney cancer, lung cancer or pancreatic cancer (e.g. squamous cell bladder cancer; inflammatory breast cancer; familial or sporadic colorectal cancer; nasopharyngeal cancer; transitional cell kidney carcinoma; squamous cell lung carcinoma or endocrine tumours of the pancreas). In yet another embodiment, the relative abundance of Ephrin type-A receptor 10 in a test sample relative to a control sample or a previously determined reference range indicates the degree or severity of bladder cancer, breast cancer, colorectal cancer, head and neck cancer, kidney cancer, lung cancer or pancreatic cancer (e.g. the likelihood for metastasis). In any of the aforesaid methods, detection of Ephrin type-A receptor 10 may optionally be combined with detection of one or more of additional biomarkers for bladder cancer, breast cancer, colorectal cancer, head and neck cancer, kidney cancer, lung cancer or pancreatic cancer. Any suitable method in the art can be employed to measure the level of Ephrin type-A receptor 10, including but not limited to the Preferred Technologies described herein, kinase assays, immunoassays to detect and/or visualize the Ephrin type-A receptor 10 (e.g. Western blot, immunoprecipitation followed by sodium dodecyl sulfate polyacrylamide gel electrophoresis, immunocytochemistry, etc.). In a further embodiment, a change in the abundance of mRNA encoding Ephrin type-A receptor 10 in a test sample relative to a control sample or a previously determined reference range indicates the presence of bladder cancer, breast cancer, colorectal cancer, head and neck cancer, kidney cancer, lung cancer or pancreatic cancer. Any suitable hybridization assay can be used to detect Ephrin type-A receptor 10 expression by detecting and/or visualizing mRNA encoding the Ephrin type-A receptor 10 (e.g. Northern assays, dot blots, in situ hybridization, etc.).

In another embodiment of the invention, labelled antibodies (or other affinity reagents), derivatives and analogues thereof, which specifically bind to Ephrin type-A receptor 10 can be used for diagnostic purposes to detect, diagnose, or monitor bladder cancer, breast cancer, colorectal cancer, head and neck cancer, kidney cancer, lung cancer or pancreatic cancer. For example, bladder cancer, breast cancer, colorectal cancer, head and neck cancer, kidney cancer, lung cancer or pancreatic cancer may be detected in an animal, such as in a mammal and particularly in a human.

Screening Assays

The invention provides methods for identifying agents (e.g. candidate compounds or test compounds) that bind to Ephrin type-A receptor 10 or have a stimulatory or inhibitory effect on the expression or activity of Ephrin type-A receptor 10. The invention also provides methods of identifying agents, candidate compounds or test compounds that bind to an Ephrin type-A receptor 10-related polypeptide or an Ephrin type-A receptor 10 fusion protein or have a stimulatory or inhibitory effect on the expression or activity of an Ephrin type-A receptor 10-related polypeptide or an Ephrin type-A receptor 10 fusion protein. Examples of agents, candidate compounds or test compounds include, but are not limited to, nucleic acids (e.g. DNA and RNA), carbohydrates, lipids, proteins, peptides, peptidomimetics, small molecules and other drugs. Agents can be obtained using any of the numerous approaches in combinatorial library methods known in the art, including: biological libraries; spatially addressable parallel solid phase or solution phase libraries; synthetic library methods requiring deconvolution; the "one-bead one-compound" library method; and synthetic library methods using affinity chromatography selection. The biological library approach is limited to peptide libraries, while the other four approaches are applicable to peptide, non-peptide oligomer or small molecule libraries of compounds (Lam, 1997, Anticancer Drug Des. 12:145; U.S. Pat. Nos. 5,738,996; and 5,807,683, each of which is incorporated herein in its entirety by reference).

Examples of methods for the synthesis of molecular libraries can be found in the art, for example in: DeWitt et al., 1993, Proc. Natl. Acad. Sci. USA 90:6909; Erb et al., 1994, Proc.

Natl. Acad. Sci. USA 91:11422; Zuckermann et al., 1994, J. Med. Chem. 37:2678; Cho et al., 1993, Science 261:1303; Carrell et al., 1994, Angew. Chem. Int. Ed. Engl. 33:2059; Carell et al., 1994, Angew. Chem. Int. Ed. Engl. 33:2061; and Gallop et al., 1994, J. Med. Chem. 37:1233, each of which is incorporated herein in its entirety by reference.

Libraries of compounds may be presented, e.g. presented in solution (e.g. Houghten, 1992, Bio/Techniques 13:412-421), or on beads (Lam, 1991, Nature 354:82-84), chips (Fodor, 1993, Nature 364:555-556), bacteria (U.S. Pat. No. 5,223,409), spores (U.S. Pat. Nos. 5,571,698; 5,403,484; and 5,223,409), plasmids (Cull et al., 1992, Proc. Natl. Acad. Sci. USA 89:1865-1869) or phage (Scott and Smith, 1990, Science 249:386-390; Devlin, 1990, Science 249:404-406; Cwirla et al., 1990, Proc. Natl. Acad. Sci. USA 87:6378-6382; and Felici, 1991, J. Mol. Biol. 222:301-310), each of which is incorporated herein in its entirety by reference.

In one embodiment, agents that interact with (i.e. bind to) Ephrin type-A receptor 10, an Ephrin type-A receptor 10 fragment (e.g. a functionally active fragment), an Ephrin type-A receptor 10-related polypeptide, a fragment of an Ephrin type-A receptor 10-related polypeptide, or an Ephrin type-A receptor 10 fusion protein are identified in a cell-based assay system. In accordance with this embodiment, cells expressing Ephrin type-A receptor 10, a fragment of an Ephrin type-A receptor 10, an Ephrin type-A receptor 10-related polypeptide, a fragment of the Ephrin type-A receptor 10-related polypeptide, or an Ephrin type-A receptor 10 fusion protein are contacted with a candidate compound or a control compound and the ability of the candidate compound to interact with Ephrin type-A receptor 10 is determined. If desired, this assay may be used to screen a plurality (e.g. a library) of candidate compounds. The cell, for example, can be of prokaryotic origin (e.g. $E.\ coli$) or eukaryotic origin (e.g. yeast or mammalian). Further, the cells can express Ephrin type-A receptor 10, a fragment of Ephrin type-A receptor 10, an Ephrin type-A receptor 10-related polypeptide, a fragment of the Ephrin type-A receptor 10-related polypeptide, or an Ephrin type-A receptor 10 fusion protein endogenously or be genetically engineered to express Ephrin type-A receptor 10, a fragment of Ephrin type-A receptor 10, an Ephrin type-A receptor 10-related polypeptide, a fragment of the Ephrin type-A receptor 10-related polypeptide, or an Ephrin type-A receptor 10 fusion protein. In certain instances, Ephrin type-A receptor 10, a fragment of Ephrin type-A receptor 10, an Ephrin type-A receptor 10-related polypeptide, a fragment of the Ephrin type-A receptor 10-related polypeptide, or an Ephrin type-A receptor 10 fusion protein or the candidate compound is labelled, for example with a radioactive label (such as $^{32}P$, $^{35}S$, and $^{125}I$) or a fluorescent label (such as fluorescein isothiocyanate, rhodamine, phycoerythrin, phycocyanin, allophycocyanin, o-phthaldehyde or fluorescamine) to enable detection of an interaction between Ephrin type-A receptor 10 and a candidate compound. The ability of the candidate compound to interact directly or indirectly with Ephrin type-A receptor 10, a fragment of an Ephrin type-A receptor 10, an Ephrin type-A receptor 10-related polypeptide, a fragment of an Ephrin type-A receptor 10-related polypeptide, or an Ephrin type-A receptor 10 fusion protein can be determined by methods known to those of skill in the art. For example, the interaction between a candidate compound and Ephrin type-A receptor 10, an Ephrin type-A receptor 10-related polypeptide, a fragment of an Ephrin type-A receptor 10-related polypeptide, or an Ephrin type-A receptor 10 fusion protein can be determined by flow cytometry, a scintillation assay, immunoprecipitation or western blot analysis.

In another embodiment, agents that interact with (i.e. bind to) Ephrin type-A receptor 10, an Ephrin type-A receptor 10 fragment (e.g. a functionally active fragment), an Ephrin type-A receptor 10-related polypeptide, a fragment of an Ephrin type-A receptor 10-related polypeptide, or an Ephrin type-A receptor 10 fusion protein are identified in a cell-free assay system. In accordance with this embodiment, a native or recombinant Ephrin type-A receptor 10 or fragment thereof, or a native or recombinant Ephrin type-A receptor 10-related polypeptide or fragment thereof, or an Ephrin type-A receptor 10-fusion protein or fragment thereof, is contacted with a candidate compound or a control compound and the ability of the candidate compound to interact with Ephrin type-A receptor 10 or Ephrin type-A receptor 10-related polypeptide, or Ephrin type-A receptor 10 fusion protein is determined. If desired, this assay may be used to screen a plurality (e.g. a library) of candidate compounds. Preferably, Ephrin type-A receptor 10, an Ephrin type-A receptor 10 fragment, an Ephrin type-A receptor 10-related polypeptide, a fragment of an Ephrin type-A receptor 10-related polypeptide, or an Ephrin type-A receptor 10-fusion protein is first immobilized, by, for example, contacting Ephrin type-A receptor 10, an Ephrin type-A receptor 10 fragment, an Ephrin type-A receptor 10-related polypeptide, a fragment of an Ephrin type-A receptor 10-related polypeptide, or an Ephrin type-A receptor 10 fusion protein with an immobilized antibody (or other affinity reagent) which specifically recognizes and binds it, or by contacting a purified preparation of Ephrin type-A receptor 10, an Ephrin type-A receptor 10 fragment, an Ephrin type-A receptor 10-related polypeptide, fragment of an Ephrin type-A receptor 10-related polypeptide, or an Ephrin type-A receptor 10 fusion protein with a surface designed to bind proteins. Ephrin type-A receptor 10, an Ephrin type-A receptor 10 fragment, an Ephrin type-A receptor 10-related polypeptide, a fragment of an Ephrin type-A receptor 10-related polypeptide, or an Ephrin type-A receptor 10 fusion protein may be partially or completely purified (e.g. partially or completely free of other polypeptides) or part of a cell lysate. Further, Ephrin type-A receptor 10, an Ephrin type-A receptor 10 fragment, an Ephrin type-A receptor 10-related polypeptide, or a fragment of an Ephrin type-A receptor 10-related polypeptide may be a fusion protein comprising Ephrin type-A receptor 10 or a biologically active portion thereof, or Ephrin type-A receptor 10-related polypeptide and a domain such as glutathionine-S-transferase. Alternatively, Ephrin type-A receptor 10, an Ephrin type-A receptor 10 fragment, an Ephrin type-A receptor 10-related polypeptide, a fragment of an Ephrin type-A receptor 10-related polypeptide or an Ephrin type-A receptor 10 fusion protein can be biotinylated using techniques well known to those of skill in the art (e.g. biotinylation kit, Pierce Chemicals; Rockford, Ill.). The ability of the candidate compound to interact with Ephrin type-A receptor 10, an Ephrin type-A receptor 10 fragment, an Ephrin type-A receptor 10-related polypeptide, a fragment of an Ephrin type-A receptor 10-related polypeptide, or an Ephrin type-A receptor 10 fusion protein can be determined by methods known to those of skill in the art.

In another embodiment, a cell-based assay system is used to identify agents that bind to or modulate the activity of a protein, such as an enzyme, or a biologically active portion thereof, which is responsible for the production or degradation of Ephrin type-A receptor 10 or is responsible for the post-translational modification of Ephrin type-A receptor 10. In a primary screen, a plurality (e.g. a library) of compounds are contacted with cells that naturally or recombinantly express: (i) Ephrin type-A receptor 10, an isoform of Ephrin type-A receptor 10, an Ephrin type-A receptor 10 homologue, an Ephrin type-A receptor 10-related polypeptide, an Ephrin type-A receptor 10 fusion protein, or a biologically active fragment of any of the foregoing; and (ii) a protein that is responsible for processing of Ephrin type-A receptor 10, an Ephrin type-A receptor 10 isoform, an Ephrin type-A receptor 10 homologue, an Ephrin type-A receptor 10-related polypeptide, an Ephrin type-A receptor 10 fusion protein, or a fragment in order to identify compounds that modulate the production, degradation, or post-translational modification of Ephrin type-A receptor 10, an Ephrin type-A receptor 10 isoform, an Ephrin type-A receptor 10 homologue, an Ephrin type-A receptor 10-related polypeptide, an Ephrin type-A receptor 10 fusion protein or fragment. If desired, compounds identified in the primary screen can then be assayed in a secondary screen against cells naturally or recombinantly expressing Ephrin type-A receptor 10. The ability of the candidate compound to modulate the production, degradation or post-translational modification of Ephrin type-A receptor 10, isoform, homologue, Ephrin type-A receptor 10-related polypeptide, or Ephrin type-A receptor 10 fusion protein can be determined by methods known to those of skill in the art, including without limitation, flow cytometry, a scintillation assay, immunoprecipitation and western blot analysis.

In another embodiment, agents that competitively interact with (i.e. bind to) Ephrin type-A receptor 10, an Ephrin type-A receptor 10 fragment, an Ephrin type-A receptor 10-related polypeptide, a fragment of an Ephrin type-A receptor 10-related polypeptide, or an Ephrin type-A receptor 10 fusion protein are identified in a competitive binding assay. In accordance with this embodiment, cells expressing Ephrin type-A receptor 10, an Ephrin type-A receptor 10 fragment, an Ephrin type-A receptor 10-related polypeptide, a fragment of an Ephrin type-A receptor 10-related polypeptide, or an Ephrin type-A receptor 10 fusion protein are contacted with a candidate compound and a compound known to interact with Ephrin type-A receptor 10, an Ephrin type-A receptor 10 fragment, an Ephrin type-A receptor 10-related polypeptide, a fragment of an Ephrin type-A receptor 10-related polypeptide or an Ephrin type-A receptor 10 fusion protein; the ability of the candidate compound to preferentially interact with Ephrin type-A receptor 10, an Ephrin type-A receptor 10 fragment, an Ephrin type-A receptor 10-related polypeptide, a fragment of an Ephrin type-A receptor 10-related polypeptide, or an Ephrin type-A receptor 10 fusion protein is then determined. Alternatively, agents that preferentially interact with (i.e. bind to) Ephrin type-A receptor 10, an Ephrin type-A receptor 10 fragment, an Ephrin type-A receptor 10-related polypeptide or fragment of an Ephrin type-A receptor 10-related polypeptide are identified in a cell-free assay system by contacting Ephrin type-A receptor 10, an Ephrin type-A receptor 10 fragment, an Ephrin type-A receptor 10-related polypeptide, a fragment of an Ephrin type-A receptor 10-related polypeptide, or an Ephrin type-A receptor 10 fusion protein with a candidate compound and a compound known to interact with Ephrin type-A receptor 10, an Ephrin type-A receptor 10-related polypeptide or an Ephrin type-A receptor 10 fusion protein. As stated above, the ability of the candidate compound to interact with Ephrin type-A receptor 10, an Ephrin type-A receptor 10 fragment, an Ephrin type-A receptor 10-related polypeptide, a fragment of an Ephrin type-A receptor 10-related polypeptide, or an Ephrin type-A receptor 10 fusion protein can be determined by methods known to those of skill in the art. These assays, whether cell-based or cell-free, can be used to screen a plurality (e.g. a library) of candidate compounds.

In another embodiment, agents that modulate (i.e. upregulate or downregulate) the expression or activity of Ephrin type-A receptor 10 or an Ephrin type-A receptor 10-related polypeptide are identified by contacting cells (e.g. cells of prokaryotic origin or eukaryotic origin) expressing Ephrin type-A receptor 10 or an Ephrin type-A receptor 10-related polypeptide with a candidate compound or a control compound (e.g. phosphate buffered saline (PBS)) and determining the expression of Ephrin type-A receptor 10, Ephrin type-A receptor 10-related polypeptide, or Ephrin type-A receptor 10 fusion protein, mRNA encoding Ephrin type-A receptor 10, or mRNA encoding the Ephrin type-A receptor 10-related polypeptide. The level of expression of Ephrin type-A receptor 10, Ephrin type-A receptor 10-related polypeptide, mRNA encoding Ephrin type-A receptor 10, or mRNA encoding the Ephrin type-A receptor 10-related polypeptide in the presence of the candidate compound is compared to the level of expression of Ephrin type-A receptor 10, Ephrin type-A receptor 10-related polypeptide, mRNA encoding Ephrin type-A receptor 10, or mRNA encoding the Ephrin type-A receptor 10-related polypeptide in the absence of the candidate compound (e.g. in the presence of a control compound). The candidate compound can then be identified as a modulator of the expression of Ephrin type-A receptor 10, or the Ephrin type-A receptor 10-related polypeptide based on this comparison. For example, when expression of Ephrin type-A receptor 10 or mRNA is significantly greater in the presence of the candidate compound than in its absence, the candidate compound is identified as a stimulator of expression of Ephrin type-A receptor 10 or mRNA. Alternatively, when expression of Ephrin type-A receptor 10 or mRNA is significantly less in the presence of the candidate compound than in its absence, the candidate compound is identified as an inhibitor of the expression of Ephrin type-A receptor 10 or mRNA. The level of expression of Ephrin type-A receptor 10 or the mRNA that encodes it can be determined by methods known to those of skill in the art. For example, mRNA expression can be assessed by Northern blot analysis or RT-PCR, and protein levels can be assessed by western blot analysis.

In another embodiment, agents that modulate the activity of Ephrin type-A receptor 10 or an Ephrin type-A receptor 10-related polypeptide are identified by contacting a preparation containing Ephrin type-A receptor 10 or Ephrin type-A receptor 10-related polypeptide or cells (e.g. prokaryotic or eukaryotic cells) expressing Ephrin type-A receptor 10 or Ephrin type-A receptor 10-related polypeptide with a test compound or a control compound and determining the ability of the test compound to modulate (e.g. stimulate or inhibit) the activity of Ephrin type-A receptor 10 or Ephrin type-A receptor 10-related polypeptide. The activity of Ephrin type-A receptor 10 or an Ephrin type-A receptor 10-related polypeptide can be assessed by detecting induction of a cellular signal transduction pathway of Ephrin type-A receptor 10 or Ephrin type-A receptor 10-related polypeptide (e.g. intracellular $Ca^{2+}$, diacylglycerol, IP3, etc.), detecting catalytic or enzymatic activity of the target on a suitable substrate, detecting the induction of a reporter gene (e.g. a regulatory element that is responsive to Ephrin type-A receptor 10 or an Ephrin type-A receptor 10-related polypeptide and is operably linked to a nucleic acid encoding a detectable marker, e.g. luciferase), or detecting a cellular response, for example, cellular differentiation, or cell proliferation. Based on the present description, techniques known to those of skill in the art can be used for measuring these activities (see, e.g. U.S. Pat. No. 5,401,639, which is incorporated herein by reference). The candidate compound can then be identified as a modulator of the activity of Ephrin type-A receptor 10 or an Ephrin type-A receptor 10-related polypeptide by comparing the effects of the candidate compound to the control compound. Suitable control compounds include phosphate buffered saline (PBS) and normal saline (NS).

In another embodiment, agents that modulate (i.e. upregulate or downregulate) the expression, activity or both the expression and activity of Ephrin type-A receptor 10 or an Ephrin type-A receptor 10-related polypeptide are identified in an animal model. Examples of suitable animals include, but are not limited to, mice, rats, rabbits, monkeys, guinea pigs, dogs and cats. Preferably, the animal used represent a model of bladder cancer, breast cancer, colorectal cancer, head and neck cancer, kidney cancer, lung cancer or pancreatic cancer (e.g. xenografts of bladder cancer cell lines such as UCRU-BL-12, UCRU-BL-13 and UCRU-BL-14, Russell et al. Cancer Res. 1986 April; 46(4 Pt 2):2035-40; xenografts of breast cancer cell lines such as MCF-7 (Ozzello L, Sordat M., Eur J. Cancer. 1980; 16:553-559) and MCF10AT (Miller et al., J Natl Cancer Inst. 1993; 85:1725-1732) in nude or SCID mice; xenografts of human colorectal cancer cell lines such as MDA-MB-345 in oestrogen-deprived SCID mice, Eccles et al. 1994 Cell Biophysics 24/25, 279; xenografts of head and neck cancer cell lines such as FaDu and HNX-OE; xenografts of renal cell cancer cell lines such as LABAZ1 in immune compromised mice, Zisman et al, Cancer Research 63, 4952-4959, Aug. 15, 2003; xenografts of non small cell lung cancer cell lines such as A549 and H460 and xenografts of small cell lung cancer cell lines such as NCI-H345 or xenografts of pancreatic cancer cell lines such as MIA PaCa-2 in nude mice, Marincola et al., J Surg Res 1989 December; 47(6):520-9). These can be utilized to test compounds that modulate Ephrin type-A receptor 10 levels, since the pathology exhibited in these models is similar to that of bladder cancer, breast cancer, colorectal cancer, head and neck cancer, kidney cancer, lung cancer or pancreatic cancer. In accordance with this embodiment, the test compound or a control compound is administered (e.g. orally, rectally or parenterally such as intraperitoneally or intravenously) to a suitable animal and the effect on the expression, activity or both expression and activity of Ephrin type-A receptor 10 or Ephrin type-A receptor 10-related polypeptide is determined. Changes in the expression of Ephrin type-A receptor 10 or an Ephrin type-A receptor 10-related polypeptide can be assessed by the methods outlined above.

In yet another embodiment, Ephrin type-A receptor 10 or an Ephrin type-A receptor 10-related polypeptide is used as a "bait protein" in a two-hybrid assay or three hybrid assay to identify other proteins that bind to or interact with Ephrin type-A receptor 10 or an Ephrin type-A receptor 10-related polypeptide (see, e.g. U.S. Pat. No. 5,283,317; Zervos et al. (1993) Cell 72:223-232; Madura et al. (1993) J. Biol. Chem. 268:12046-12054; Bartel et al. (1993) Bio/Techniques 14:920-924; Iwabuchi et al. (1993) Oncogene 8:1693-1696; and PCT Publication No. WO 94/10300). As those skilled in the art will appreciate, such binding proteins are also likely to be involved in the propagation of signals by Ephrin type-A receptor 10 as, for example, upstream or downstream elements of a signalling pathway involving Ephrin type-A receptor 10.

This invention further provides novel agents identified by the above-described screening assays and uses thereof for treatments as described herein. In addition, the invention also provides the use of an agent which interacts with, or modulates the activity of, Ephrin type-A receptor 10 in the manufacture of a medicament for the treatment of bladder cancer, breast cancer, colorectal cancer, head and neck cancer, kidney cancer, lung cancer or pancreatic cancer.

Therapeutic Use of Ephrin Type-A Receptor 10

The invention provides for treatment or prevention of various diseases and disorders by administration of a therapeutic compound. Such compounds include but are not limited to: Ephrin type-A receptor 10, Ephrin type-A receptor 10 analogues, Ephrin type-A receptor 10-related polypeptides and derivatives (including fragments) thereof; antibodies (or other affinity reagents) to the foregoing; nucleic acids encoding Ephrin type-A receptor 10, Ephrin type-A receptor 10 analogues, Ephrin type-A receptor 10-related polypeptides and fragments thereof; antisense nucleic acids to a gene encoding Ephrin type-A receptor 10 or an Ephrin type-A receptor 10-related polypeptide; and modulator (e.g. agonists and antagonists) of a gene encoding Ephrin type-A receptor 10 or an Ephrin type-A receptor 10-related polypeptide. An important feature of the present invention is the identification of genes encoding Ephrin type-A receptor 10 involved in bladder cancer, breast cancer, colorectal cancer, head and neck cancer, kidney cancer, lung cancer or pancreatic cancer. Bladder cancer, breast cancer, colorectal cancer, head and neck cancer, kidney cancer, lung cancer or pancreatic cancer can be treated (e.g. to ameliorate symptoms or to retard onset or progression) or prevented by administration of a therapeutic compound that reduces function or expression of Ephrin type-A receptor 10 in the serum or tissue of subjects having bladder cancer, breast cancer, colorectal cancer, head and neck cancer, kidney cancer, lung cancer or pancreatic cancer.

In one embodiment, one or more antibodies (or other affinity reagents) each specifically binding to Ephrin type-A receptor 10 are administered alone or in combination with one or more additional therapeutic compounds or treatments.

A biological product such as an antibody (or other affinity reagent) is, for example, allogeneic to the subject to which it is administered. In one embodiment, a human Ephrin type-A receptor 10 or a human Ephrin type-A receptor 10-related polypeptide, a nucleotide sequence encoding a human Ephrin type-A receptor 10 or a human Ephrin type-A receptor 10-related polypeptide, or an antibody (or other affinity reagent) to a human Ephrin type-A receptor 10 or a human Ephrin type-A receptor 10-related polypeptide, is administered to a human subject for therapy (e.g. to ameliorate symptoms or to retard onset or progression) or prophylaxis.

Without being limited by theory, it is conceived that the therapeutic activity of antibodies (or other affinity reagents) which specifically bind to Ephrin type-A receptor 10 may be achieved through the phenomenon of Antibody—Dependent Cell-mediated Cytotoxicity (ADCC) (see e.g. Janeway Jr. C. A. et al., Immunobiology, 5th ed., 2001, Garland Publishing, ISBN 0-8153-3642-X; Pier G. B. et al., Immunology, Infection, and Immunity, 2004, p 246-5; Albanell J. et al., Advances in Experimental Medicine and Biology, 2003, 532: p 2153-68 and Weng, W.-K. et al., Journal of Clinical Oncology, 2003, 21: p 3940-3947).

Treatment and Prevention of Bladder Cancer, Breast Cancer, Colorectal Cancer, Head and Neck Cancer, Kidney Cancer, Lung Cancer or Pancreatic Cancer Bladder cancer, breast cancer, colorectal cancer, head and neck cancer, kidney cancer, lung cancer or pancreatic cancer is treated or prevented by administration to a subject suspected of having or known to have bladder cancer, breast cancer, colorectal cancer, head and neck cancer, kidney cancer, lung cancer or pancreatic cancer or to be at risk of developing bladder cancer, breast cancer, colorectal cancer, head and neck cancer, kidney cancer, lung cancer or pancreatic cancer of a compound that modulates (i.e. increases or decreases) the level or activity (i.e. function) of Ephrin type-A receptor 10 that is differentially present in the serum or tissue of subjects having bladder cancer, breast cancer, colorectal cancer, head and neck cancer, kidney cancer, lung cancer or pancreatic cancer compared with serum or tissue of subjects free from bladder cancer, breast cancer, colorectal cancer, head and neck cancer, kidney cancer, lung cancer and pancreatic cancer. In one embodiment, bladder cancer, breast cancer, colorectal cancer, head and neck cancer, kidney cancer, lung cancer or pancreatic cancer is treated or prevented by administering to a subject suspected of having or known to have bladder cancer, breast cancer, colorectal cancer, head and neck cancer, kidney cancer, lung cancer or pancreatic cancer or to be at risk of developing bladder cancer, breast cancer, colorectal cancer, head and neck cancer, kidney cancer, lung cancer or pancreatic cancer a compound that upregulates (i.e. increases) the level or activity (i.e. function) of Ephrin type-A receptor 10 that are decreased in the serum or tissue of subjects having bladder cancer, breast cancer, colorectal cancer, head and neck cancer, kidney cancer, lung cancer or pancreatic cancer. Examples of such a compound include, but are not limited to, Ephrin type-A receptor 10 antisense oligonucleotides, ribozymes, antibodies (or other affinity reagents) directed against Ephrin type-A receptor 10, and compounds that inhibit the enzymatic activity of Ephrin type-A receptor 10. Other useful compounds e.g. Ephrin type-A receptor 10 antagonists and small molecule Ephrin type-A receptor 10 antagonists, can be identified using in vitro assays.

Bladder cancer, breast cancer, colorectal cancer, head and neck cancer, kidney cancer, lung cancer or pancreatic cancer is also treated or prevented by administration to a subject suspected of having or known to have bladder cancer, breast cancer, colorectal cancer, head and neck cancer, kidney cancer, lung cancer or pancreatic cancer or to be at risk of developing bladder cancer, breast cancer, colorectal cancer, head and neck cancer, kidney cancer, lung cancer or pancreatic cancer of a compound that downregulates the level or activity (i.e. function) of Ephrin type-A receptor 10 that are increased in the serum or tissue of subjects having bladder cancer, breast cancer, colorectal cancer, head and neck cancer, kidney cancer, lung cancer or pancreatic cancer. Examples of such a compound include but are not limited to: Ephrin type-A receptor 10, Ephrin type-A receptor 10 fragments and Ephrin type-A receptor 10-related polypeptides; nucleic acids encoding Ephrin type-A receptor 10, an Ephrin type-A receptor 10 fragment and an Ephrin type-A receptor 10-related polypeptide (e.g. for use in gene therapy); and, for those Ephrin type-A receptor 10 or Ephrin type-A receptor 10-related polypeptides with enzymatic activity, compounds or molecules known to modulate that enzymatic activity. Other compounds that can be used, e.g. Ephrin type-A receptor 10 agonists, can be identified using in in vitro assays.

In another embodiment, therapy or prophylaxis is tailored to the needs of an individual subject. Thus, in specific embodiments, compounds that promote the level or function of Ephrin type-A receptor 10 are therapeutically or prophylactically administered to a subject suspected of having or known to have bladder cancer, breast cancer, colorectal cancer, head and neck cancer, kidney cancer, lung cancer or pancreatic cancer, in whom the level or function of Ephrin type-A receptor 10 are absent or are decreased relative to a control or normal reference range. In further embodiments, compounds that promote the level or function of Ephrin type-A receptor 10 are therapeutically or prophylactically administered to a subject suspected of having or known to have bladder cancer, breast cancer, colorectal cancer, head and neck cancer, kidney cancer, lung cancer or pancreatic cancer in whom the level or function of Ephrin type-A receptor 10 are increased relative to a control or to a reference range. In further embodiments, compounds that decrease the level or function of Ephrin type-A receptor 10 are therapeutically or prophylactically administered to a subject suspected of having or known to have bladder cancer, breast cancer, colorectal cancer, head and neck cancer, kidney cancer, lung cancer or pancreatic cancer in whom the level or function of Ephrin type-A receptor 10 are increased relative to a control or to a reference range. In further embodiments, compounds that decrease the level or function of Ephrin type-A receptor 10 are therapeutically or prophylactically administered to a subject suspected of having or known to have bladder cancer, breast cancer, colorectal cancer, head and neck cancer, kidney cancer, lung cancer or pancreatic cancer in whom the level or function of Ephrin type-A receptor 10 are decreased relative to a control or to a reference range. The change in Ephrin type-A receptor 10 function or level due to the administration of such compounds can be readily detected, e.g. by obtaining a sample (e.g. blood or urine) and assaying in vitro the level or activity of Ephrin type-A receptor 10, or the level of mRNA encoding Ephrin type-A receptor 10, or any combination of the foregoing. Such assays can be performed before and after the administration of the compound as described herein.

The compounds of the invention include but are not limited to any compound, e.g. a small organic molecule, protein, peptide, antibody (or other affinity reagent), nucleic acid, etc. that restores the Ephrin type-A receptor 10 profile towards normal. The compounds of the invention may be given in combination with any other chemotherapy drugs.

Vaccine Therapy

Another aspect of the invention is an immunogenic composition, suitably a vaccine composition, comprising Ephrin type-A receptor 10 or an epitope containing fragment thereof, or nucleic acid encoding Ephrin type-A receptor 10 or a fragment thereof optionally together with an immunostimulant.

There is also provided a method of raising an immune response which comprises administering to a subject such compositions and a method for treating or preventing bladder cancer, breast cancer, colorectal cancer, head and neck cancer, kidney cancer, lung cancer or pancreatic cancer which comprises administering to a subject in need thereof a therapeutically effective amount of such compositions and such compositions for use in preventing or treating bladder cancer, breast cancer, colorectal cancer, head and neck cancer, kidney cancer, lung cancer or pancreatic cancer.

Thus, Ephrin type-A receptor 10 may be useful as antigenic material, and may be used in the production of vaccines for treatment or prophylaxis of bladder cancer, breast cancer, colorectal cancer, head and neck cancer, kidney cancer, lung cancer or pancreatic cancer. Such material can be "antigenic" and/or "immunogenic". Generally, "antigenic" is taken to mean that the protein is capable of being used to raise antibodies (or other affinity reagents) or indeed is capable of inducing an antibody response in a subject or experimental animal. "Immunogenic" is taken to mean that the protein is capable of eliciting a protective immune response in a subject or experimental animal. Thus, in the latter case, the protein may be capable of not only generating an antibody response but, in addition, non-antibody based immune responses. "Immunogenic" also embraces whether the protein may elicit an immune-like response in an in vitro setting e.g. a T-cell proliferation assay. The generation of an appropriate immune response may require the presence of one or more adjuvants and/or appropriate presentation of an antigen.

The skilled person will appreciate that homologues or derivatives of Ephrin type-A receptor 10 will also find use as antigenic/immunogenic material. Thus, for instance proteins which include one or more additions, deletions, substitutions or the like are encompassed by the present invention. In addition, it may be possible to replace one amino acid with another of similar "type". For instance, replacing one hydrophobic amino acid with another. One can use a program such as the CLUSTAL program to compare amino acid sequences. This program compares amino acid sequences and finds the optimal alignment by inserting spaces in either sequence as appropriate. It is possible to calculate amino acid identity or similarity (identity plus conservation of amino acid type) for an optimal alignment. A program like BLASTx will align the longest stretch of similar sequences and assign a value to the fit. It is thus possible to obtain a comparison where several regions of similarity are found, each having a different score. Both types of analysis are contemplated in the present invention.

In the case of homologues and derivatives, the degree of identity with a protein as described herein is less important than that the homologue or derivative should retain its antigenicity and/or immunogenicity. However, suitably, homologues or derivatives having at least 60% similarity (as discussed above) with the proteins or polypeptides described herein are provided, for example, homologues or derivatives having at least 70% similarity, such as at least 80% similarity. Particularly, homologues or derivatives having at least 90% or even 95% similarity are provided. Suitably, homologues or derivatives have at least 60% sequence identity with the proteins or polypeptides described herein, for example, homologues or derivatives have at least 70% identity, such as at least 80% identity. Particularly, homologues or derivatives have at least 90% or even 95% identity.

In an alternative approach, the homologues or derivatives could be fusion proteins, incorporating moieties which render purification easier, for example by effectively tagging the desired protein or polypeptide. It may be necessary to remove the "tag" or it may be the case that the fusion protein itself retains sufficient antigenicity to be useful.

It is well known that it is possible to screen an antigenic protein or polypeptide to identify epitopic regions, i.e. those regions which are responsible for the protein or polypeptide's antigenicity or immunogenicity. Methods well known to the skilled person can be used to test fragments and/or homologues and/or derivatives for antigenicity. Thus, the fragments of the present invention should include one or more such epitopic regions or be sufficiently similar to such regions to retain their antigenic/immunogenic properties. Thus, for fragments according to the present invention the degree of identity is perhaps irrelevant, since they may be 100% identical to a particular part of a protein or polypeptide, homologue or derivative as described herein. The key issue, once again, is that the fragment retains the antigenic/immunogenic properties of the protein from which it is derived.

What is important for homologues, derivatives and fragments is that they possess at least a degree of the antigenicity/immunogenicity of the protein or polypeptide from which they are derived. Thus, in an additional aspect of the invention, there is provided antigenic/or immunogenic fragments of Ephrin type-A receptor 10, or of homologues or derivatives thereof.

Ephrin type-A receptor 10, or antigenic fragments thereof, can be provided alone, as a purified or isolated preparation. They may be provided as part of a mixture with one or more other proteins of the invention, or antigenic fragments thereof. In a further aspect, therefore, the invention provides an antigen composition comprising Ephrin type-A receptor 10 and/or one or more antigenic fragments thereof. Such a composition can be used for the detection and/or diagnosis of bladder cancer, breast cancer, colorectal cancer, head and neck cancer, kidney cancer, lung cancer or pancreatic cancer.

Vaccine compositions according to the invention may be either a prophylactic or therapeutic vaccine composition.

The vaccine compositions of the invention can include one or more adjuvants (immunostimulants). Examples well-known in the art include inorganic gels, such as aluminium hydroxide, and water-in-oil emulsions, such as incomplete Freund's adjuvant. Other useful adjuvants will be well known to the skilled person.

Suitable adjuvants for use in vaccine compositions for the treatment of cancer include: 3De-O-acylated monophosphoryl lipid A (known as 3D-MPL or simply MPL see WO92/116556), a saponin, for example QS21 or QS7, and TLR4 agonists such as a CpG containing molecule, for example as disclosed in WO95/26204.

The adjuvants employed may be a combination of components, for example MPL and QS21 or MPL, QS21 and a CpG containing moiety.

Adjuvants may be formulated as oil-in-water emulsions or liposomal formulations.

Such preparations may include other vehicles.

In another embodiment, a preparation of oligonucleotides comprising 10 or more consecutive nucleotides complementary to a nucleotide sequence encoding Ephrin type-A receptor 10 or an Ephrin type-A receptor 10 peptide fragment is used as a vaccine for the treatment of bladder cancer, breast cancer, colorectal cancer, head and neck cancer, kidney cancer, lung cancer or pancreatic cancer. Such preparations may include adjuvants or other vehicles.

Inhibition of Ephrin Type-A Receptor 10 to Treat Bladder Cancer, Breast Cancer, Colorectal Cancer, Head and Neck Cancer, Kidney Cancer, Lung Cancer or Pancreatic Cancer In one embodiment of the invention, bladder cancer, breast cancer, colorectal cancer, head and neck cancer, kidney cancer, lung cancer or pancreatic cancer is treated or prevented by administration of a compound that antagonizes (inhibits) the level and/or function of Ephrin type-A receptor 10 which are elevated in the serum or tissue of subjects having bladder cancer, breast cancer, colorectal cancer, head and neck cancer, kidney cancer, lung cancer or pancreatic cancer as compared with serum or tissue of subjects free from bladder cancer, breast cancer, colorectal cancer, head and neck cancer, kidney cancer, lung cancer and pancreatic cancer.

Compounds useful for this purpose include but are not limited to anti-Ephrin type-A receptor 10 antibodies (or other affinity reagents, and fragments and derivatives containing the binding region thereof), Ephrin type-A receptor 10 antisense or ribozyme nucleic acids, and nucleic acids encoding dysfunctional Ephrin type-A receptor 10 that are used to "knockout" endogenous Ephrin type-A receptor 10 function by homologous recombination (see, e.g. Capecchi, 1989, *Science* 244:1288-1292). Other compounds that inhibit Ephrin type-A receptor 10 function can be identified by use of known in vitro assays, e.g. assays for the ability of a test compound to inhibit binding of Ephrin type-A receptor 10 to another protein or a binding partner, or to inhibit a known Ephrin type-A receptor 10 function.

Such inhibition may, for example, be assayed in vitro or in cell culture, but genetic assays may also be employed. The Preferred Technologies described herein can also be used to detect levels of Ephrin type-A receptor 10 before and after the administration of the compound. Suitable in vitro or in vivo assays are utilized to determine the effect of a specific compound and whether its administration is indicated for treatment of the affected tissue, as described in more detail below.

In a specific embodiment, a compound that inhibits Ephrin type-A receptor 10 function (activity) is administered therapeutically or prophylactically to a subject in whom an increased serum or tissue level or functional activity of Ephrin type-A receptor 10 (e.g. greater than the normal level or desired level) is detected as compared with serum or tissue of subjects with bladder cancer, breast cancer, colorectal cancer, head and neck cancer, kidney cancer, lung cancer or pancreatic cancer who do not receive treatment according to the invention or to bring the level or activity to that found in subjects free from bladder cancer, breast cancer, colorectal cancer, head and neck cancer, kidney cancer, lung cancer and pancreatic cancer or a predetermined reference range. Methods standard in the art can be employed to measure the increase in Ephrin type-A receptor 10 level or function, as outlined above. Suitable Ephrin type-A receptor 10 inhibitor compositions may, for example, include small molecules, i.e. molecules of 1000 Daltons or less. Such small molecules can be identified by the screening methods described herein.

Assays for Therapeutic or Prophylactic Compounds

The present invention also provides assays for use in drug discovery in order to identify or verify the efficacy of compounds for treatment or prevention of bladder cancer, breast cancer, colorectal cancer, head and neck cancer, kidney cancer, lung cancer or pancreatic cancer.

Thus there is provided a method of screening for compounds that modulate the activity of Ephrin type-A receptor 10, the method comprising: (a) contacting Ephrin type-A receptor 10 or a biologically active portion thereof with a candidate compound; and (b) determining whether activity of Ephrin type-A receptor 10 is thereby modulated. Such a process may comprise (a) contacting Ephrin type-A receptor 10 or a biologically active portion thereof with a candidate compound in a sample; and (b) comparing the activity of Ephrin type-A receptor 10 or a biologically active portion thereof in said sample after contact with said candidate compound with the activity of Ephrin type-A receptor 10 or a biologically active portion thereof in said sample before contact with said candidate compound, or with a reference level of activity.

The method of screening may be a method of screening for compounds that inhibit activity of Ephrin type-A receptor 10.

Ephrin type-A receptor 10 or a biologically active portion thereof may, for example be expressed on or by a cell. Ephrin type-A receptor 10 or a biologically active portion thereof may, for example, be isolated from cells which express it. Ephrin type-A receptor 10 or a biologically active portion thereof may, for example, be immobilised onto a solid phase.

There is also provided a method of screening for compounds that modulate the expression of Ephrin type-A receptor 10 or nucleic acid encoding Ephrin type-A receptor 10, the method comprising: (a) contacting cells expressing Ephrin type-A receptor 10 or nucleic acid encoding Ephrin type-A receptor 10 with a candidate compound; and (b) determining whether expression of Ephrin type-A receptor 10 or nucleic acid encoding Ephrin type-A receptor 10 is thereby modulated. Such a process may comprises (a) contacting cells expressing Ephrin type-A receptor 10 or nucleic acid encoding Ephrin type-A receptor 10 with a candidate compound in a sample; and (b) comparing the expression of Ephrin type-A receptor 10 or nucleic acid encoding Ephrin type-A receptor 10 by cells in said sample after contact with said candidate compound with the expression of Ephrin type-A receptor 10 or nucleic acid encoding Ephrin type-A receptor 10 of cells in said sample before contact with said candidate compound, or with a reference level of expression.

The method may be a method of screening for compounds that inhibit expression of Ephrin type-A receptor 10 or nucleic acid encoding Ephrin type-A receptor 10.

Other aspects of the invention include: a compound obtainable by an aforementioned screening method, a compound which modulates the activity or expression of Ephrin type-A receptor 10 or nucleic acid encoding Ephrin type-A receptor 10, for example a compound which inhibits the activity or expression of Ephrin type-A receptor 10 or nucleic acid encoding Ephrin type-A receptor 10.

Such a compound is provided for use in treating or preventing bladder cancer, breast cancer, colorectal cancer, head and neck cancer, kidney cancer, lung cancer or pancreatic cancer. There is also provided a method for treating or preventing bladder cancer, breast cancer, colorectal cancer, head and neck cancer, kidney cancer, lung cancer or pancreatic cancer which comprises administering to a subject in need thereof a therapeutically effective amount of such a compound.

Test compounds can be assayed for their ability to restore Ephrin type-A receptor 10 levels in a subject having bladder cancer, breast cancer, colorectal cancer, head and neck cancer, kidney cancer, lung cancer or pancreatic cancer towards levels found in subjects free from bladder cancer, breast cancer, colorectal cancer, head and neck cancer, kidney cancer, lung cancer and pancreatic cancer or to produce similar changes in experimental animal models of bladder cancer, breast cancer, colorectal cancer, head and neck cancer, kidney cancer, lung cancer or pancreatic cancer. Compounds able to restore Ephrin type-A receptor 10 levels in a subject having bladder cancer, breast cancer, colorectal cancer, head and neck cancer, kidney cancer, lung cancer or pancreatic cancer towards levels found in subjects free from bladder cancer, breast cancer, colorectal cancer, head and neck cancer, kidney cancer, lung cancer and pancreatic cancer or to produce similar changes in experimental animal models of bladder cancer, breast cancer, colorectal cancer, head and neck cancer, kidney cancer, lung cancer or pancreatic cancer can be used as lead compounds for further drug discovery, or used therapeutically. Ephrin type-A receptor 10 expression can be assayed by the Preferred Technologies described herein, immunoassays, gel electrophoresis followed by visualization, detection of Ephrin type-A receptor 10 activity, or any other method taught herein or known to those skilled in the art. Such assays can be used to screen candidate drugs, in clinical monitoring or in drug development, where abundance of Ephrin type-A receptor 10 can serve as a surrogate marker for clinical disease.

In various specific embodiments, in vitro assays can be carried out with cells representative of cell types involved in a subject's disorder, to determine if a compound has a desired effect upon such cell types.

Compounds for use in therapy can be tested in suitable animal model systems prior to testing in humans, including but not limited to rats, mice, chicken, cows, monkeys, rabbits, etc. For in vivo testing, prior to administration to humans, any animal model system known in the art may be used. Examples of animal models of bladder cancer, breast cancer, colorectal cancer, head and neck cancer, kidney cancer, lung cancer or pancreatic cancer include, but are not limited to xenografts of bladder cancer cell lines such as UCRU-BL-12, UCRU-BL-13 and UCRU-BL-14, Russell et al. Cancer Res. 1986 April; 46(4 Pt 2):2035-40; xenografts of breast cancer cell lines such as MCF-7 (Ozzello L, Sordat M., Eur J. Cancer. 1980; 16:553-559) and MCF10AT (Miller et al., J Natl Cancer Inst. 1993; 85:1725-1732) in nude or SCID mice; xenografts of human colorectal cancer cell lines such as MDA-MB-345 in oestrogen-deprived SCID mice, Eccles et al. 1994 Cell Biophysics 24/25, 279; xenografts of head and neck cancer cell lines such as FaDu and HNX-OE; xenografts of renal cell cancer cell lines such as LABAZ1 in immune compromised mice, Zisman et al, Cancer Research 63, 4952-4959, Aug. 15, 2003; xenografts of non small cell lung cancer cell lines such as A549 and H460 and xenografts of small cell lung cancer cell lines such as NCI-H345 or xenografts of pancreatic cancer cell lines such as MIA PaCa-2 in nude mice, Marincola et al., J Surg Res 1989 December; 47(6):520-9. These can be utilized to test compounds that modulate Ephrin type-A receptor 10 levels, since the pathology exhibited in these models is similar to that of bladder cancer, breast cancer, colorectal cancer, head and neck cancer, kidney cancer, lung cancer or pancreatic cancer. It is also apparent to the skilled artisan that based upon the present disclosure, transgenic animals can be produced with "knock-out" mutations of the gene or genes encoding Ephrin type-A receptor 10. A "knock-out" mutation of a gene is a mutation that causes the mutated gene to not be expressed, or expressed in an aberrant form or at a low level, such that the activity associated with the gene product is nearly or entirely absent. The transgenic animal is, for example, a mammal, such as a mouse.

In one embodiment, test compounds that modulate the expression of Ephrin type-A receptor 10 are identified in non-human animals (e.g. mice, rats, monkeys, rabbits, and guinea pigs), preferably non-human animal models for bladder cancer, breast cancer, colorectal cancer, head and neck cancer, kidney cancer, lung cancer or pancreatic cancer, expressing Ephrin type-A receptor 10. In accordance with this embodiment, a test compound or a control compound is administered to the animals, and the effect of the test compound on expression of Ephrin type-A receptor 10 is determined. A test compound that alters the expression of Ephrin type-A receptor 10 can be identified by comparing the level of Ephrin type-A receptor 10 (or mRNA encoding the same) in an animal or group of animals treated with a test compound with the level of Ephrin type-A receptor 10 or mRNA in an animal or group of animals treated with a control compound. Techniques known to those of skill in the art can be used to determine the mRNA and protein levels, for example, in situ hybridization. The animals may or may not be sacrificed to assay the effects of a test compound.

In another embodiment, test compounds that modulate the activity of Ephrin type-A receptor 10 or a biologically active portion thereof are identified in non-human animals (e.g. mice, rats, monkeys, rabbits, and guinea pigs), preferably non-human animal models for bladder cancer, breast cancer, colorectal cancer, head and neck cancer, kidney cancer, lung cancer or pancreatic cancer, expressing Ephrin type-A receptor 10. In accordance with this embodiment, a test compound or a control compound is administered to the animals, and the effect of a test compound on the activity of Ephrin type-A receptor 10 is determined. A test compound that alters the activity of Ephrin type-A receptor 10 can be identified by assaying animals treated with a control compound and animals treated with the test compound. The activity of Ephrin type-A receptor 10 can be assessed by detecting induction of a cellular second messenger of Ephrin type-A receptor 10 (e.g. intracellular $Ca^{2+}$, diacylglycerol, IP3, etc.), detecting catalytic or enzymatic activity of Ephrin type-A receptor 10 or binding partner thereof, detecting the induction of a reporter gene (e.g. a regulatory element that is responsive to Ephrin type-A receptor 10 operably linked to a nucleic acid encoding a detectable marker, such as luciferase or green fluorescent protein), or detecting a cellular response (e.g. cellular differentiation or cell proliferation). Techniques known to those of skill in the art can be utilized to detect changes in the activity of Ephrin type-A receptor 10 (see, e.g. U.S. Pat. No. 5,401,639, which is incorporated herein by reference).

In yet another embodiment, test compounds that modulate the level or expression of Ephrin type-A receptor 10 are identified in human subjects having bladder cancer, breast cancer, colorectal cancer, head and neck cancer, kidney cancer, lung cancer or pancreatic cancer, particularly those having severe bladder cancer, breast cancer, colorectal cancer, head and neck cancer, kidney cancer, lung cancer or pancreatic cancer. In accordance with this embodiment, a test compound or a control compound is administered to the human subject, and the effect of a test compound on Ephrin type-A receptor 10 expression is determined by analyzing the expression of Ephrin type-A receptor 10 or the mRNA encoding the same in a biological sample (e.g. serum, plasma, or urine). A test compound that alters the expression of Ephrin type-A receptor 10 can be identified by comparing the level of Ephrin type-A receptor 10 or mRNA encoding the same in a subject or group of subjects treated with a control compound to that in a subject or group of subjects treated with a test compound. Alternatively, alterations in the expression of Ephrin type-A receptor 10 can be identified by comparing the level of Ephrin type-A receptor 10 or mRNA encoding the same in a subject or group of subjects before and after the administration of a test compound. Techniques known to those of skill in the art can be used to obtain the biological sample and analyze the mRNA or protein expression. For example, the Preferred Technologies described herein can be used to assess changes in the level of Ephrin type-A receptor 10.

In another embodiment, test compounds that modulate the activity of Ephrin type-A receptor 10 are identified in human subjects having bladder cancer, breast cancer, colorectal cancer, head and neck cancer, kidney cancer, lung cancer or pancreatic cancer (particularly those with severe bladder cancer, breast cancer, colorectal cancer, head and neck cancer, kidney cancer, lung cancer or pancreatic cancer). In this embodiment, a test compound or a control compound is administered to the human subject, and the effect of a test compound on the activity of Ephrin type-A receptor 10 is determined. A test compound that alters the activity of Ephrin type-A receptor 10 can be identified by comparing biological samples from subjects treated with a control compound to samples from subjects treated with the test compound. Alternatively, alterations in the activity of Ephrin type-A receptor 10 can be identified by comparing the activity of Ephrin type-A receptor 10 in a subject or group of subjects before and after the administration of a test compound. The activity of Ephrin type-A receptor 10 can be assessed by detecting in a biological sample (e.g. serum, plasma, or urine) induction of a cellular signal transduction pathway of Ephrin type-A receptor 10 (e.g. intracellular $Ca^{2+}$, diacylglycerol, IP3, etc.), catalytic or enzymatic activity of Ephrin type-A receptor 10 or a binding partner thereof, or a cellular response, for example, cellular differentiation, or cell proliferation. Techniques known to those of skill in the art can be used to detect changes in the induction of a second messenger of Ephrin type-A receptor 10 or changes in a cellular response. For example, RT-PCR can be used to detect changes in the induction of a cellular second messenger.

In another embodiment, a test compound that changes the level or expression of Ephrin type-A receptor 10 towards levels detected in control subjects (e.g. humans free from bladder cancer, breast cancer, colorectal cancer, head and neck cancer, kidney cancer, lung cancer and pancreatic cancer) is selected for further testing or therapeutic use. In another embodiment, a test compound that changes the activity of Ephrin type-A receptor 10 towards the activity found in control subjects (e.g. humans free from bladder cancer, breast cancer, colorectal cancer, head and neck cancer, kidney cancer, lung cancer and pancreatic cancer) is selected for further testing or therapeutic use.

In another embodiment, test compounds that reduce the severity of one or more symptoms associated with bladder cancer, breast cancer, colorectal cancer, head and neck cancer, kidney cancer, lung cancer or pancreatic cancer are identified in human subjects having bladder cancer, breast cancer, colorectal cancer, head and neck cancer, kidney cancer, lung cancer or pancreatic cancer, particularly subjects with severe bladder cancer, breast cancer, colorectal cancer, head and neck cancer, kidney cancer, lung cancer or pancreatic cancer. In accordance with this embodiment, a test compound or a control compound is administered to the subjects, and the effect of a test compound on one or more symptoms of bladder cancer, breast cancer, colorectal cancer, head and neck cancer, kidney cancer, lung cancer or pancreatic cancer is determined. A test compound that reduces one or more symptoms can be identified by comparing the subjects treated with a control compound to the subjects treated with the test compound. Techniques known to physicians familiar with bladder cancer, breast cancer, colorectal cancer, head and neck cancer, kidney cancer, lung cancer or pancreatic cancer can be used to determine whether a test compound reduces one or more symptoms associated with bladder cancer, breast cancer, colorectal cancer, head and neck cancer, kidney cancer, lung cancer or pancreatic cancer. For example, a test compound that reduces tumour burden in a subject having bladder cancer, breast cancer, colorectal cancer, head and neck cancer, kidney cancer, lung cancer or pancreatic cancer will be beneficial for subjects having bladder cancer, breast cancer, colorectal cancer, head and neck cancer, kidney cancer, lung cancer or pancreatic cancer.

In a particular embodiment, a test compound that reduces the severity of one or more symptoms associated with bladder cancer, breast cancer, colorectal cancer, head and neck cancer, kidney cancer, lung cancer or pancreatic cancer in a human having bladder cancer, breast cancer, colorectal cancer, head and neck cancer, kidney cancer, lung cancer or pancreatic cancer is selected for further testing or therapeutic use.

Therapeutic and Prophylactic Compositions and their Use

The invention provides methods of treatment (and prophylaxis) comprising administering to a subject an effective amount of a compound of the invention. In a particular aspect, the compound is substantially purified (e.g. substantially free from substances that limit its effect or produce undesired side-effects). The subject is, for example, an animal, including but not limited to animals such as cows, pigs, horses, chickens, cats, dogs, etc., and is, for example, a mammal, such as a human. In a specific embodiment, a non-human mammal is the subject.

Formulations and methods of administration that can be employed when the compound comprises a nucleic acid are described above; additional appropriate formulations and routes of administration are described below.

Various delivery systems are known and can be used to administer a compound of the invention, e.g. encapsulation in liposomes, microparticles, microcapsules, recombinant cells capable of expressing the compound, receptor-mediated endocytosis (see, e.g. Wu and Wu, 1987, J. Biol. Chem. 262: 4429-4432), construction of a nucleic acid as part of a retroviral or other vector, etc. Methods of introduction can be enteral or parenteral and include but are not limited to intradermal, intramuscular, intraperitoneal, intravenous, subcutaneous, intranasal, epidural, and oral routes. The compounds may be administered by any convenient route, for example by infusion or bolus injection, by absorption through epithelial or mucocutaneous linings (e.g. oral mucosa, rectal and intestinal mucosa, etc.) and may be administered together with other biologically active agents. Administration can be systemic or local. In addition, it may be desirable to introduce the pharmaceutical compositions of the invention into the central nervous system by any suitable route, including intraventricular and intrathecal injection; intraventricular injection may be facilitated by an intraventricular catheter, for example, attached to a reservoir, such as an Ommaya reservoir. Pulmonary administration can also be employed, e.g. by use of an inhaler or nebulizer, and formulation with an aerosolizing agent.

In one aspect of the invention a nucleic acid employed in the invention may be delivered to the dermis, for example employing particle mediated epidermal delivery.

In a specific embodiment, it may be desirable to administer the pharmaceutical compositions of the invention locally to the area in need of treatment; this may be achieved, for example, and not by way of limitation, by local infusion during surgery, topical application, e.g. by injection, by means of a catheter, or by means of an implant, said implant being of a porous, non-porous, or gelatinous material, including membranes, such as sialastic membranes, or fibres.

In one embodiment, administration can be by direct injection into bladder, breast, colorectal, head and neck, kidney, lung or pancreatic tissue or at the site (or former site) of a malignant tumour or neoplastic or pre-neoplastic tissue.

In another embodiment, the compound can be delivered in a vesicle, in particular a liposome (see Langer, 1990, Science 249:1527-1533; Treat et al., in Liposomes in the Therapy of Infectious Disease and Cancer, Lopez-Berestein and Fidler (eds.), Liss, New York, pp. 353-365 (1989); Lopez-Berestein, ibid., pp. 317-327; see generally ibid.)

In yet another embodiment, the compound can be delivered in a controlled release system. In one embodiment, a pump may be used (see Langer, supra; Sefton, 1987, CRC Crit. Ref. Biomed. Eng. 14:201; Buchwald et al., 1980, Surgery 88:507; Saudek et al., 1989, N. Engl. J. Med. 321:574). In another embodiment, polymeric materials can be used (see Medical Applications of Controlled Release, Langer and Wise (eds.), CRC Pres., Boca Raton, Fla. (1974); Controlled Drug Bioavailability, Drug Product Design and Performance, Smolen and Ball (eds.), Wiley, New York (1984); Ranger and Peppas, J., 1983, Macromol. Sci. Rev. Macromol. Chem. 23:61; see also Levy et al., 1985, Science 228:190; During et al., 1989, Ann. Neurol. 25:351; Howard et al., 1989, J. Neurosurg. 71:105). In yet another embodiment, a controlled release system can be placed in proximity of the therapeutic target, i.e. the bladder, breast, colon, head and neck, kidney, lung or pancreas thus requiring only a fraction of the systemic dose (see, e.g. Goodson, in Medical Applications of Controlled Release, supra, vol. 2, pp. 115-138 (1984)).

Other controlled release systems are discussed in the review by Langer (1990, Science 249:1527-1533).

In a specific embodiment where the compound of the invention is a nucleic acid encoding a protein, the nucleic acid can be administered in vivo to promote expression of its encoded protein, by constructing it as part of an appropriate nucleic acid expression vector and administering it so that it becomes intracellular, e.g. by use of a retroviral vector (see U.S. Pat. No. 4,980,286), or by direct injection, or by use of microparticle bombardment (e.g. a gene gun; Biolistic, Dupont), or coating with lipids or cell-surface receptors or transfecting agents, or by administering it in linkage to a homeobox-like peptide which is known to enter the nucleus (see e.g. Joliot et al., 1991, Proc. Natl. Acad. Sci. USA 88:1864-1868), etc. Alternatively, a nucleic acid can be introduced intracellularly and incorporated within host cell DNA for expression, by homologous recombination.

The present invention also provides pharmaceutical compositions. Such compositions comprise a therapeutically effective amount of a compound, and a pharmaceutically acceptable carrier. In a specific embodiment, the term "pharmaceutically acceptable" means approved by a regulatory agency of the Federal or a state government or listed in the U.S. Pharmacopeia or other generally recognized pharmacopeia for use in animals, and more particularly in humans. The term "carrier" refers to a diluent, adjuvant, excipient, or vehicle with which the therapeutic is administered. Such pharmaceutical carriers can be sterile liquids, such as water and oils, including those of petroleum, animal, vegetable or synthetic origin, such as peanut oil, soybean oil, mineral oil, sesame oil and the like. Water is a preferred carrier when the pharmaceutical composition is administered intravenously. Saline solutions and aqueous dextrose and glycerol solutions can also be employed as liquid carriers, particularly for injectable solutions. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The composition, if desired, can also contain minor amounts of wetting or emulsifying agents, or pH buffering agents. These compositions can take the form of solutions, suspensions, emulsion, tablets, pills, capsules, powders, sustained-release formulations and the like. The composition can be formulated as a suppository, with traditional binders and carriers such as triglycerides. Oral formulation can include standard carriers such as pharmaceutical grades of mannitol, lactose, starch, magnesium stearate, sodium saccharine, cellulose, magnesium carbonate, etc. Examples of suitable pharmaceutical carriers are described in "Remington's Pharmaceutical Sciences" by E. W. Martin. Such compositions will contain a therapeutically effective amount of the compound, preferably in purified form, together with a suitable amount of carrier so as to provide the form for proper administration to the subject. The formulation should suit the mode of administration.

In one embodiment, for example where one or more antibodies are employed, the composition is formulated in accordance with routine procedures as a pharmaceutical composition adapted for intravenous administration to human beings. Typically, compositions for intravenous administration are solutions in sterile isotonic aqueous buffer. Where necessary, the composition may also include a solubilising agent and a local anaesthetic such as lidocaine to ease pain at the site of the injection. Generally, the ingredients are supplied either separately or mixed together in unit dosage form, for example, as a dry lyophilized powder or water free concentrate in a hermetically sealed container such as an ampoule or sachet indicating the quantity of active agent. Where the composition is to be administered by infusion, it can be dispensed with an infusion bottle containing sterile pharmaceutical grade water or saline. Where the composition is administered by injection, an ampoule of sterile water for injection or saline can be provided so that the ingredients may be mixed prior to administration.

The compounds of the invention can be formulated as neutral or salt forms. Pharmaceutically acceptable salts include those formed with free amino groups such as those derived from hydrochloric, phosphoric, acetic, oxalic, tartaric acids, etc., and those formed with free carboxyl groups such as those derived from sodium, potassium, ammonium, calcium, ferric hydroxides, isopropylamine, triethylamine, 2-ethylamino ethanol, histidine, procaine, etc.

The amount of the compound of the invention which will be effective in the treatment of bladder cancer, breast cancer, colorectal cancer, head and neck cancer, kidney cancer, lung cancer or pancreatic cancer can be determined by standard clinical techniques. In addition, in vitro assays may optionally be employed to help identify optimal dosage ranges. The precise dose to be employed in the formulation will also depend on the route of administration, and the seriousness of the disease or disorder, and should be decided according to the judgment of the practitioner and each subject's circumstances. However, suitable dosage ranges for intravenous administration are generally about 20-500 micrograms of active compound per kilogram body weight. Suitable dosage ranges for intranasal administration are generally about 0.01 pg/kg body weight to 1 mg/kg body weight. Effective doses may be extrapolated from dose-response curves derived from in vitro or animal model test systems.

Suppositories generally contain active ingredient in the range of 0.5% to 10% by weight; oral formulations preferably contain 10% to 95% active ingredient.

The invention also provides a pharmaceutical pack or kit comprising one or more containers filled with one or more of the ingredients of the pharmaceutical compositions of the invention. Optionally associated with such container(s) can be a notice in the form prescribed by a governmental agency regulating the manufacture, use or sale of pharmaceuticals or biological products, which notice reflects (a) approval by the agency of manufacture, use or sale for human administration, (b) directions for use, or both.

Thus in one aspect the kit comprises antibodies employed in the invention, for example the antibodies may be lyophilized for reconstitution before administration or use. Where the kit is for use in therapy/treatment such as cancer the antibody or antibodies may be reconstituted with an isotonic aqueous solution, which may optionally be provided with the kit. In one aspect the kit may comprise a polypeptide such as an immunogenic polypeptide employed in the invention, which may for example be lyophilized. The latter kit may further comprise an adjuvant for reconstituting the immunogenic polypeptide.

The invention also extends to a composition as described herein for example a pharmaceutical composition and/or vaccine composition for use in inducing an immune response in a subject.

Determining Abundance of Ephrin Type-A Receptor 10 by Imaging Technology

An advantage of determining abundance of Ephrin type-A receptor 10 by imaging technology may be that such a method is non-invasive (save that reagents may need to be administered) and there is no need to extract a sample from the subject.

Suitable imaging technologies include positron emission tomography (PET) and single photon emission computed tomography (SPECT). Visualisation of Ephrin type-A receptor 10 using such techniques requires incorporation or binding of a suitable label e.g. a radiotracer such as $^{18}$F, $^{11}$C or $^{123}$I (see e.g. NeuroRx—The Journal of the American Society for Experimental NeuroTherapeutics (2005) 2(2), 348-360 and idem pages 361-371 for further details of the techniques). Radiotracers or other labels may be incorporated into Ephrin type-A receptor 10 by administration to the subject (e.g. by injection) of a suitably labelled specific ligand. Alternatively they may be incorporated into a binding affinity reagent (e.g. an antibody) specific for Ephrin type-A receptor 10 which may be administered to the subject (e.g. by injection). For discussion of use of Affibodies for imaging see e.g. Orlova A, Magnusson M, Eriksson T L, Nilsson M, Larsson B, Hoiden-Guthenberg I, Widstrom C, Carlsson J, Tolmachev V, Stahl S, Nilsson F Y, Tumor imaging using a picomolar affinity HER2 binding Affibody molecule, Cancer Res. 2006 Apr. 15; 66(8): 4339-48).

Diagnosis and Treatment of Bladder Cancer, Breast Cancer, Colorectal Cancer, Head and Neck Cancer, Kidney Cancer, Lung Cancer or Pancreatic Cancer Using Immunohistochemistry Immunohistochemistry is an excellent detection technique and may therefore be very useful in the diagnosis and treatment of bladder cancer, breast cancer, colorectal cancer, head and neck cancer, kidney cancer, lung cancer or pancreatic cancer. Immunohistochemistry may be used to detect, diagnose, or monitor bladder cancer, breast cancer, colorectal cancer, head and neck cancer, kidney cancer, lung cancer or pancreatic cancer through the localization of Ephrin type-A receptor 10 antigens in tissue sections by the use of labelled antibodies (or other affinity reagents), derivatives and analogues thereof, which specifically bind to Ephrin type-A receptor 10, as specific reagents through antigen-antibody interactions that are visualized by a marker such as fluorescent dye, enzyme, radioactive element or colloidal gold.

The advancement of monoclonal antibody technology has been of great significance in assuring the place of immunohistochemistry in the modern accurate microscopic diagnosis of human neoplasms. The identification of disseminated neoplastically transformed cells by immunohistochemistry allows for a clearer picture of cancer invasion and metastasis, as well as the evolution of the tumour cell associated immunophenotype towards increased malignancy. Future antineoplastic therapeutic approaches may include a variety of individualized immunotherapies, specific for the particular immunophenotypical pattern associated with each individual patient's neoplastic disease. For further discussion see e.g. Bodey B, The significance of immunohistochemistry in the diagnosis and therapy of neoplasms, Expert Opin Biol Ther. 2002 April; 2(4):371-93.

The present invention may also be understood by reference to the following numbered paragraphs:

1. A method of detecting, diagnosing and/or screening for or monitoring the progression of bladder cancer, breast cancer, colorectal cancer, head and neck cancer, kidney cancer, lung cancer or pancreatic cancer or of monitoring the effect of an anti-bladder cancer, anti-breast cancer, anti-colorectal cancer, anti-head and neck cancer, anti-kidney cancer, anti-lung cancer or anti-pancreatic cancer drug or therapy in a subject which comprises detecting the presence or level of Ephrin type-A receptor 10, or one or more fragments thereof, or the presence or level of nucleic acid encoding Ephrin type-A receptor 10 or the presence or level of the activity of Ephrin type-A receptor 10 or which comprises detecting a change in the level thereof in said subject.

2. A method of detecting, diagnosing and/or screening for bladder cancer, breast cancer, colorectal cancer, head and neck cancer, kidney cancer, lung cancer or pancreatic cancer in a candidate subject which comprises detecting the presence of Ephrin type-A receptor 10, or one or more fragments thereof, or the presence of nucleic acid encoding Ephrin type-A receptor 10 or the presence of the activity of Ephrin type-A receptor 10 in said candidate subject, in which either (a) the presence of an elevated level of Ephrin type-A receptor 10 or said one or more fragments thereof or an elevated level of nucleic acid encoding Ephrin type-A receptor 10 or the presence of an elevated level of Ephrin type-A receptor 10 activity in the candidate subject as compared with the level in a healthy subject or (b) the presence of a detectable level of Ephrin type-A receptor 10 or said one or more fragments thereof or a detectable level of nucleic acid encoding Ephrin type-A receptor 10 or the presence of a detectable level of Ephrin type-A receptor 10 activity in the candidate subject as compared with a corresponding undetectable level in a healthy subject indicates the presence of bladder cancer, breast cancer, colorectal cancer, head and neck cancer, kidney cancer, lung cancer or pancreatic cancer in said subject.

3. A method of monitoring the progression of bladder cancer, breast cancer, colorectal cancer, head and neck cancer, kidney cancer, lung cancer or pancreatic cancer in a subject or of monitoring the effect of an anti-bladder cancer, anti-breast cancer, anti-colorectal cancer, anti-head and neck cancer, anti-kidney cancer, anti-lung cancer or anti-pancreatic cancer drug or therapy which comprises detecting the presence of Ephrin type-A receptor 10, or one or more fragments thereof, or the presence of nucleic acid encoding Ephrin type-A receptor 10 or the presence of the activity of Ephrin type-A receptor 10 in said candidate subject at a first time point and at a later time point, the presence of an elevated or lowered level of Ephrin type-A receptor 10 or said one or more fragments thereof or an elevated or lowered level of nucleic acid encoding Ephrin type-A receptor 10 or the presence of an elevated or lowered level of Ephrin type-A receptor 10 activity in the subject at the later time point as compared with the level in the subject at said first time point, indicating the progression or regression of bladder cancer, breast cancer, colorectal cancer, head and neck cancer, kidney cancer, lung cancer or pancreatic cancer or indicating the effect or non-effect of an anti-bladder cancer, anti-breast cancer, anti-colorectal cancer, anti-head and neck cancer, anti-kidney cancer, anti-lung cancer or anti-pancreatic cancer drug or therapy in said subject.

4. A method according to any one of paragraphs 1 to 3 wherein the presence of Ephrin type-A receptor 10, or one or more fragments thereof, or the presence of nucleic acid encoding Ephrin type-A receptor 10 or the presence of the activity of Ephrin type-A receptor 10 is detected by analysis of a biological sample obtained from said subject.

5. A method according to paragraph 4 which includes the step of obtaining said sample for analysis from said subject.

6. A method according to paragraph 4 or paragraph 5 wherein the sample is a sample of bladder, breast, colorectal, head and neck, kidney, lung or pancreatic tissue.

7. A method according to any one of paragraphs 1 to 6 wherein the presence of Ephrin type-A receptor 10, or one or more fragments thereof, or the presence of nucleic acid encoding Ephrin type-A receptor 10 or the presence of the activity of Ephrin type-A receptor 10 is detected quantitatively.

8. A method according to paragraph 7 wherein the presence of Ephrin type-A receptor 10, or one or more fragments thereof, or the presence of nucleic acid encoding Ephrin type-A receptor 10 or the presence of the activity of Ephrin type-A receptor 10 is detected quantitatively by means involving use of an imaging technology.

9. A method according to any one of paragraphs 1 to 7 involving use of immunohistochemistry on tissue sections in order to determine the presence of Ephrin type-A receptor 10, or one or more fragments thereof, or the presence of nucleic acid encoding Ephrin type-A receptor 10 or the presence of the activity of Ephrin type-A receptor 10, and thereby to localise bladder cancer, breast cancer, colorectal cancer, head and neck cancer, kidney cancer, lung cancer or pancreatic cancer cells.

10. A method according to any one of paragraphs 1 to 3 wherein the presence of Ephrin type-A receptor 10, or one or more fragments thereof, or the presence of nucleic acid encoding Ephrin type-A receptor 10 or the presence of the activity of Ephrin type-A receptor 10 is detected by analysis in situ.

11. A method according to any one of paragraphs 1 to 10 wherein the presence of Ephrin type-A receptor 10 or one or more epitope-containing fragments thereof is detected.

12. A method according to paragraph 11 wherein the presence of Ephrin type-A receptor 10 or one or more fragments thereof is detected using an affinity reagent capable of specific binding to Ephrin type-A receptor 10 or one or more fragments thereof.

13. A method according to paragraph 12 wherein the affinity reagent is an antibody.

14. A method according to any one of paragraphs 1 to 10 wherein nucleic acid encoding Ephrin type-A receptor 10 is detected.

15. A method according to paragraph 14 wherein nucleic acid encoding Ephrin type-A receptor 10 is detected using a hybridizing agent capable of hybridizing to nucleic acid encoding Ephrin type-A receptor 10.

16. A method according to any one of paragraphs 1 to 10 wherein the activity of Ephrin type-A receptor 10 is detected.

17. A method of detecting, diagnosing and/or screening for or monitoring the progression of bladder cancer, breast cancer, colorectal cancer, head and neck cancer, kidney cancer, lung cancer or pancreatic cancer or of monitoring the effect of an anti-bladder cancer, anti-breast cancer, anti-colorectal cancer, anti-head and neck cancer, anti-kidney cancer, anti-lung cancer or anti-pancreatic cancer drug or therapy in a subject which comprises detecting the presence or level of antibodies capable of immunospecific binding to Ephrin type-A receptor 10, or one or more epitope-containing fragments thereof or which comprises detecting a change in the level thereof in said subject.

18. A method of detecting, diagnosing and/or screening for bladder cancer, breast cancer, colorectal cancer, head and neck cancer, kidney cancer, lung cancer or pancreatic cancer in a subject which comprises detecting the presence of antibodies capable of immunospecific binding to Ephrin type-A receptor 10, or one or more epitope-containing fragments thereof in said subject, in which (a) the presence of an elevated level of antibodies capable of immunospecific binding to Ephrin type-A receptor 10 or said one or more epitope-containing fragments thereof in said subject as compared with the level in a healthy subject or (b) the presence of a detectable level of antibodies capable of immunospecific binding to Ephrin type-A receptor 10 or said one or more epitope-containing fragments thereof in said subject as compared with a corresponding undetectable level in a healthy subject indicates the presence of bladder cancer, breast cancer, colorectal cancer, head and neck cancer, kidney cancer, lung cancer or pancreatic cancer in said subject.

19. A method of monitoring the progression of bladder cancer, breast cancer, colorectal cancer, head and neck cancer, kidney cancer, lung cancer or pancreatic cancer or of monitoring the effect of an anti-bladder cancer, anti-breast cancer, anti-colorectal cancer, anti-head and neck cancer, anti-kidney cancer, anti-lung cancer or anti-pancreatic cancer drug or therapy in a subject which comprises detecting the presence of antibodies capable of immunospecific binding to Ephrin type-A receptor 10, or one or more epitope-containing fragments thereof in said subject at a first time point and at a later time point, the presence of an elevated or lowered level of antibodies capable of immunospecific binding to Ephrin type-A receptor 10, or one or more epitope-containing fragments thereof in said subject at the later time point as compared with the level in said subject at said first time point, indicating the progression or regression of bladder cancer, breast cancer, colorectal cancer, head and neck cancer, kidney cancer, lung cancer or pancreatic cancer or the effect or non-effect of an anti-bladder cancer, anti-breast cancer, anti-colorectal cancer, anti-head and neck cancer, anti-kidney cancer, anti-lung cancer or anti-pancreatic cancer drug or therapy in said subject.

20. A method according to any one of paragraphs 17 to 19 wherein the presence of antibodies capable of immunospecific binding to Ephrin type-A receptor 10, or one or more epitope-containing fragments thereof is detected by analysis of a biological sample obtained from said subject.

21. A method according to paragraph 20 which includes the step of obtaining said sample for analysis from said subject.

22. A method according to paragraph 20 or paragraph 21 wherein the sample is a sample of bladder, breast, colorectal, head and neck, kidney, lung or pancreatic tissue.

23. A method according to any one of paragraphs 1 to 22 wherein the level that may be detected in the candidate subject who has bladder cancer, breast cancer, colorectal cancer, head and neck cancer, kidney cancer, lung cancer or pancreatic cancer is 2 or more fold higher than the level in the healthy subject.

24. An agent capable of specific binding to Ephrin type-A receptor 10, or a fragment thereof, or a hybridising agent capable of hybridizing to nucleic acid encoding Ephrin type-A receptor 10 or an agent capable of detecting the activity of Ephrin type-A receptor 10 for use in screening for, detecting and/or diagnosing disease.

25. An agent according to paragraph 24 wherein the disease is cancer.

26. An agent according to paragraph 25 wherein the cancer is bladder cancer, breast cancer, colorectal cancer, head and neck cancer, kidney cancer, lung cancer or pancreatic cancer.

27. Ephrin type-A receptor 10, or a fragment thereof for use in screening for, detecting and/or diagnosing disease.

28. Ephrin type-A receptor 10, or a fragment thereof according to paragraph 27 wherein the disease is cancer.

29. Ephrin type-A receptor 10, or a fragment thereof according to paragraph 28 wherein the cancer is bladder cancer, breast cancer, colorectal cancer, head and neck cancer, kidney cancer, lung cancer or pancreatic cancer.

30. An affinity reagent capable of specific binding to Ephrin type-A receptor 10 or a fragment thereof.

31. An affinity reagent according to paragraph 30 which contains or is conjugated to a detectable label.
32. An affinity reagent according to paragraph 30 which contains or is conjugated to a therapeutic moiety.
33. An affinity reagent according to paragraph 32 wherein the therapeutic moiety is a cytotoxic moiety.
34. An affinity reagent according to any one of paragraphs 30 to 33 which is an antibody.
35. An antibody according to paragraph 34, which is a monoclonal antibody.
36. A monoclonal antibody according to paragraph 35, which has cytotoxicity against Ephrin type-A receptor 10 antigen expressing cells in the presence of a human complement.
37. A monoclonal antibody according to paragraph 35, which has cytotoxicity against Ephrin type-A receptor 10 antigen expressing cells in the presence of human immune effector cells.
38. A hybridizing agent capable of hybridizing to nucleic acid encoding Ephrin type-A receptor 10.
39. A hybridizing agent according to paragraph 38 which contains or is conjugated to a detectable label.
40. A kit containing one or more affinity reagents and/or hybridizing agents according to any one of paragraphs 30 to 39 together with instructions for their use in a method according to any one of paragraphs 1 to 16 and 23.
41. A kit according to paragraph 40 further containing reagents capable of detecting and reporting the binding of said affinity reagents and/or hybridizing agents to their binding partners.
42. A kit containing Ephrin type-A receptor 10 and/or one or more fragments thereof together with instructions for their use in a method according to any one of paragraphs 17 to 23.
43. A kit containing one or more agents capable of detecting the activity of Ephrin type-A receptor 10 together with instructions for their use in a method according to any one of paragraphs 1 to 16 and 23.
44. A pharmaceutical composition comprising a therapeutically effective amount of an affinity reagent capable of specific binding to Ephrin type-A receptor 10 or a fragment thereof, and a pharmaceutically acceptable diluent or carrier.
45. A pharmaceutical composition comprising one or more affinity reagents or hybridizing reagents according to any one of paragraphs 30 to 39 and a pharmaceutically acceptable diluent or carrier.
46. An immunogenic composition comprising Ephrin type-A receptor 10 or an epitope containing fragment thereof, or nucleic acid encoding Ephrin type-A receptor 10 or a fragment thereof optionally together with an immunostimulant.
47. A vaccine composition comprising Ephrin type-A receptor 10 or an epitope containing fragment thereof, or nucleic acid encoding Ephrin type-A receptor 10 or an epitope containing fragment thereof optionally together with an immunostimulant.
48. A method of raising an immune response which comprises administering to a subject a composition according to paragraph 46.
49. A method for treating or preventing bladder cancer, breast cancer, colorectal cancer, head and neck cancer, kidney cancer, lung cancer or pancreatic cancer which comprises administering to a subject in need thereof a therapeutically effective amount of a composition according to any one of paragraphs 44 to 47.
50. A composition according to any one of paragraphs 44 to 47 for use in preventing or treating bladder cancer, breast cancer, colorectal cancer, head and neck cancer, kidney cancer, lung cancer or pancreatic cancer.
51. A method of screening for compounds that modulate the activity of Ephrin type-A receptor 10, the method comprising: (a) contacting Ephrin type-A receptor 10 or a biologically active portion thereof with a candidate compound; and (b) determining whether activity of Ephrin type-A receptor 10 is thereby modulated.
52. A method according to paragraph 51 wherein the activity is kinase activity.
53. A method according to paragraph 51 or 52 which comprises (a) contacting Ephrin type-A receptor 10 or a biologically active portion thereof with a candidate compound in a sample; and (b) comparing the activity of Ephrin type-A receptor 10 or a biologically active portion thereof in said sample after contact with said candidate compound with the activity of Ephrin type-A receptor 10 or a biologically active portion thereof in said sample before contact with said candidate compound, or with a reference level of activity.
54. A method according to any one of paragraphs 51-53 which is a method of screening for compounds that inhibit activity of Ephrin type-A receptor 10.
55. A method according to any one of paragraphs 51 to 54 wherein Ephrin type-A receptor 10 or a biologically active portion thereof is expressed on or by a cell.
56. A method according to any one of paragraphs 51 to 54 wherein Ephrin type-A receptor 10 or a biologically active portion thereof is isolated from cells which express it.
57. A method according to paragraph 56 wherein Ephrin type-A receptor 10 or a biologically active portion thereof is immobilised onto a solid phase.
58. A method of screening for compounds that modulate the expression of Ephrin type-A receptor 10 or nucleic acid encoding Ephrin type-A receptor 10, the method comprising: (a) contacting cells expressing Ephrin type-A receptor 10 or nucleic acid encoding Ephrin type-A receptor 10 with a candidate compound; and (b) determining whether expression of Ephrin type-A receptor 10 or nucleic acid encoding Ephrin type-A receptor 10 is thereby modulated.
59. A method according to paragraph 58 which comprises (a) contacting cells expressing Ephrin type-A receptor 10 or nucleic acid encoding Ephrin type-A receptor 10 with a candidate compound in a sample; and (b) comparing the expression of Ephrin type-A receptor 10 or nucleic acid encoding Ephrin type-A receptor 10 by cells in said sample after contact with said candidate compound with the expression of Ephrin type-A receptor 10 or nucleic acid encoding Ephrin type-A receptor 10 of cells in said sample before contact with said candidate compound, or with a reference level of expression.
60. A method according to paragraph 58 or paragraph 59 which is a method of screening for compounds that inhibit expression of Ephrin type-A receptor 10 or nucleic acid encoding Ephrin type-A receptor 10.
61. A compound obtainable by a method according to any one of paragraphs 51 to 60.
62. A compound which modulates the activity or expression of Ephrin type-A receptor 10 or nucleic acid encoding Ephrin type-A receptor 10.

63. A compound according to paragraph 62 which inhibits the activity or expression of Ephrin type-A receptor 10 or nucleic acid encoding Ephrin type-A receptor 10.
64. A compound according to any one of paragraphs 58 to 63 for use in treating or preventing bladder cancer, breast cancer, colorectal cancer, head and neck cancer, kidney cancer, lung cancer or pancreatic cancer.
65. A method for treating or preventing bladder cancer, breast cancer, colorectal cancer, head and neck cancer, kidney cancer, lung cancer or pancreatic cancer which comprises administering to a subject in need thereof a therapeutically effective amount of a compound according to any one of paragraphs 58 to 63.

Preferred features of each aspect of the invention are as for each of the other aspects mutatis mutandis. The prior art documents mentioned herein are incorporated to the fullest extent permitted by law.

EXAMPLE 1

Identification of Membrane Proteins Expressed in Colorectal Cancer, Kidney Cancer or Lung Cancer Blood and Tissue Samples Using the following Reference Protocol, membrane proteins extracted from colorectal cancer, kidney cancer and lung cancer tissue and normal adjacent colorectal, kidney and lung tissue samples were digested, labelled with Isotope Tagging for Absolute & Relative Quantitation reagents (iTRAQT™; Applied Biosystems, Foster City, Calif., USA) and resulting peptides sequenced by tandem mass spectrometry.
1.1 Materials and Methods
1.1.1—Plasma Membrane Fractionation The cells recovered from a colorectal cancer, kidney cancer or lung cancer or normal adjacent colorectal, kidney or lung tissue were lysed and submitted to centrifugation at 1000 G. The supernatant was taken, and it was subsequently centrifuged at 3000 G. Once again, the supernatant was taken, and it was then centrifuged at 100 000 G.

The resulting pellet was recovered and put on 15-60% sucrose gradient.

A Western blot was used to identify sub cellular markers, and the Plasma Membrane fractions were pooled.

The pooled solution was then analysed directly by iTRAQT™ (see section 1.1.2 below).
1.1.2—TRAQ Methodology Membrane protein pellets from colorectal cancer, kidney cancer or lung cancer and normal adjacent colorectal, kidney or lung tissue were solubilised in sample buffer (2-4 µg/µl in 0.5% SDS) by the addition of buffer and then heating to 95° C. for 3 min.

To a volume of each protein solution equating to 50 µg, 150 µl of 0.5M triethylammonium bicarbonate (TEAB) solution was added. To each sample, 3 µl of 50 mM tris-(2-carboxyethyl)phosphine was added and the mixture was incubated at 60° C. for 1 hour. 1 µl of cysteine blocking reagent, 200 mM methyl methanethiosulphonate (MMTS) in isopropanol, was then added. After incubation at room temperature for 10 minutes, 15 µl of 1 µg/µl trypsin was added to each sample followed by incubation at 37° C. overnight.

The digested samples were dried under a vacuum and re-constituted with 30 µl of 0.5M TEAB solution. 70 µl ethanol was added to each of the four iTRAQ™ reagents (114/115/116/117) and one reagent added to each of the four samples analysed (two colorectal cancer, kidney cancer or lung cancer samples and two corresponding normal adjacent tissue samples) and left at room temperature for 1 hour. The specific reagent added to each sample was recorded. The four labeled samples were combined & vortexed.

The combined sample was reduced to dryness under a vaccum and de-salted by loading onto a C18 spin column, washing with aqueous solvent and then eluting with 70% acetonitrile. The sample fraction was again reduced to dryness and then re-dissolved in 40 µl of solvent A (97.9 water, 2% acetonitrile, 0.1% formic acid) prior to ion exchange fractionation.
1.1.3—Fractionation and Analysis of Labelled Peptides The sample was fractionated by strong cation exchange chromatography using an Agilent 1200 chromatograph (Agilent, Santa Clara, Calif., USA). Samples were eluted off an Agilent Zorbax Bio-SCXII column (3.5 µm; 50×0.8 mm) using a 200 min gradient of 0-100 mM sodium acetate over 20 minutes and then to 1M over 10 minutes. 1 minute fractions were collected over the 30 minute run.

Each fraction was analysed by liquid chromatography/mass spectrometry using an Agilent 1200 chromatograph fitted with a Zorbax 300SB-C18 (150 mm×75 µm) and an Agilent 6510 quadrupole—time-of-flight instrument (Agilent, Santa Clara, Calif., USA). Peptides were eluted with a 300nl/min gradient increasing from 15% to 45% acetonitrile in 60 minutes. Data was acquired in auto MS/MS mode such that up to 3 precursor ions above the intensity threshold were selected and product ion spectra accumulated to facilitate the sequencing of the labelled peptides. Raw was processed to create peak lists using Spectrum Mill software (Agilent, Santa Clara, Calif., USA).
1.1.4—Amino Acid Sequence Analysis of Labelled Peptides For partial amino acid sequencing and identification of Ephrin type-A receptor 10, uninterpreted tandem mass spectra of tryptic peptides were searched using the SEQUEST search program (Eng et al., 1994, J. Am. Soc. Mass Spectrom. 5:976-989). Criteria for database identification included: the cleavage specificity of trypsin; the detection of a suite of a, b and y ions in peptides returned from the database, and a mass increment for all cysteine residues to account for modification with methyl methanethiosulphonate and the addition of iTRAQ™ labels to free amines (N-terminus & lysine). The data was searched through IPI Human v3.23 (world wide web.ebi.ac.uk/IPI/IPIhuman.html).
1.1.5—Discrimination of Colorectal Cancer, Kidney Cancer or Lung Cancer Associated Proteins The process to identify Ephrin type-A receptor 10 uses the peptide sequences obtained experimentally by mass spectrometry described above of naturally occurring human proteins to identify and organize coding exons in the published human genome sequence.

Recent dramatic advances in defining the chemical sequence of the human genome have led to the near completion of this immense task (Venter, J. C. et al. (2001). The sequence of the human genome. Science 16: 1304-51; International Human Genome Sequencing Consortium. (2001). Initial sequencing and analysis of the human genome Nature 409: 860-921). There is little doubt that this sequence information will have a substantial impact on our understanding of many biological processes, including molecular evolution, comparative genomics, pathogenic mechanisms and molecular medicine. For the full medical value inherent in the sequence of the human genome to be realised, the genome needs to be 'organised' and annotated. By this, is meant at least the following three things: (i) The assembly of the sequences of the individual portions of the genome into a coherent, continuous sequence for each chromosome. (ii) The unambiguous identification of those regions of each chromosome that contain genes. (iii) Determination of the fine structure of the genes and the properties of its mRNA and protein products. While the definition of a 'gene' is an increasingly complex issue (H Pearson: What is a gene? Nature (2006) 24: 399-401), what is of immediate interest for drug discovery and development is a catalogue of those genes that encode functional, expressed proteins. A subset of these genes will be involved in the molecular basis of most if not all pathologies. Therefore an important and immediate goal for the pharmaceutical industry is to identify all such genes in the human genome and describe their fine structure.

Processing and Integration of Peptide Masses, Peptide Signatures, ESTs and Public Domain Genomic Sequence Data to Form OGAP® Database Discrete genetic units (exons, transcripts and genes) were identified using the following sequential steps:

1. A 'virtual transcriptome' is generated, containing the tryptic peptides which map to the human genome by combining the gene identifications available from Ensembl and various gene prediction programs. This also incorporates SNP data (from dbSNP) and all alternate splicing of gene identifications. Known contaminants were also added to the virtual transcriptome.
2. All tandem spectra in the OGeS Mass Spectrometry Database are interpreted in order to produce a peptide that can be mapped to one in the virtual transcriptome. A set of automated spectral interpretation algorithms were used to produce the peptide identifications.
3. The set of all mass-matched peptides in the OGeS Mass Spectrometry Database is generated by searching all peptides from transcripts hit by the tandem peptides using a tolerance based on the mass accuracy of the mass spectrometer, typically 20 ppm.
4. All tandem and mass-matched peptides are combined in the form of "protein clusters". This is done using a recursive process which groups sequences into clusters based on common peptide hits. Biological sequences are considered to belong to the same cluster if they share one or more tandem or mass-matched peptide.
5. After initial filtering to screen out incorrectly identified peptides, the resulting clusters are then mapped on the human genome.
6. The protein clusters are then aggregated into regions that define preliminary gene boundaries using their proximity and the co-observation of peptides within protein clusters. Proximity is defined as the peptide being within 80,000 nucleotides on the same strand of the same chromosome. Various elimination rules, based on cluster observation scoring and multiple mapping to the genome are used to refine the output. The resulting 'confirmed genes' are those which best account for the peptides and masses observed by mass spectrometry in each cluster. Nominal co-ordinates for the gene are also an output of this stage.
7. The best set of transcripts for each confirmed gene are created from the protein clusters, peptides, ESTs, candidate exons and molecular weight of the original protein spot.
8. Each identified transcript was linked to the sample providing the observed peptides.
9. Use of an application for viewing and mining the data. The result of steps 1-8 was a database containing genes, each of which consisted of a number of exons and one or more transcripts. An application was written to display and search this integrated genome/proteome data. Any features (OMIM disease locus, InterPro etc.) that had been mapped to the same Golden Path co-ordinate system by Ensembl could be cross-referenced to these genes by coincidence of location and fine structure.

Results

The process was used to generate approximately 1 million peptide sequences to identify protein-coding genes and their exons resulted in the identification of protein sequences for 18083 genes across 67 different tissues and 56 diseases including 501 genes in B-cell non-Hodgkin's lymphoma, 506 genes in bladder cancer, 4,713 genes in breast cancer, 766 genes in Burkitt's lymphoma, 1,371 genes in cervical cancer, 949 genes in colorectal cancer, 1,782 genes in hepatocellular carcinoma, 2,424 genes in chronic lymphocytic leukaemia, 1,004 genes in kidney cancer, 978 genes in lung cancer, 1,764 genes in melanoma, 1,033 genes in ovarian cancer, 2,961 genes in pancreatic cancer and 3,307 genes in prostate cancer, illustrated here by Ephrin type-A receptor 10 isolated and identified from colorectal cancer, kidney cancer and lung cancer samples. Following comparison of the experimentally determined sequences with sequences in the OGAP® database, Ephrin type-A receptor 10 showed a high degree of specificity to colorectal cancer, kidney cancer and lung cancer indicative of the prognostic and diagnostic nature.

1.2 Results

These experiments identified Ephrin type-A receptor 10, as further described herein. The full-length Ephrin type-A receptor 10 was detected in the plasma membrane of colorectal cancer, kidney cancer and lung cancer samples. The iTRAQ analysis showed that levels of Ephrin type-A receptor 10 in the cancer samples were higher than in the matched normal adjacent tissue samples.

The Protein Index was calculated for Ephrin type-A receptor 10. For each gene, the protein index uses the mass spectrometry data to assign a score to each disease, relative to the global database. The Protein Index can then be used to identify cancer specific genes with a high score in cancer indications and low/negligible scores in normal and other diseases. The index contains ~1 million peptides sequenced via mass spectrometry from 56 diseases. For each gene, this yields a score for each disease and subcellular location.

The Protein Index for Ephrin type-A receptor 10 is high in colorectal cancer, medium in kidney cancer and high in lung cancer plasma membrane and very low in normal plasma membrane. Ephrin type-A receptor 10 was not detected in any other diseases. This indicates that Ephrin type-A receptor 10 is potentially a good marker for colorectal cancer, kidney cancer and lung cancer.

EXAMPLE 2

Immunohistochemistry Using Antibody to Ephrin Type-A Receptor 10

Using the following Reference Protocol, immunohistochemistry was performed on FFPE tumour and normal tissues using a mouse monoclonal antibody to Ephrin type-A receptor 10. Antibodies to Ephrin type-A receptor 10 (as defined by SEQ ID No: 1) were developed at Biosite.

2.1 Materials and Methods

Anti-mouse EnVision™ plus kit (K4006) was from DAKO, CA, USA.

EX-De-Wax was from BioGenex, CA, USA.

Tissue sections and arrays were from Biomax, MD, USA.

2.1.1—Deparaffinisation and Rehydration

Slides were heated for 2 h at 60° C. in 50 ml Falcons in a water bath with no buffer. Each Falcon had one slide or two slides back-to back with long gel loading tip between them to prevent slides from sticking to each other. Slides were deparaffinised in EZ-DeWax for 5 min in black slide rack, then rinsed well with the same DeWax solution using 1 ml pipette, then washed with water from the wash bottle. Slides were placed in a coplin jar filled with water; the water was changed a couple of times.

2.1.2—Antigen Retrieval

Water was exchanged for antigen retrieval solution=1× citrate buffer, pH 6 (DAKO). Antigen was retrieved by the water bath method. The slides in the plastic coplin jar in antigen retrieval solution were placed into a water bath which was then heated up from 60° C. to 90° C. The slides were incubated at 90° C. for 20 min and then left to cool down at room temperature for 20 min. The slides were washed 1×5 min with PBS-3T (0.5 L PBS+3 drops of Tween-20) and placed in PBS.

2.1.3.—Staining

After antigen retrieval, slides were mounted in the Shandon Coverplate system. Trapping of air bubbles between the slide and plastic coverplate was prevented by placing the coverplate into the coplin jar filled with PBS and gently sliding the slide with tissue sections into the coverplate. The slide was pulled out of the coplin jar while holding it tightly together with the coverplate. The assembled slide was placed into the rack, letting PBS trapped in the funnel and between the slide and coverplate to run through. Slides were washed with 2×2 ml (or 4×1 ml) PBS-3T, 1×2 ml PBS, waiting until all PBS had gone through the slide and virtually no PBS was left in the funnel.

Endogenous peroxide blockade was performed using solution supplied with EnVision™+kits. 1-4 drops of peroxide solution was used per slide; the incubation time was 5 minutes. The slides were rinsed with water and then once with 2 ml PBS-3T, and once with 2 ml PBS; it was important to wait until virtually no liquid was left in the funnel before adding a new portion of wash buffer.

The primary antibody was diluted with an Antibody diluent reagent (DAKO). Optimal dilution was determined to be 1:30 (antibody stock 0.75 mg/ml). Up to 200 µl of diluted primary antibody was applied to each slide and incubated for 45 minutes at room temperature. Slides were washed with 2×2 ml (or 4×1 ml) PBS-3T and then 1×2 ml PBS.

The anti-mouse peroxidase polymer was applied 2×2 drops per slide and incubated for 35 min at room temperature. The slides were washed as above.

The DAB substrate was made up in dilution buffer; 2 ml containing 2 drops of substrate was enough for 10 slides. The DAB reagent was applied to the slides by applying a few drops at a time and left for 10 min. The slides were washed 1×2 ml (or 2×1 ml) with PBS-3T and 1×2 ml (or 2×1 ml) with PBS.

Hematoxylin (DAKO) was applied; 1 ml was enough for 10 slides and slides were incubated for 1 min at room temperature. The funnels of the Shandon Coverplate system were filled with 2 ml of water and let to run through. When slides were clear of the excess of hematoxylin, the system was disassembled, tissue sections and/or arrays were washed with water from the wash bottle and placed into black slide rack. Tissues were dehydrated by incubating in EZ-DeWax for 5 min and then in 95% ethanol for 2-5 min.

Slides were left to dry on the bench at room temperature and then mounted in mounting media and covered with coverslip.

2.2 Results

Immunohistochemical analysis using antibody 0G0036Z1ZM01731, generated by Biosite, revealed specific staining of tumour cells in bladder cancer, breast cancer, colorectal cancer, head and neck cancer, kidney cancer, non-small cell lung cancer and pancreatic cancer.

Table 2 below shows the results of a high density array containing 500 tissue cores from the 20 most common types of cancer (20 cases/type) and normal controls (5 cases/type). Elevated staining of Ephrin type-A receptor 10 in cancer cells was seen in bladder cancer, breast cancer, colorectal cancer, head and neck cancer, kidney cancer, non-small cell lung cancer and pancreatic cancer.

TABLE 2

Ephrin type-A receptor 10 scoring on tissue microarray (Biomax, US). Multiple organ cancer tissue array with normal tissues
(− = no staining; + = weak staining;
++ = moderate staining;
+++ = strong staining).

| Tissue | Tumour (%) | | | |
|---|---|---|---|---|
|  | + | ++ | +++ | Total + |
| Kidney | 10 | 40 | 40 | 90 |
| Head and neck | 11 | 11 | 50 | 72 |
| Bladder | 5 | 10 | 50 | 65 |
| Colon | 5 | 14 | 33 | 52 |
| Non-Small Cell Lung | 16 | 16 | 36 | 68 |
| Pancreas | 65 | 20 | 10 | 95 |
| Breast | 11 | 23 | 9 | 43 |
| Skin | 0 | 4 | 33 | 37 |
| Thyroid | 20 | 20 | 20 | 60 |
| Ovary | 18 | 6 | 12 | 35 |
| Uterus | 30 | 25 | 5 | 60 |
| Lymph node | 0 | 30 | 0 | 30 |
| Liver | 35 | 0 | 0 | 35 |
| Testis | 35 | 0 | 0 | 35 |
| Retroperitoneum | 20 | 0 | 0 | 20 |
| Stomach | 4 | 0 | 0 | 4 |
| Bone | 0 | 0 | 0 | 0 |
| Cerebrum | 0 | 0 | 0 | 0 |
| Fatty tissue | 0 | 0 | 0 | 0 |
| Fibrous tissue | 0 | 0 | 0 | 0 |
| Intestine | 0 | 0 | 0 | 0 |
| Mesentery | 0 | 0 | 0 | 0 |
| Prostate | 0 | 0 | 0 | 0 |
| Spleen | 0 | 0 | 0 | 0 |

All references referred to in this application, including patent and patent applications, are incorporated herein by reference to the fullest extent possible.

Throughout the specification and the claims which follow, unless the context requires otherwise, the word 'comprise', and variations such as 'comprises' and 'comprising', will be understood to imply the inclusion of a stated integer, step, group of integers or group of steps but not to the exclusion of any other integer, step, group of integers or group of steps.

Embodiments of the invention are described herein, which comprise certain elements. The invention also extends to separate embodiments consisting of or consisting essentially of the same elements, and vice versa.

The application of which this description and claims form part may be used as a basis for priority in respect of any subsequent application. The claims of such subsequent application may be directed to any feature or combination of features described herein. They may take the form of product, composition, process, or use claims and may include, by way of example and without limitation, the following claims:

SEQUENCE LISTING

| Sequence | Sequence ID |
|---|---|
| METCAGPHPLRLFLCRMQLCLALLLGPWRP GTAEEVILLDSKASQAELGWTALPSNGWEE ISGVDEHDRPIRTYQVCNVLEPNQDNWLQT GWISRGRGQRIFVELQFTLRDCSSIPGAAG TCKETFNVYYLETEADLGRGRPRLGGSRPR KIDTIAADESFTQGDLGERKMKLNTEVREI GPLSRRGFHLAFQDVGACVALVSVRVYYKQ CRATVRGLATFPATAAESAFSTLVEVAGTC VAHSEGEPGSPPRMHCGADGEWLVPVGRCS CSAGFQERGDFCEACPPGFYKVSPRRPLCS PCPEHSRALENASTFCVCQDSYARSPTDPP SASCTRPPSAPRDLQYSLSRSPLVLRLRWL PPADSGGRSDVTYSLLCLRCGREGPAGACE PCGPRVAFLPRQAGLRERAATLLHLRPGAR YTVRVAALNGVSGPAAAAGTTYAQVTVSTG PGAPWEEGEIRRDRVEPQSVSLSWREPIPA GAPGANDTEYEIRYYEKGQSEQAYSMVKTG APTVTVTNLKPATRYVFQIRAASPGPSWEA QSFNPSIEVQTLGEAASGSRDQSPAIVVTV VTISALLVLGSVMSVLAIWRRPCSYGKGGG DAHDEEELYFHFKVPTRRTFLDPQSCGDLL QAVHLFAKELDAKSVTLERSLGGGRFGELC CGCLQLPGRQELLVAVHMLRDSASDSQRLG FLAEALTLGQFDHSHIVRLEGVVTRGSTLM IVTEYMSHGALDGFLRRHEGQLVAGQLMGL LPGLASAMKYLSEMGYVHRGLAARHVLVSS DLVCKISGFGRGPRDRSEAVYTTMSGRSPA LWAAPETLQFGHFSSASDVWSFGIIMWEVM AFGERPYWDMSGQDVIKAVEDGFRLPPPRN CPNLLHRLMLDCWQKDPGERPRFSQIHSIL SKMVQDPEPPKCALTTCPRPPTPLADRAFS TFPSFGSVGAWLEALDLCRYKDSFAAAGYG SLEAVAEMTAQDLVSLGISLAEHREALLSG ISALQARVLQLQGQGVQV | 1 |
| EIGPLSR | 2 |
| FSQIHSILSKMVQDPEPPK | 3 |
| HEGQLVAGQLMGLLPGLASAMK | 4 |
| LEGVVTR | 5 |
| SPLVLR | 6 |

The invention claimed is:

1. A method for treating a cancer wherein Ephrin type-A receptor 10 is overexpressed and the cancers are selected from bladder cancer, breast cancer, colorectal cancer, head and neck cancer, kidney cancer, lung cancer or pancreatic cancer, the method comprising administering to a subject in need thereof a therapeutically effective amount of a composition comprising an antibody that specifically binds to Ephrin type-A receptor 10, wherein said antibody comprises a conjugated cytotoxic agent, and a pharmaceutically acceptable diluent or carrier wherein said treatment is cytotoxicity.

2. A method according to claim 1 wherein said antibody is selected from the group consisting of an isolated monoclonal antibody, an antibody fragment, a humanized antibody and a chimeric antibody.

* * * * *

SEQUENCE LISTING

<160> NUMBER OF SEQ ID NOS: 7

<210> SEQ ID NO 1
<211> LENGTH: 1008
<212> TYPE: PRT
<213> ORGANISM: Homo sapiens

<400> SEQUENCE: 1

```
Met Glu Thr Cys Ala Gly Pro His Pro Leu Arg Leu Phe Leu Cys Arg
1               5                   10                  15

Met Gln Leu Cys Leu Ala Leu Leu Leu Gly Pro Trp Arg Pro Gly Thr
                20                  25                  30

Ala Glu Glu Val Ile Leu Leu Asp Ser Lys Ala Ser Gln Ala Glu Leu
            35                  40                  45

Gly Trp Thr Ala Leu Pro Ser Asn Gly Trp Glu Glu Ile Ser Gly Val
        50                  55                  60

Asp Glu His Asp Arg Pro Ile Arg Thr Tyr Gln Val Cys Asn Val Leu
65                  70                  75                  80

Glu Pro Asn Gln Asp Asn Trp Leu Gln Thr Gly Trp Ile Ser Arg Gly
                85                  90                  95

Arg Gly Gln Arg Ile Phe Val Glu Leu Gln Phe Thr Leu Arg Asp Cys
                100                 105                 110

Ser Ser Ile Pro Gly Ala Ala Gly Thr Cys Lys Glu Thr Phe Asn Val
            115                 120                 125

Tyr Tyr Leu Glu Thr Glu Ala Asp Leu Gly Arg Gly Arg Pro Arg Leu
        130                 135                 140

Gly Gly Ser Arg Pro Arg Lys Ile Asp Thr Ile Ala Ala Asp Glu Ser
145                 150                 155                 160

Phe Thr Gln Gly Asp Leu Gly Arg Lys Met Lys Leu Asn Thr Glu
                165                 170                 175

Val Arg Glu Ile Gly Pro Leu Ser Arg Arg Gly Phe His Leu Ala Phe
```

```
                180             185              190
Gln Asp Val Gly Ala Cys Val Ala Leu Val Ser Val Arg Val Tyr Tyr
            195                 200             205
Lys Gln Cys Arg Ala Thr Val Arg Gly Leu Ala Thr Phe Pro Ala Thr
            210                 215                 220
Ala Ala Glu Ser Ala Phe Ser Thr Leu Val Glu Val Ala Gly Thr Cys
225                 230                 235                 240
Val Ala His Ser Glu Gly Glu Pro Gly Ser Pro Pro Arg Met His Cys
                245                 250                 255
Gly Ala Asp Gly Glu Trp Leu Val Pro Val Gly Arg Cys Ser Cys Ser
            260                 265                 270
Ala Gly Phe Gln Glu Arg Gly Asp Phe Cys Glu Ala Cys Pro Pro Gly
            275                 280                 285
Phe Tyr Lys Val Ser Pro Arg Arg Pro Leu Cys Ser Pro Cys Pro Glu
            290                 295                 300
His Ser Arg Ala Leu Glu Asn Ala Ser Thr Phe Cys Val Cys Gln Asp
305                 310                 315                 320
Ser Tyr Ala Arg Ser Pro Thr Asp Pro Pro Ser Ala Ser Cys Thr Arg
                325                 330                 335
Pro Pro Ser Ala Pro Arg Asp Leu Gln Tyr Ser Leu Ser Arg Ser Pro
                340                 345                 350
Leu Val Leu Arg Leu Arg Trp Leu Pro Pro Ala Asp Ser Gly Gly Arg
            355                 360                 365
Ser Asp Val Thr Tyr Ser Leu Leu Cys Leu Arg Cys Gly Arg Glu Gly
            370                 375                 380
Pro Ala Gly Ala Cys Glu Pro Cys Gly Pro Arg Val Ala Phe Leu Pro
385                 390                 395                 400
Arg Gln Ala Gly Leu Arg Glu Arg Ala Ala Thr Leu Leu His Leu Arg
            405                 410                 415
Pro Gly Ala Arg Tyr Thr Val Arg Val Ala Ala Leu Asn Gly Val Ser
            420                 425                 430
Gly Pro Ala Ala Ala Gly Thr Thr Tyr Ala Gln Val Thr Val Ser
            435                 440                 445
Thr Gly Pro Gly Ala Pro Trp Glu Glu Gly Glu Ile Arg Arg Asp Arg
            450                 455                 460
Val Glu Pro Gln Ser Val Ser Leu Ser Trp Arg Glu Pro Ile Pro Ala
465                 470                 475                 480
Gly Ala Pro Gly Ala Asn Asp Thr Glu Tyr Glu Ile Arg Tyr Tyr Glu
                485                 490                 495
Lys Gly Gln Ser Glu Gln Ala Tyr Ser Met Val Lys Thr Gly Ala Pro
                500                 505                 510
Thr Val Thr Val Thr Asn Leu Lys Pro Ala Thr Arg Tyr Val Phe Gln
            515                 520                 525
Ile Arg Ala Ala Ser Pro Gly Pro Ser Trp Glu Ala Gln Ser Phe Asn
            530                 535                 540
Pro Ser Ile Glu Val Gln Thr Leu Gly Glu Ala Ala Ser Gly Ser Arg
545                 550                 555                 560
Asp Gln Ser Pro Ala Ile Val Val Thr Val Val Thr Ile Ser Ala Leu
                565                 570                 575
Leu Val Leu Gly Ser Val Met Ser Val Leu Ala Ile Trp Arg Arg Pro
            580                 585                 590
Cys Ser Tyr Gly Lys Gly Gly Gly Asp Ala His Asp Glu Glu Leu
            595                 600                 605
```

```
Tyr Phe His Phe Lys Val Pro Thr Arg Arg Thr Phe Leu Asp Pro Gln
610                 615                 620

Ser Cys Gly Asp Leu Leu Gln Ala Val His Leu Phe Ala Lys Glu Leu
625                 630                 635                 640

Asp Ala Lys Ser Val Thr Leu Glu Arg Ser Leu Gly Gly Arg Phe
                645                 650                 655

Gly Glu Leu Cys Cys Gly Cys Leu Gln Leu Pro Gly Arg Gln Glu Leu
                660                 665                 670

Leu Val Ala Val His Met Leu Arg Asp Ser Ala Ser Asp Ser Gln Arg
                675                 680                 685

Leu Gly Phe Leu Ala Glu Ala Leu Thr Leu Gly Gln Phe Asp His Ser
690                 695                 700

His Ile Val Arg Leu Glu Gly Val Val Thr Arg Gly Ser Thr Leu Met
705                 710                 715                 720

Ile Val Thr Glu Tyr Met Ser His Gly Ala Leu Asp Gly Phe Leu Arg
                725                 730                 735

Arg His Glu Gly Gln Leu Val Ala Gly Gln Leu Met Gly Leu Leu Pro
                740                 745                 750

Gly Leu Ala Ser Ala Met Lys Tyr Leu Ser Glu Met Gly Tyr Val His
                755                 760                 765

Arg Gly Leu Ala Ala Arg His Val Leu Val Ser Ser Asp Leu Val Cys
770                 775                 780

Lys Ile Ser Gly Phe Gly Arg Gly Pro Arg Asp Arg Ser Glu Ala Val
785                 790                 795                 800

Tyr Thr Thr Met Ser Gly Arg Ser Pro Ala Leu Trp Ala Ala Pro Glu
                805                 810                 815

Thr Leu Gln Phe Gly His Phe Ser Ser Ala Ser Asp Val Trp Ser Phe
                820                 825                 830

Gly Ile Ile Met Trp Glu Val Met Ala Phe Gly Glu Arg Pro Tyr Trp
                835                 840                 845

Asp Met Ser Gly Gln Asp Val Ile Lys Ala Val Glu Asp Gly Phe Arg
                850                 855                 860

Leu Pro Pro Pro Arg Asn Cys Pro Asn Leu Leu His Arg Leu Met Leu
865                 870                 875                 880

Asp Cys Trp Gln Lys Asp Pro Gly Glu Arg Pro Arg Phe Ser Gln Ile
                885                 890                 895

His Ser Ile Leu Ser Lys Met Val Gln Asp Pro Glu Pro Pro Lys Cys
                900                 905                 910

Ala Leu Thr Thr Cys Pro Arg Pro Thr Pro Leu Ala Asp Arg Ala
                915                 920                 925

Phe Ser Thr Phe Pro Ser Phe Gly Ser Val Gly Ala Trp Leu Glu Ala
                930                 935                 940

Leu Asp Leu Cys Arg Tyr Lys Asp Ser Phe Ala Ala Ala Gly Tyr Gly
945                 950                 955                 960

Ser Leu Glu Ala Val Ala Glu Met Thr Ala Gln Asp Leu Val Ser Leu
                965                 970                 975

Gly Ile Ser Leu Ala Glu His Arg Glu Ala Leu Leu Ser Gly Ile Ser
                980                 985                 990

Ala Leu Gln Ala Arg Val Leu Gln Leu Gln Gly Gln Gly Val Gln Val
                995                 1000                1005

<210> SEQ ID NO 2
<211> LENGTH: 7
<212> TYPE: PRT
<213> ORGANISM: Homo sapiens
```

<400> SEQUENCE: 2

Glu Ile Gly Pro Leu Ser Arg
1               5

<210> SEQ ID NO 3
<211> LENGTH: 19
<212> TYPE: PRT
<213> ORGANISM: Homo sapiens

<400> SEQUENCE: 3

Phe Ser Gln Ile His Ser Ile Leu Ser Lys Met Val Gln Asp Pro Glu
1               5                   10                  15

Pro Pro Lys

<210> SEQ ID NO 4
<211> LENGTH: 22
<212> TYPE: PRT
<213> ORGANISM: Homo sapiens

<400> SEQUENCE: 4

His Glu Gly Gln Leu Val Ala Gly Gln Leu Met Gly Leu Leu Pro Gly
1               5                   10                  15

Leu Ala Ser Ala Met Lys
            20

<210> SEQ ID NO 5
<211> LENGTH: 7
<212> TYPE: PRT
<213> ORGANISM: Homo sapiens

<400> SEQUENCE: 5

Leu Glu Gly Val Val Thr Arg
1               5

<210> SEQ ID NO 6
<211> LENGTH: 6
<212> TYPE: PRT
<213> ORGANISM: Homo sapiens

<400> SEQUENCE: 6

Ser Pro Leu Val Leu Arg
1               5

<210> SEQ ID NO 7
<211> LENGTH: 5526
<212> TYPE: DNA
<213> ORGANISM: Homo sapiens

<400> SEQUENCE: 7
ggctctgggg tctgggggca ttgctcagcg gtgctaggct ggcgcggctt gagccgccgc     60
cggactgaca gctcggtctg cggaccatgg agacctgcgc cggtccacac ccgctgcgcc    120
tcttcctctg ccggatgcag ctctgtctcg cgctgctttt gggaccctgg cggcctggga    180
ccgccgagga agttatcctc ctggattcca agcctcccag gccgagctgg gctggactg     240 cactgccaag taatgggtgg gaggagatca gcggcgtgga tgaacacgac cgtcccatcc    300
gcacgtacca agtgtgcaat gtgctggagc ccaaccagga caactggctg cagactggct    360
ggataagccg tggccgcggg cagcgcatct tcgtggaact gcagttcaca ctccgtgact    420
gcagcagcat ccctgcgcc gcgggtacct gcaaggagac cttcaacgtc tactacctgg    480
aaactgaggc cgacctgggc cgtgggcgtc ccgcctagg cggcagccgg ccccgcaaaa    540

```
tcgacacgat cgcggcggac gagagcttca cgcagggcga cctgggtgag cgcaagatga    600
agctgaacac agaggtgcgc gagatcggac cgctcagccg gcggggtttc cacctggcct    660
ttcaggacgt gggcgcatgc gtggcgcttg tctcggtgcg cgtctactac aagcagtgcc    720
gcgccaccgt gcggggcctg ccacgttcc cagccaccgc agccgagagc gccttctcca     780
cactggtgga agtggccgga acgtgcgtgg cgcactcgga aggggagcct ggcagccccc    840
cacgcatgca ctgcggcgcc gacggcgagt ggctggtgcc tgtgggccgc tgcagctgca    900
gcgcgggatt ccaggagcgt ggtgacttct gcgaagcctg tccccaggg ttttacaagg     960 tgtccccgcg gcggcccctc tgctcaccgt gcccagagca cagccgggcc ctggaaaacg    1020
cctccacctt ctgcgtgtgc caggacagct atgcgcgctc acccaccgac ccgccctcgg    1080
cttcctgcac ccggccgccg tcggcgccgc gggacctgca gtacagcctg agccgctcgc    1140
cgctggtgct gcgactgcgc tggctgccgc cggccgactc gggaggccgc tcggacgtca    1200
cctactcgct gctgtgcctg cgctgcggcc gcgagggccc ggcgggcgcc tgcgagccgt    1260
gcgggccgcg cgtggccttc ctaccgcgcc aggcagggct gcgggagcga ccgccacgc    1320 tgctgcacct gcggccgggc gcgcgctaca ccgtgcgcgt ggccgcgctc aacgcgtct    1380 cgggcccggc ggccgccgcg ggaaccacct acgcgcaggt caccgtctcc accgggcccg    1440
gggcgccctg ggaggaggat gagatccgca gggaccgagt ggaacccag agcgtgtccc     1500 tgtcgtggcg ggagcccatc cctgccggag cccctggggc caatgacacg gagtacgaga    1560
tccgatacta cgagaagggt cagagtgagc agacttactc catggtgaag acaggggcgc    1620
ccacagtcac cgtcaccaac ctgaagccgg ctacccgcta cgtctttcag atccgggccg    1680
cttccccggg gccatcctgg gaggcccaga gttttaaccc cagcattgaa gtacagaccc    1740
tgggggaggc tgcctcaggg tccagggacc agagccccgc cattgtcgtc accgtagtga    1800
ccatctcggc cctcctcgtc ctgggctccg tgatgagtgt gctggccatt tggaggaggc    1860
cctgcagcta tggcaaagga ggaggggatg cccatgatga agaggagctg tatttccact    1920
tcaaagtccc aacacgtcgc acattcctgg accccagag ctgtggggac ctgctgcagg     1980
ctgtgcatct gttcgccaag gaactggatg cgaaaagcgt cacgctggag aggagccttg    2040
gaggagggcg gtttggggag ctgtgctgtg gctgcttgca gctccccggt cgccaggagc    2100
tgctcgtagc cgtgcatatg ctgagggaca gcgcctccga ctcacagagg ctcggcttcc    2160
tggccgaggc cctcacgctg gccagttttg accatagcca catcgtgcgg ctggagggcg    2220
ttgttacccg aggaagcacc ttgatgattg tcaccgagta catgagccat ggggccctgg    2280
acggcttcct caggcggcac gaggggcagc tggtggctgg caactgatg gggttgctgc     2340 ctgggctggc atcagccatg aagtatctgt cagagatggg ctacgttcac cggggcctgg    2400
cagctcgcca tgtgctggtc agcagcgacc ttgtctgcaa gatctctggc ttcgggcggg    2460
gccccgggaa ccgatcagag gctgtctaca ccactatgag tggccggagc ccagcgctat    2520
gggccgctcc cgagacactt cagtttggcc acttcagctc tgccagtgac gtgtggagct    2580
tcggcatcat catgtgggag gtgatggcct ttggggagcg gccttactgg gacatgtctg    2640
gccaagacgt gatcaaggct gtggaggatg gcttccggct gccaccccc aggaactgtc     2700 ctaaccttct gcaccgacta atgctcgact gctggcagaa ggaccaggt gagcggccca     2760 ggttctccca gatccacagc atcctgagca agatggtgca ggaccagag ccccccaagt     2820 gtgccctgac tacctgtccc aggcctccca ccccactagc ggaccgtgcc ttctccacct    2880
tcccctcctt tggctctgtg ggcgcgtggc tggaggccct ggacctgtgc cgctacaagg    2940
```

```
acagcttcgc ggctgctggc tatgggagcc tggaggccgt ggccgagatg actgcccagg    3000
acctggtgag cctaggcatc tctttggctg aacatcgaga ggccctcctc agcgggatca    3060
gcgccctgca ggcacgagtg ctccagctgc agggccaggg ggtgcaggtg tgagtggacc    3120
ccattcttcc aaggcaggac tccggtgggg gtccagtccc ccagccctgc ccaaggaccg    3180
tggcaagctg cgctccagca gtgtgggagg gagcgctctc ttcctctgct gggcccaga     3240 tctggtgggg ccacagcttc cccgcttcca ctgcctgccc ctcccatttt cacgagtctg    3300
aacgccttgg ctaactcagt gcccctgaaa agaggttcaa atccctaggg aggacccctg    3360
agataacagc aggaggaaat tcggggtctc agagaaaagc tggggcaggg atgggaggga    3420
agacagtggg ttgagattgc cctggctcat gccctactgc catttgtacc cactgggggc    3480
tggggcctac cccgtggggt gttccctttt cccacagacc cattgaccag tcagacagcg    3540
tgggtcctgg gggggtcttc ttctacctgg cagtgactgc agctgcctgg tggctcaggc    3600 gtcggggggct gggccagagg tgcatccacc tcagctccct gtgccttggc aggggctgac    3660
tggacactgg ccaaggctca ggcaggcaaa gatggtgctg agctcagggg ctgatacccca   3720 agagccctag actcaggatc tggttctctgt gtcccccctgc cttgggctga cagttcaggg   3780
tgaggccaaa agtcctggcc aggccgggcc atgagaggcc ctggtgctcc ctggggcccc    3840
atgaggccct cgtgtgcatt cctttttatga acttagtggc caggacatct gggaaaagca    3900
taaagggcca tgttatctcc ccagggaccc aagagctttt ctctccagcc atgggagggg    3960
tgaagaggag actcagagat gggtcctctc tctcaaacag gctggtctaa cccccagtgt    4020
acagatgggg gaaactgagg ccaagtgagg agtcaggagc agagctgagg tcagaaccca    4080
atccaggggt aaggctggct ctggggagag agtccttggt cctgccctat ggcaccacca    4140
cttccctgta cagcccttgg ggactctaga ggcgactccc ctccagccag ctccgtgcct    4200
tgggcactac ccagccttcc atggagcccc tccctgctct gactttgaag agccctggca    4260
gaagtggttg tgctgagccc accgtggagt tccttatcca aagggcccc cgggaatggt     4320 ggggcccagt atgccagagc tttcgtaggg tggcaggaag gcagctggat tcagcaggg    4380 ccacagggac tgagtttgtt taggccgccc gtgacacttg tctgctctgc ttggctgtgt    4440
gttggtgggg tgggatgggg cgggaaagag gagacaagag gtaaagatga aaagacaca    4500 cagcctgccc ttgggggggct cagactagac caggagaaga gctcaggtac caagaagtaa    4560
ttccagggca ccatccacag tgcccagggc cccccaggag ccctctgggt cagtgggtag    4620
gtgggctgga gggggagata gccactctct taatgtgtga agttgagatg taagttgaac    4680
agggccttgc aggtgggaaa gggaaggttc tttccttggg gtgggtggag ttttcggcag    4740
gcaagatggc aggcctcgga caaaaggagt ccatgcagag aggctagcat gagaaagagc    4800
ccagaggcgg gaaggtgcag tgcctctttg cagagcaccc agaggtgggg gacagtgact    4860
cacagaggtg cctttggcct taccctgcca gcagcagctc ccctgctctt ggaatctccc    4920
cccagccccc tgcctccctg tctcctgagc acctgcccca gctcagtgac tctggggta    4980 ctggggagac caagatgttg ctaccacctt agtcaggggtt gggggagccc ccggccaggt    5040 gccctcagg atccgccttc cccacccctc ctgggaagcc tggaccagca tcccttcttg     5100
ggtggatgga gcctcgtcct catctccagc tacatcagtc attctctgca gggcaaaatc    5160
tcctccccct accccagctg tttctgcaga agggcccctg gctgtgttgg caggacttcg    5220
gtgtccaggg tagatctccc ctccactgag gagtgaggtc ccagaatcct gttgggtccc    5280
aggcctcagc cctgcacaga tgtgatgtgg ggcgatggct ctctgggaac cctctacaga    5340
```

```
tctattttta tatggaactt gttcactgga cagaggtggc ctgcaagccc ccattaccct    5400
ggtctgagct caccctggga gggagggggc cagtcggagg gggttccttc tggagatgtt    5460
tttatatttc ttgggttctc tatgcaggat aataaaaact tgtctgtgat aaaaaaaaaa    5520
aaaaaa                                                               5526
```